(12) United States Patent
Van Sinderen et al.

(10) Patent No.: US 9,771,624 B2
(45) Date of Patent: Sep. 26, 2017

(54) BIFIDOBACTERIUM LONGUM

(75) Inventors: Douwe Van Sinderen, Carrigrohane (IE); Jun Xu, Mason, OH (US); Wenzhu (Steven) Zhao, Mason, OH (US); Raymond A. Grant, Fairfield, OH (US); Song Yuli, Mason, OH (US); Charles Bascom, Hamilton, MA (US); Duane Larry Charbonneau, Mason, OH (US); Liam O'Mahony, Rathcormac (IE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/616,752

(22) Filed: Nov. 11, 2009

(65) Prior Publication Data
US 2010/0183559 A1 Jul. 22, 2010

Related U.S. Application Data

(60) Provisional application No. 61/113,513, filed on Nov. 11, 2008, provisional application No. 61/149,980, filed on Feb. 4, 2009.

(51) Int. Cl.
| | |
|---|---|
| *A01N 63/00* | (2006.01) |
| *A61K 39/02* | (2006.01) |
| *C12R 1/01* | (2006.01) |
| *A23C 9/123* | (2006.01) |
| *A23C 19/032* | (2006.01) |
| *A23C 19/06* | (2006.01) |
| *A23L 2/38* | (2006.01) |
| *A61K 35/745* | (2015.01) |
| *C12P 19/04* | (2006.01) |
| *A23L 33/135* | (2016.01) |

(52) U.S. Cl.
CPC .............. *C12R 1/01* (2013.01); *A23C 9/1234* (2013.01); *A23C 19/0323* (2013.01); *A23C 19/062* (2013.01); *A23L 2/382* (2013.01); *A23L 33/135* (2016.08); *A61K 35/745* (2013.01); *C12P 19/04* (2013.01); *A23Y 2300/55* (2013.01)

(58) Field of Classification Search
CPC ... A23L 1/3014; A23L 1/296; A23V 2002/00; A61K 35/747; A23K 1/009
USPC ................... 424/93.4, 234.1, 252.1
See application file for complete search history.

(56) References Cited

U.S. PATENT DOCUMENTS

| | | | |
|---|---|---|---|
| 7,183,101 B2* | 2/2007 | Arigoni et al. ............ | 435/252.9 |
| 2001/0049115 A1 | 12/2001 | Collins et al. | |
| 2009/0274661 A1 | 11/2009 | Mercenier et al. | |
| 2011/0177034 A1 | 7/2011 | Kildsgaard et al. | |

OTHER PUBLICATIONS

O'Mahony L et al., Gastroenterology. Mar. 2005;128(3):541-51. Lactobacillus and bifidobacterium in irritable bowel syndrome: symptom responses and relationship to cytokine profiles.*
Vitali et al International Journal of Antimicrobial Agents 31 (2008) 555-560 Molecular and phenotypic traits of in-vitro-selected mutants of Bifidobacterium resistant to rifaximin.*
Rudinger (in Peptide Hormones, Parsons (ed.), University Park Press: Baltimore, MD, pp. 1-7, 1976.*
Guo et al, Protein tolerance to random amino acid change, PNAS, 2004, vol. 101 (25), pp. 9205-9210.*
Voet et al., Biochemistry John Wiley and Sons, 1990, p. 126-129.*
Sheil et al Gastroenterology, (Apr. 2007) vol. 132, No. 4, Suppl. 2, pp. A209. Modulation of the commensal flora by probiotic feeding delays the onset and decreases the severity of disease in the collagen-induced arthritis (CIA) model in a strain-dependent manner.*
Shilling Physiology, (Apr. 2006) vol. 290, No. 4, pp. G839-G845. Refs: 31 Differential cytokine response from dendritic cells to commensal and pathogenic bacteria in different lymphoid compartments in humans.*
Ngo, in The Protein Folding Problem and Tertiary Structure Prediction, Merz et al. (eds.), Birkhauser Boston: Boston, MA, pp. 433 and 492-495, 1994.*
Carvalho et al., Survival of freeze-dried Lactobacillus plantarum and Lactobacillus rhamnosus during storage in the presence of protectants Biotechnology Letters 24: 1587-1591, 2002.*
Definition of capsule from Webster's Seventh New Collegiate Dictionary, G. C. Merriam Co. pp. 1-12; downloaded on Dec. 28, 2016.*
Definition of tablet from Webster's Seventh New Collegiate Dictionary, G. C. Merriam Co. pp. 1-12; downloaded on Dec. 28, 2016.*
Altschul, et al., Basic Local Alignment Search Tool, J Mol Biol. vol. 215 pp. 403-410 (1990).
McCarthy, et al., Double blind, placebo controlled trial of two probiotic strains in interleukin 10 knockout mice and mechanistic link with cytokine balance, Gut vol. 52(7) pp. 975-980 (Jul. 6, 2003).
Ouwehand, et al., Bifidobacterium microbiota and parameters of immune functionin in elderly subjects, FEMS Immunol Med Microbiol vol. 53 pp. 18-25 (2008).
Riley, M., Functions of the Gene Products of *Escherichia coli*, Microbiological Reviews, vol. 57(4) pp. 862-952 (Dec. 1993).

* cited by examiner

*Primary Examiner* — Maria Leavitt
(74) *Attorney, Agent, or Firm* — Amanda Herman; Amanda T. Barry

(57) ABSTRACT

The multiple embodiments described herein comprise the genome of a probiotic *Bifidobacterium longum* bifidobacteria strain and genes encoded by the genome. Various novel *Bifidobacterium longum* are described.

9 Claims, 8 Drawing Sheets

BIFIDOBACTERIUM LONGUM

CROSS-REFERENCES TO RELATED APPLICATIONS

The present application claims the benefit of U.S. Provisional Application No. 61/113,513 filed Nov. 11, 2008, and U.S. Provisional Application No. 61/149,980 filed Feb. 4, 2009 the complete contents of both of which are incorporated herein by reference.

FIELD OF THE INVENTION

The invention relates to the genome of a probiotic bifidobacteria strain and genes encoded by the genome. *Bifidobacteria* are one of several predominant culturable bacteria present in human colonic microflora.

BACKGROUND OF THE INVENTION

*Bifidobacteria* are considered to be probiotics as they are living organisms which exert healthy effects beyond basic nutrition when ingested in sufficient numbers. A high level of ingested bifidobacteria must reach their site of action in order to exert a probiotic effect. A minimum level of approximately $10^6$-$10^7$ viable bifidobacteria per gram intestinal contents has been suggested (Bouhnik, Y., Lait 1993). There are reports in the literature which show that in vivo studies completed in adults and in infants indicate that some strains of bifidobacteria are capable of surviving passage through the gastrointestinal tract. Significant differences have been observed between the abilities of different bifidobacteria strains to tolerate acid and bile salts, indicating that survival is an important criterion for the selection of potential probiotic strains.

Ingestion of bifidobacteria can improve gastrointestinal transit and may prevent or assist in the treatment of illnesses which may be caused by deficient or compromised microflora such as gastrointestinal tract (GIT) infections, constipation, irritable bowel syndrome (IBS), inflammatory bowel disease (IBD)—Crohn's disease and ulcerative colitis, food allergies, antibiotic-induced diarrhoea, cardiovascular disease, and certain cancers (e.g. colorectal cancer).

Because of their perceived health-promoting activities, bifidobacteria have in recent years enjoyed an increased amount of scientific scrutiny, which included the full genomic sequencing of a number of strains (reviewed by Liu et al., 2005). These genomic sequences will provide the genetic platforms that allow the study of the molecular mechanisms by which these micro organisms interact with their human host and elicit their probiotic function.

SUMMARY OF THE INVENTION

The invention provides an isolated and purified *Bifidobacterium longum* strain, excluding *Bifidobacterium longum* strain 35624 (NCIMB 41003), wherein the strain:
  a) expresses an exopolysaccharide; and
  b) comprises at least two nucleic acid sequences selected from the group comprising SEQ ID NO. 93 to SEQ ID No. 113 or nucleic acid sequences with at least 85% sequence homology thereto.

A *Bifidobacterium longum* strain according to the invention may include any 2 or more such as BI00778, BI00793; BI00778,BI00794; BI00778,BI00795 or any three or more such as BI00793,BI00794,BI00798; BI00794,BI00795, BI00796; BI00796,BI00797,BI00798 or any four or more such as BI00778,BI00779,BI00780,BI00794; BI00778, BI00779,BI00785,BI00786; BI00790,BI00791,BI00794, BI00798 or any five or more such as BI00783,BI00786, BI00790,BI00794,BI00798; BI00780,BI00782,BI00785, BI00786,BI00790; BI00778,BI00779,BI00787,BI00789, BI00798 or any six or more such as BI00778,BI00779, BI00780,BI00781,BI00782,BI00794; BI00782,BI00784, BI00785,BI00788,BI00792,BI00797; BI00781,BI00782, BI00783,BI00791,BI00796,BI00797 or any seven or more such as BI00779,BI00783,BI00784,BI00787,BI00791, BI00792,BI00797; BI00780,BI00789,BI00790,BI00793, BI00794,BI00797,BI00798; BI00783,BI00784,BI00786, BI00788,BI00789,BI00793,BI00796 or any eight or more such as BI00779,BI00782,BI00783,BI00784,BI00785, BI00794,BI00797,BI00798; BI00780,BI00787,BI00788, BI00789,BI00790,BI00793,BI00794,BI00795; BI00783, BI00784,BI00785,BI00786,BI00787,BI00793,BI00795, BI00798 or any nine or more such as BI00778,BI00780, BI00782,BI00784,BI00785,BI00787,BI00793,BI00795, BI00796; BI00779,BI00781,BI00782,BI00784,BI00786, BI00787,BI00793,BI00795,BI00797; BI00782,BI00783, BI00785,BI00786,BI00787,BI00789,BI00792,BI00796, BI00797 or any ten or more such as BI00778,BI00781, BI00784,BI00785,BI00786,BI00789,BI00790,BI00792, BI00793,BI00798; BI00779,BI00781,BI00784,BI00786, BI00787,BI00788,BI00791,BI00794,BI00795,BI00796; BI00782,BI00784,BI00785,BI00786,BI00790,BI00792, BI00794,BI00796,BI00797,BI00798 or any eleven or more such as BI00778,BI00781,BI00785,BI00787,BI00788, BI00790,BI00791,BI00792,BI00794,BI00795,BI00798; BI00779,BI00782,BI00785,BI00786,BI00789,BI00790, BI00793,BI00794,BI00795,BI00796, BI00797; BI00781, BI00783,BI00785,BI00787,BI00788,BI00789,BI00790, BI00793,BI00794,BI00795,BI00796 or any twelve or more such as BI00778,BI00781,BI00782,BI00783,BI00784, BI00785,BI00790,BI00791,BI00792,BI00795,BI00796, BI00797; BI00779,BI00785,BI00787,BI00788,BI00789, BI00790,BI00791,BI00792,BI00794,BI00796,BI00797, BI00798; BI00786,BI00787,BI00788,BI00789,BI00790, BI00791,BI00792,BI00793,BI00795,BI00796,BI00797, BI00798 or any thirteen or more such as BI00778,BI00779, BI00780,BI00782,BI00784,BI00789,BI00790,BI00791, BI00792,BI00793, BI00794,BI00795,BI00798; BI00778, BI00781,BI00782,BI00783,BI00786,BI00787,BI00789, BI00790,BI00791,BI00792,BI00795,BI00796,BI00798; BI00780,BI00781,BI00782,BI00783,BI00785,BI00786, BI00788,BI00790,BI00791,BI00792,BI00793,BI00797, BI00798 or any fourteen or more such as BI00778,BI00779, BI00780,BI00782,BI00783,BI00784,BI00785,BI00787, BI00789,BI00791,BI00793,BI00794,BI00795,BI00797; BI00778,BI00780,BI00781,BI00782,BI00784,BI00785, BI00786,BI00788,BI00789,BI00792,BI00793 ,BI00794, BI00796,BI00797; BI00779,BI00780,BI00781,BI00782, BI00783,BI00784,BI00785,BI00787,BI00790,BI00791, BI00794,BI00796,BI00797,BI00798 or any fifteen or more such as BI00778,BI00779,BI00780,BI00781,BI00782, BI00783,BI00784,BI00785,BI00786,BI00787,BI00788, BI00789,BI00790,BI00792,BI00798; BI00778,BI00780, BI00781,BI00782,BI00785,BI00787,BI00788,BI00789, BI00790,BI00791,BI00793,BI00794,BI00795,BI00796, BI00798; BI00780,BI00782,BI00783,BI00784,BI00785, BI00786,BI00787,BI00789,BI00790,BI00791,BI00793, BI00795,BI00796,BI00797,BI00798 or any sixteen or more such as BI00778,BI00779,BI00780,BI00781,BI00782, BI00784,BI00785,BI00787,BI00789,BI00790,BI00791, BI00792,BI00793,BI00795,BI00797,BI00798; BI00778, BI00779,BI00781,BI00783,BI00784,BI00785,BI00787, BI00788,BI00789,BI00790, BI00791,BI00792,BI00794, BI00795,BI00797,BI00798; BI00780,BI00781,BI00782, BI00783,BI00784,BI00785,BI00787,BI00788,BI00789, BI00790,BI00792,BI00793,BI00795,BI00796,BI00797, BI00798 or any seventeen or more such as BI00778, BI00779,BI00780,BI00781,BI00782,BI00784,BI00785, BI00787,BI00788,BI00789,BI00790,BI00793,BI00794, BI00795,BI00796,BI00797,BI00798; BI00778,BI00780, BI00781,BI00782,BI00783,BI00785,BI00786,BI00787, BI00789,BI00790,BI00791,BI00792,BI00793,BI00794, BI00795,BI00796,BI00797; BI00779,BI00780,BI00782, BI00783,BI00784,BI00785,BI00787,BI00788,BI00789, BI00790,BI00791,BI00792,BI00793,BI00794,BI00795, BI00797,BI00798 or any eighteen or more such as BI00778, BI00779,BI00780,BI00781,BI00782,BI00783,BI00784, BI00785,BI00787,BI00788,BI00789,BI00791,BI00792, BI00793,BI00794,BI00795,BI00796,BI00798; BI00778, BI00779,BI00781,BI00782,BI00783,BI00784,BI00785, BI00786,BI00787,BI00788,BI00789,BI00790,BI00792, BI00794,BI00795,BI00796,BI00797,BI00798; BI00779, BI00781,BI00782,BI00783,BI00784,BI00785,BI00786, BI00787,BI00788,BI00789, BI00790,BI00791,BI00792, BI00793,BI00794,BI00795,BI00796,BI00797 or any nineteen or more such as BI00778,BI00779,BI00780, BI00781,BI00782,BI00783,BI00784,BI00785,BI00786, BI00787,BI00788,BI00789,BI00790,BI00791,BI00792, BI00794,BI00795,BI00796,BI00797; BI00778,BI00779, BI00780,BI00782,BI00783,BI00784,BI00785,BI00786, BI00787,BI00788, BI00789,BI00790,BI00791,BI00792, BI00793,BI00794,BI00795,BI00796,BI00797; BI00779, BI00780,BI00781,BI00782,BI00784,BI00785,BI00786, BI00787,BI00788,BI00789,BI00790,BI00791,BI00792, BI00793,BI00794,BI00795,BI00796,BI00797,BI00798 or any twenty or more such as BI00778,BI00779,BI00780, BI00781,BI00782,BI00783,BI00784,BI00785,BI00786, BI00787,BI00788,BI00789,BI00790,BI00791,BI00792, BI00793,BI00794,BI00795,BI00797,BI00798; BI00778, BI00779,BI00780,BI00781,BI00782,BI00783,BI00784, BI00785,BI00786,BI00787,BI00789,BI00790,BI00791, BI00792,BI00793,BI00794,BI00795,BI00796,BI00797, BI00798; BI00778,BI00779,BI00780,BI00782,BI00783, BI00784,BI00785,BI00786,BI00787,BI00788,BI00789, BI00790,BI00791,BI00792,BI00793,BI00794,BI00795, BI00796,BI00797,BI00798 or all twenty one of the nucleic acid sequences selected from the group comprising SEQ ID No. 93 to SEQ ID No. 113 or sequences homologous thereto.

The strain may comprise at least three nucleic acid sequences selected from the group comprising SEQ ID NO. 93 to SEQ ID No. 113 or nucleic acid sequences with at least 85% sequence homology thereto. The strain may comprise at least four nucleic acid sequences selected from the group comprising SEQ ID NO. 93 to SEQ ID No. 113 or nucleic acid sequences with at least 85% sequence homology thereto. The strain may comprise at least five nucleic acid sequences selected from the group comprising SEQ ID NO. 93 to SEQ ID No. 113 or nucleic acid sequences with at least 85% sequence homology thereto. The strain may comprise at least six nucleic acid sequences selected from the group comprising SEQ ID NO. 93 to SEQ ID No. 113 or nucleic acid sequences with at least 85% sequence homology thereto. The strain may comprise at least seven nucleic acid sequences selected from the group comprising SEQ ID NO. 93 to SEQ ID No. 113 or nucleic acid sequences with at least 85% sequence homology thereto. The strain may comprise at least eight nucleic acid sequences selected from the group comprising SEQ ID NO. 93 to SEQ ID No. 113 or nucleic acid sequences with at least 85% sequence homology thereto. The strain may comprise at least nine nucleic acid sequences selected from the group comprising SEQ ID NO. 93 to SEQ ID No. 113 or nucleic acid sequences with at least 85% sequence homology thereto. The strain may comprise at least ten nucleic acid sequences selected from the group comprising SEQ ID NO. 93 to SEQ ID No. 113 or nucleic acid sequences with at least 85% sequence homology thereto. The strain may comprise at least twelve nucleic acid sequences selected from the group comprising SEQ ID NO. 93 to SEQ ID No. 113 or nucleic acid sequences with at least 85% sequence homology thereto. The strain may comprise at least three nucleic acid sequences selected from the group comprising SEQ ID NO. 93 to SEQ ID No. 113 or nucleic acid sequences with at least 85% sequence homology thereto. The strain may comprise at least thirteen nucleic acid sequences selected from the group comprising SEQ ID NO. 93 to SEQ ID No. 113 or nucleic acid sequences with at least 85% sequence homology thereto. The strain may comprise at least fourteen nucleic acid sequences selected from the group comprising SEQ ID NO. 93 to SEQ ID No. 113 or nucleic acid sequences with at least 85% sequence homology thereto. The strain may comprise at least fifteen nucleic acid sequences selected from the group comprising SEQ ID NO. 93 to SEQ ID No. 113 or nucleic acid sequences with at least 85% sequence homology thereto. The strain may comprise at least sixteen nucleic acid sequences selected from the group comprising SEQ ID NO. 93 to SEQ ID No. 113 or nucleic acid sequences with at least 85% sequence homology thereto. The strain may comprise at least seventeen nucleic acid sequences selected from the group comprising SEQ ID NO. 93 to SEQ ID No. 113 or nucleic acid sequences with at least 85% sequence homology thereto. The strain may comprise at least eighteen nucleic acid sequences selected from the group comprising SEQ ID NO. 93 to SEQ ID No. 113 or nucleic acid sequences with at least 85% sequence homology thereto. The strain may comprise at least nineteen nucleic acid sequences selected from the group comprising SEQ ID NO. 93 to SEQ ID No. 113 or nucleic acid sequences with at least 85% sequence homology thereto. The strain may comprise at least twenty nucleic acid sequences selected from the group comprising SEQ ID NO. 93 to SEQ ID No. 113 or nucleic acid sequences with at least 85% sequence homology thereto. The strain may comprise all twenty one nucleic acid sequences selected from the group comprising SEQ ID NO. 93 to SEQ ID No. 113 or nucleic acid sequences with at least 85% sequence homology thereto.

The strain may not comprise the nucleic acid sequence of SEQ ID No. 112.

The strain may comprise at least one nucleic acid sequence selected from the group comprising SEQ ID No. 114 to SEQ ID No. 132 or nucleic acid sequences with at least 85% sequence homology thereto.

The strain may comprise at least two nucleic acid sequences selected from the group comprising SEQ ID No. 114 to SEQ ID No. 132 or nucleic acid sequences with at least 85% sequence homology thereto. The strain may comprise at least three nucleic acid sequences selected from the group comprising SEQ ID No. 114 to SEQ ID No. 132 or nucleic acid sequences with at least 85% sequence homology thereto. The strain may comprise at least four nucleic acid sequences selected from the group comprising SEQ ID No. 114 to SEQ ID No. 132 or nucleic acid sequences with at least 85% sequence homology thereto. The strain may comprise at least five nucleic acid sequences selected from the group comprising SEQ ID No. 114 to SEQ ID No. 132 or nucleic acid sequences with at least 85% sequence homology thereto. The strain may comprise at least six nucleic acid sequences selected from the group comprising SEQ ID No. 114 to SEQ ID No. 132 or nucleic acid sequences with at least 85% sequence homology thereto. The strain may comprise at least seven nucleic acid sequences selected from the group comprising SEQ ID No. 114 to SEQ ID No. 132 or nucleic acid sequences with at least 85% sequence homology thereto. The strain may comprise at least eight nucleic acid sequences selected from the group comprising SEQ ID No. 114 to SEQ ID No. 132 or nucleic acid sequences with at least 85% sequence homology thereto. The strain may comprise at least nine nucleic acid sequences selected from the group comprising SEQ ID No. 114 to SEQ ID No. 132 or nucleic acid sequences with at least 85% sequence homology thereto. The strain may comprise at least ten nucleic acid sequences selected from the group comprising SEQ ID No. 114 to SEQ ID No. 132 or nucleic acid sequences with at least 85% sequence homology thereto. The strain may comprise at least eleven nucleic acid sequences selected from the group comprising SEQ ID No. 114 to SEQ ID No. 132 or nucleic acid sequences with at least 85% sequence homology thereto. The strain may comprise at least twelve nucleic acid sequences selected from the group comprising SEQ ID No. 114 to SEQ ID No. 132 or nucleic acid sequences with at least 85% sequence homology thereto. The strain may comprise at least thirteen nucleic acid sequences selected from the group comprising SEQ ID No. 114 to SEQ ID No. 132 or nucleic acid sequences with at least 85% sequence homology thereto. The strain may comprise at least fourteen nucleic acid sequences selected from the group comprising SEQ ID No. 114 to SEQ ID No. 132 or nucleic acid sequences with at least 85% sequence homology thereto. The strain may comprise at least fifteen nucleic acid sequences selected from the group comprising SEQ ID No. 114 to SEQ ID No. 132 or nucleic acid sequences with at least 85% sequence homology thereto. The strain may comprise at least sixteen nucleic acid sequence selected from the group comprising SEQ ID No. 114 to SEQ ID No. 132 or nucleic acid sequences with at least 85% sequence homology thereto. The strain may comprise at least seventeen nucleic acid sequences selected from the group comprising SEQ ID No. 114 to SEQ ID No. 132 or nucleic acid sequences with at least 85% sequence homology thereto. The strain may comprise at least eigteens nucleic acid sequence selected from the group comprising SEQ ID No. 114 to SEQ ID No. 132 or nucleic acid sequences with at least 85% sequence homology thereto. The strain may comprise all ninteen nucleic acid sequences selected from the group comprising SEQ ID No. 114 to SEQ ID No. 132 or nucleic acid sequences with at least 85% sequence homology thereto The strain may comprise a single nucleic acid sequence selected from the group comprising SEQ ID No. 114 to SEQ ID No. 132 or nucleic acid sequences with at least sequence homology thereto. The strain may comprise a nucleic acid sequence of SEQ ID No. 132 or a nucleic acid sequence with at least sequence homology thereto.

The strain may comprise two nucleic acid sequences selected from the group comprising SEQ ID No. 114 to SEQ ID No. 132 or nucleic acid sequences with at least 85% sequence homology thereto. The strain may comprise the nucleic acid sequences of SEQ ID No. 131 and SEQ ID No. 132 or nucleic acid sequences with at least 85% sequence homology thereto.

The invention also provides an isolated and purified *Bifidobacterium longum* strain wherein the strain:

a) expresses an exopolysaccharide; and
b) comprises at least two nucleic acid sequences selected from the group comprising SEQ ID NO. 93 to SEQ ID No. 113 or nucleic acid sequences with at least 85% sequence homology thereto; and
c) comprises a nucleic acid sequence of SEQ ID No. 132 or a nucleic acid sequence with at least 85% sequence homology thereto; and/or
d) comprises a nucleic acid sequence of SEQ ID No. 131 or a nucleic acid sequence with at least 85% sequence homology thereto.

In one embodiment, $1\times10^7$ CFU/ml of the strain may induce an [IL10]: [IL12] ratio of at least 10 in a peripheral blood mononuclear cell (PMBC) co-incubation assay. The strain may be in the form of a bacterial broth. The strain may be in the form of a freeze-dried powder.

The invention further provides an isolated and purified *Bifidobacterium longum* strain wherein the strain:

a) expresses an exopolysaccharide; and
b) comprises at least two nucleic acid sequences selected from the group comprising SEQ ID NO. 93 to SEQ ID No. 113 or nucleic acid sequences with at least 85% sequence homology thereto; and
c) comprises a nucleic acid sequence of SEQ ID No. 132 or a nucleic acid sequence with at least 85% sequence homology thereto; and/or a nucleic acid sequence of SEQ ID No. 131 or a nucleic acid sequence with at least 85% sequence homology thereto; and
d) induces an [IL10]: [IL12] ratio of at least 10 in a peripheral blood mononuclear cell (PMBC) co-incubation assay at a concentration of $1\times10^7$ CFU/ml bacteria.

The invention also provides an isolated strain of *Bifidobacterium longum* BL1207 (PTA-9608).

The invention further provides an isolated strain of *Bifidobacterium longum* AH121A (NCIMB 41675).

The invention further still provides an isolated strain of *Bifidobacterium longum* AH1714 (NCIMB 41676).

The isolated strain may be in the form of viable cells. The isolated strain may be in the form of non-viable cells.

The invention also provides a formulation comprising an isolated strain of *Bifidobacterium longum* as described herein. The formulation may comprise an ingestable carrier. The ingestable carrier may be a pharmaceutically acceptable carrier such as a capsule, tablet or powder. The ingestable carrier may be a food product such as acidified milk, yoghurt, frozen yoghurt, milk powder, milk concentrate, cheese spreads, dressings or beverages. The formulation may comprise a strain that is present at more than $10^6$ cfu per gram of ingestable carrier.

The invention further provides a composition comprising an isolated strain of *Bifidobacterium longum* as described herein and a pharmaceutically acceptable carrier.

The invention also provides for the use of a *Bifidobacterium longum* strain as described herein as a probiotic strain.

The invention also provides a method for identifying an exopolysaccharide expressing *Bifidobacterium longum* strain comprising the steps of:

a) obtaining a sample comprising bacteria;
b) extracting nucleic acid from the sample;
c) amplifying the extracted nucleic acid in the presence of at least two primers derived from a nucleic acid sequence selected from the group comprising: SEQ ID No. 2, SEQ ID No. 3, SEQ ID No. 10 to SEQ ID No. 12, SEQ ID No. 93 to SEQ ID No. 132 or a nucleic acid sequence with at least 85% sequence homology thereto;
d) identifying a bacterial strain that expresses an exopolysaccharide.

The primer may comprise at least 10 consecutive bases from a nucleic acid sequence selected from the group comprising: SEQ ID No. 2, SEQ ID No. 3, SEQ ID No. 10 to SEQ ID No. 12 and SEQ ID No. 93 to SEQ ID No. 132.

The primer may comprise a nucleic acid sequence selected from the group comprising: SEQ ID No. 10 to SEQ ID No. 12, SEQ ID No. 13 to SEQ ID No. 92 or a nucleic acid sequence with at least 85% sequence homology thereto.

The step of identifying a bacterial strain that expresses an exopolysaccharide may comprise growing the bacterial strain on a Congo red agar plate.

The sample is a mammalian sample. The sample may be a human derived sample. The sample may be a fecal sample.

The invention also provides for a *Bifidobacterium longum* strain identified by described herein. The *Bifidobacterium longum* strain may be in the form of viable cells. The *Bifidobacterium longum* strain may be in the form of non-viable cells.

The invention further provides for a formulation comprising a *Bifidobacterium longum* strain as described herein. The formulation may comprise an ingestable carrier. The ingestable carrier may be a pharmaceutically acceptable carrier such as a capsule, tablet or powder. The ingestable carrier may be a food product such as acidified milk, yoghurt, frozen yoghurt, milk powder, milk concentrate, cheese spreads, dressings or beverages. The strain may be present at more than $10^6$ cfu per gram of ingestable carrier in the formulation.

The invention also provides a composition comprising a *Bifidobacterium longum* strain as described herein and a pharmaceutically acceptable carrier.

In one embodiment of the invention there is a method for identifying exopolysaccharide secreting bacterial strains comprising the steps of:
- obtaining a sample comprising bacteria;
- extracting DNA from the sample;
- amplifying the extracted DNA in the presence of at least one DNA primer derived from the DNA sequence of SEQ ID No. 2 and/or SEQ ID No. 3; and
- identifying a bacterial strain that expresses an exopolysaccharide.

The extracted DNA may be amplified by real time PCR. The DNA may be amplified in the presence of at least one primer of the nucleic acid sequence of SEQ ID No. 10, SEQ ID No. 11 or SEQ ID No. 12.

The sample may be a human derived sample such as a fecal sample.

In another embodiment, the invention also provides for a bacterial strain identified by the method described herein.

In another embodiment, the invention further provides for the use of a bacterial strain identified by the method described herein as a probiotic bacteria.

In yet another embodiment, the invention also provides a formulation comprising a bacterial strain identified by the method described herein.

In another embodiment, the invention further provides a composition comprising a bacterial strain identified by the method described herein and a pharmaceutically acceptable carrier.

In another embodiment, the invention also provides an isolated bifidobacterial longum strain BL1207 (PTA-9608).

In yet another embodiment, the invention further provides a formulation comprising an isolated bifidobacterial longum strain BL1207 (PTA-9608).

In another embodiment, the invention also provides a composition comprising an isolated bifidobacterial longum strain BL1207 (PTA-9608) and a pharmaceutically acceptable carrier.

In another embodiment, the invention further provides a DNA array/chip comprising at least one polynucleotide derived from the nucleic acid sequence of SEQ ID NO. 1, SEQ ID No. 2, or SEQ ID No. 3.

In one embodiment, the invention also provides a computer readable medium comprising a nucleic acid sequence of SEQ ID NO. 1, SEQ ID No. 2, or SEQ ID No. 3 or parts thereof.

A *Bifidobacterium longum* strain in accordance with an embodiment of the invention may express or produce EPS at a yield of between about 10 mg/L to about 1000 mg/L of bacterial culture.

There are a number of strains of *Bifidobacteria* which are already deposited under the Budapest Treaty. These include the strain deposited at the NCIMB under the number 41003, the genome of which is presented herein. As this is a known strain, this strain is specifically disclaimed for the claims to the strains per se. In so far as the following strains may fall within the scope of the patent claims at the relevant date(s), the following claims are also disclaimed: ATCC BAA-999, CNCM I-1227, CNCM I-1228, CNCM I-2168, CNCM I-2170, CNCM I-2618, CNCM I-3446, CNCM I-3853, CNCM I-3854, CNCM I-3855, NCIMB 41290, NCIMB 41291, NCIMB 41382, NCIMB 41387, NTCC 2705.

BRIEF DESCRIPTION OF THE DRAWINGS

The invention will be more clearly understood from the following description thereof given by way of example only with reference to the accompanying drawings in which.

DETAILED DESCRIPTION OF THE INVENTION

Figure 1:
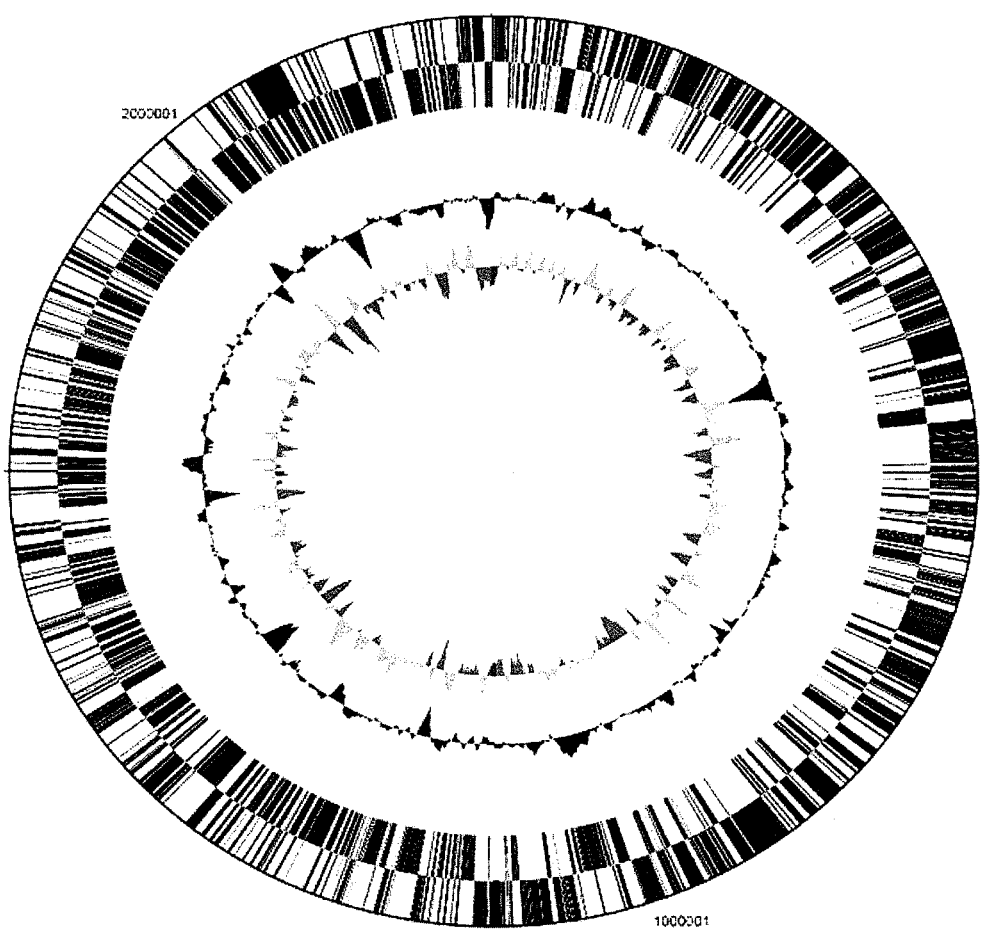
FIG. 1 is a Genome atlas of *Bifidobacterium longum* biotype infantis UCC 35624. The numbers on the genome (1, 1000001, 200001) refer to base pair position. 1 refers to the adenine nucleotide of the ATG start codon of the gene encoding the predicted replication protein. The outer circle (two strands, black and white) refers to the gene density within the chromosome. The second circle (middle circle—black) refers to the GC content and the innermost circle refers to the GC skew.
Figure 2:
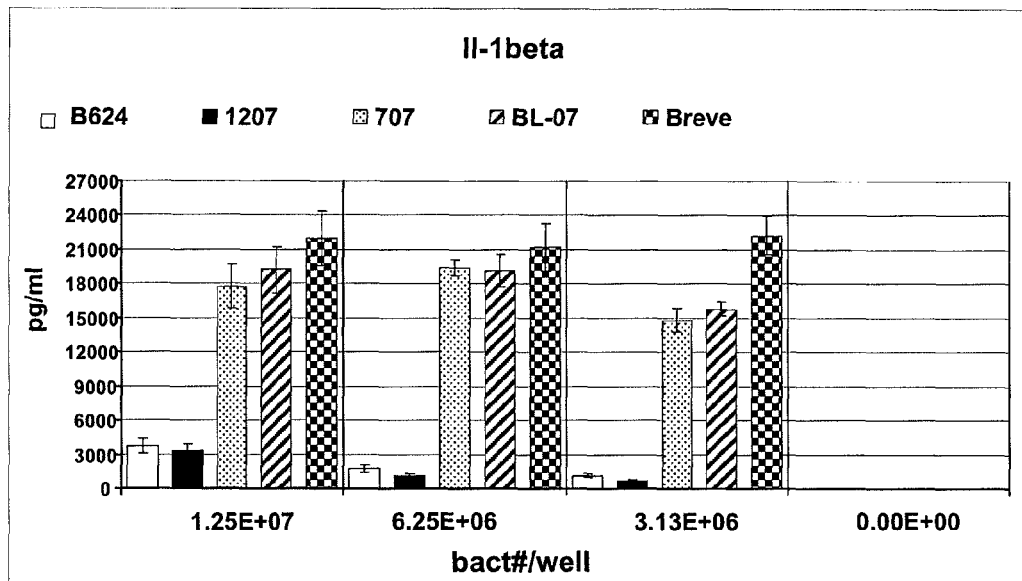
FIG. 2 is a bar chart showing the induction profile of IL-1beta in PBMCs by *Bifidobacterium longum* infantis strain UCC35624 (B624), *Bifidobacterium longum* strain 1207 (BL1207), *Bifidobacterium longum* strain 15707 (BL15707), *Bifidobacterium lactis* (BL-07) and *Bifidobacterium breve* strain 8807 [UCC2003] (breve)
Figure 3:
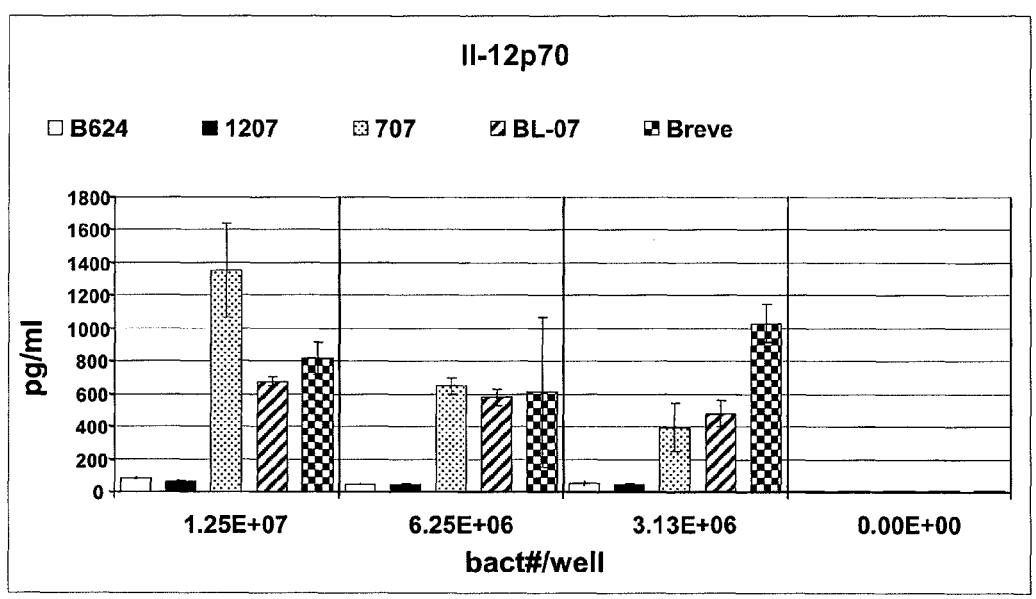
FIG. 3 is a bar chart showing the induction profile of IL-12p70 in PBMCs by *Bifidobacterium longum* infantis strain UCC35624 (B624), *Bifidobacterium longum* strain 1207 (BL1207), *Bifidobacterium longum* strain 15707 (BL15707), *Bifidobacterium lactis* (BL-07) and *Bifidobacterium breve* strain 8807 [UCC2003] (breve)
Figure 4:
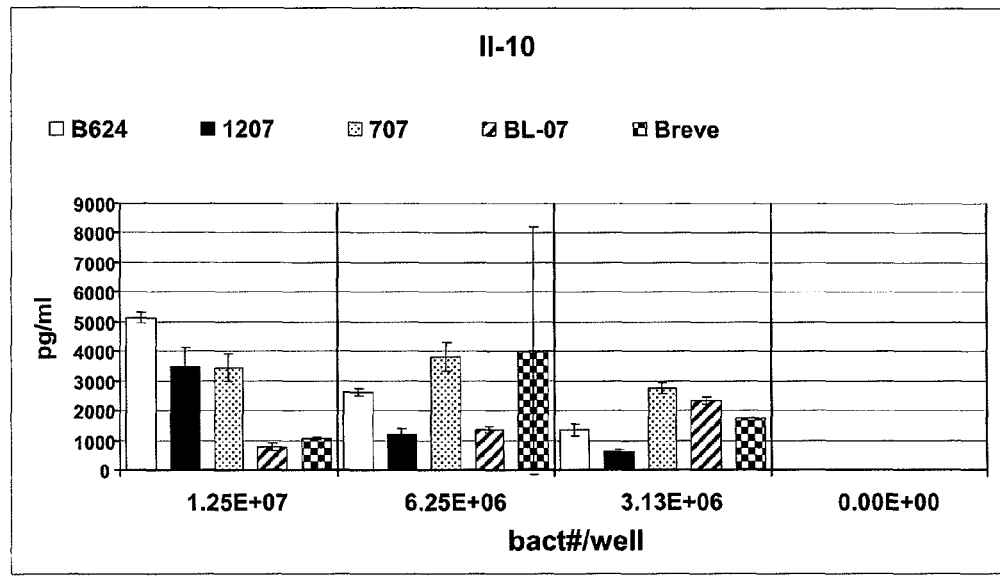
FIG. 4 is a bar chart showing the induction profile of IL-10 in PBMCs by *Bifidobacterium longum* infantis strain UCC35624 (B624), *Bifidobacterium longum* strain 1207 (BL1207), *Bifidobacterium longum* strain 15707 (BL15707), *Bifidobacterium lactis* (BL-07) and *Bifidobacterium breve* strain 8807 [UCC2003] (breve)
Figure 5:
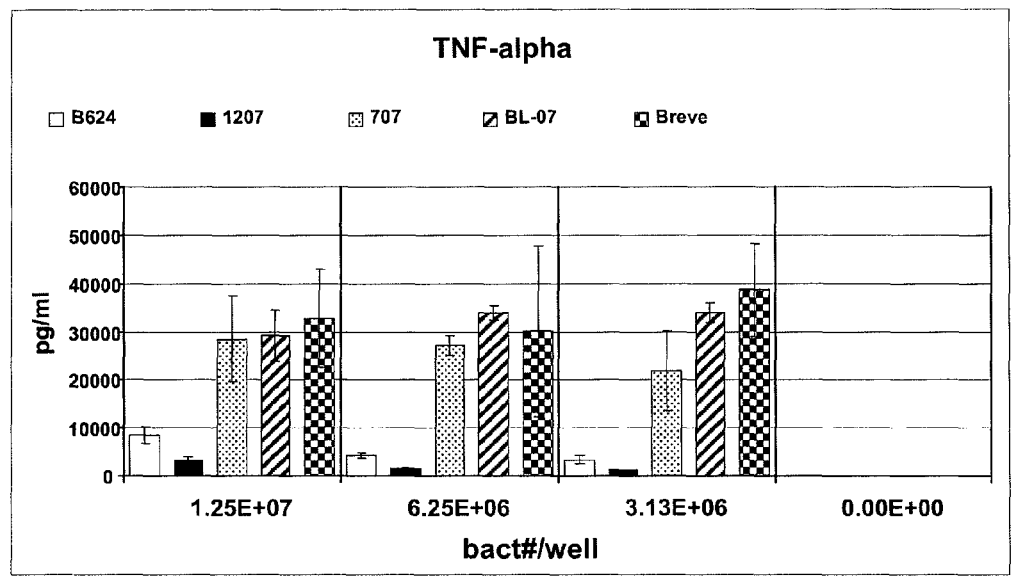
FIG. 5 is a bar chart showing the induction profile of TNF-alpha in PBMCs by *Bifidobacterium longum* infantis strain UCC35624 (B624), *Bifidobacterium longum* strain 1207 (BL1207), *Bifidobacterium longum* strain 15707 (BL15707), *Bifidobacterium lactis* (BL-07) and *Bifidobacterium breve* strain 8807 [UCC2003] (breve).
Figure 6:
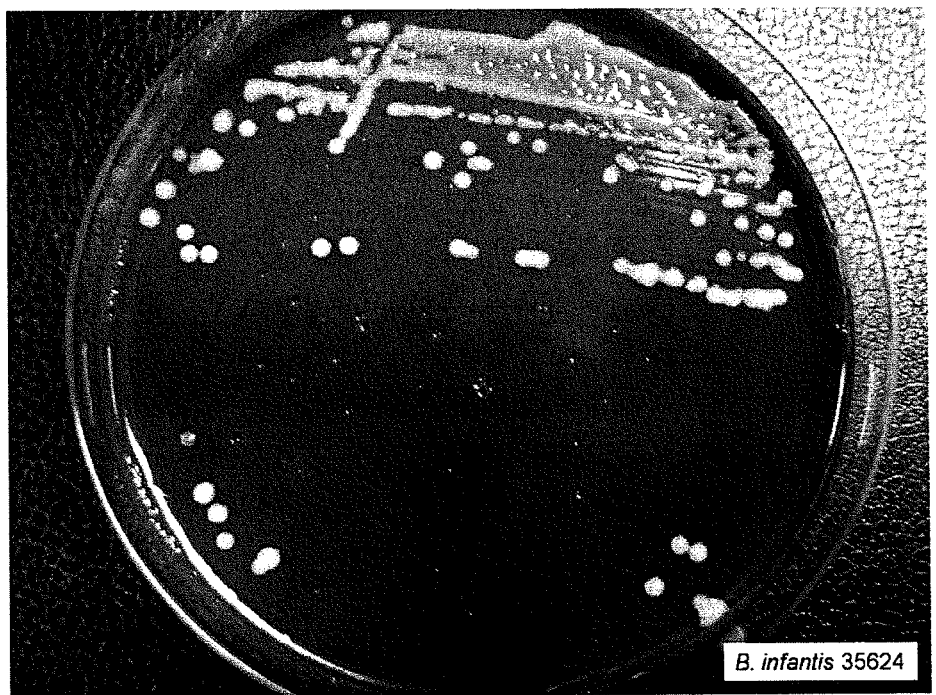
FIG. 6 is a photograph of *B. longum* 35624 grown on a Congo Red Agar plate.
Figure 7:
FIG. 7 is a photograph of *B. longum* AH121A grown on a Congo Red Agar plate.
Figure 8:
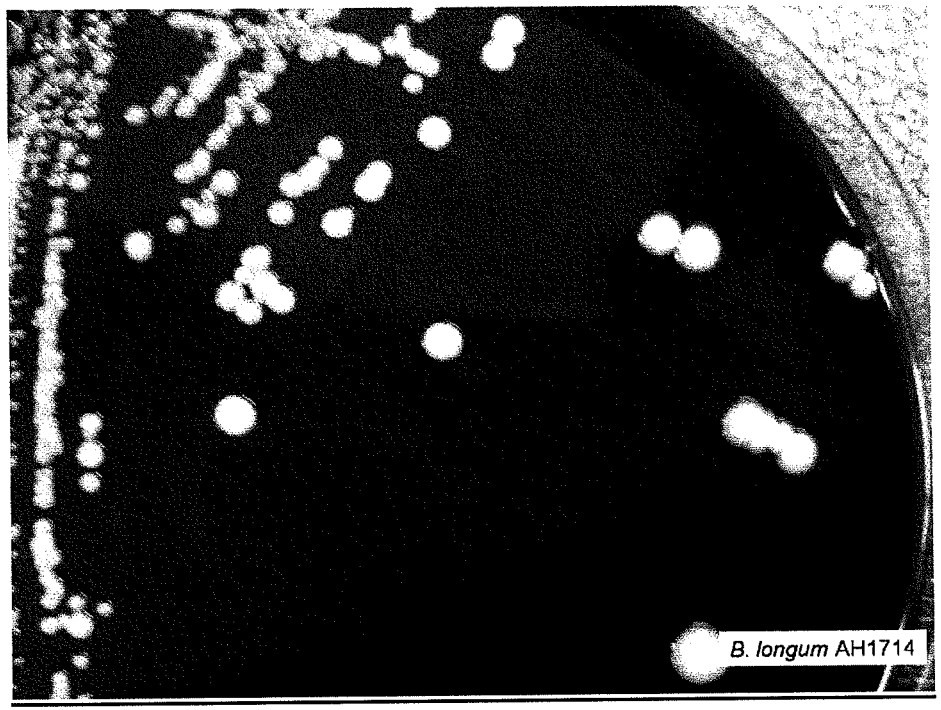
FIG. 8 is a photograph of *B. longum* AH1714 grown on a Congo Red Agar plate.
Figure 9:
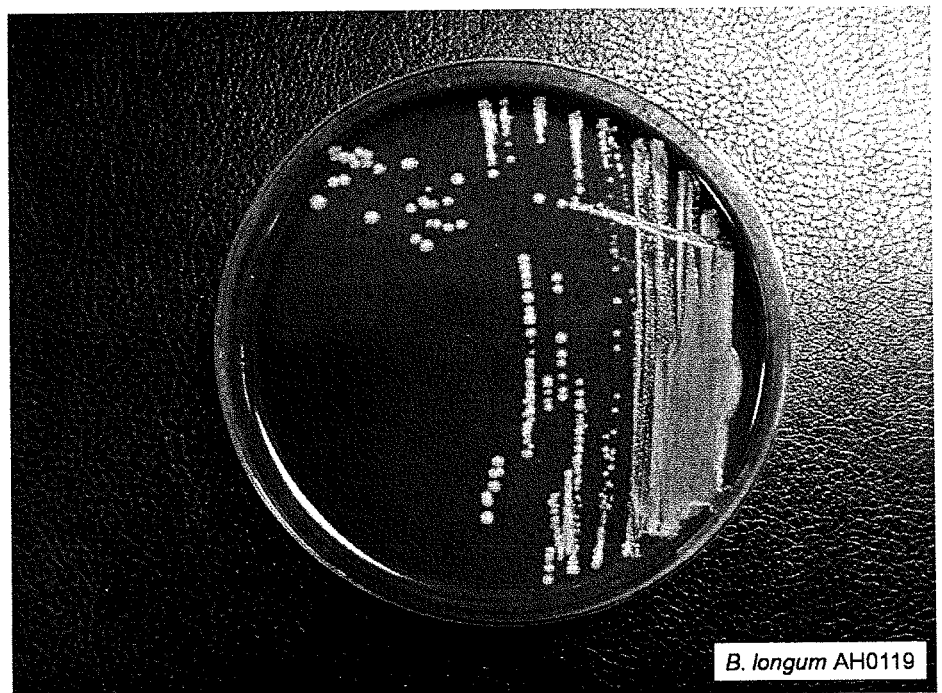
FIG. 9 is a photograph of *B. longum* AH0119 grown on a Congo Red Agar plate.
Figure 10:
FIG. 10 is a photograph of *B. breve* UCC2003 grown on a Congo Red Agar plate.
Figure 11:
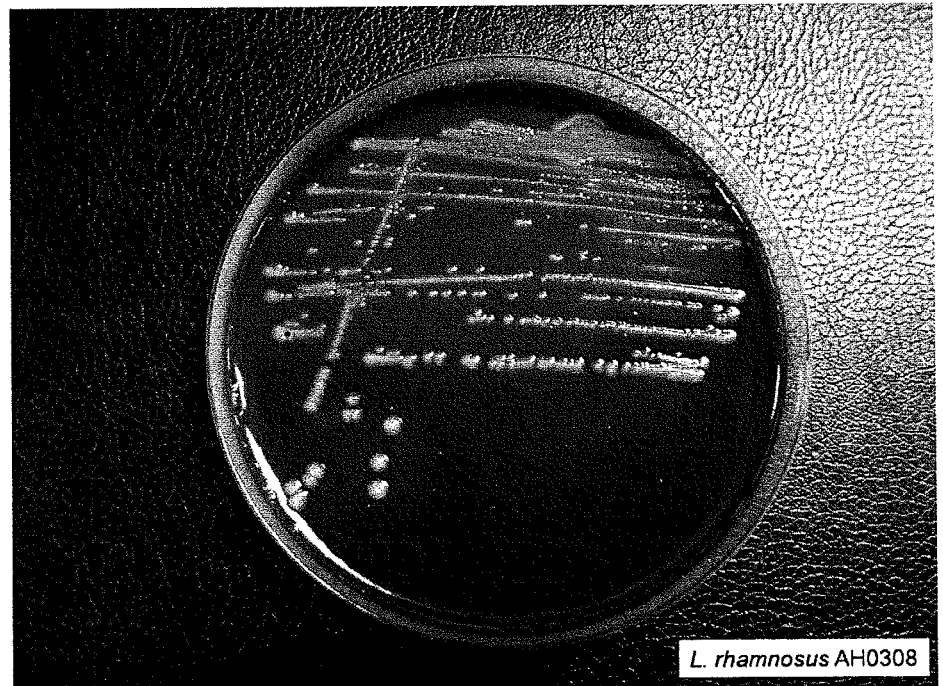
FIG. 11 is a photograph of *L. Rhamnosus* AH308 grown on a Congo Red Agar plate.
Figure 12:
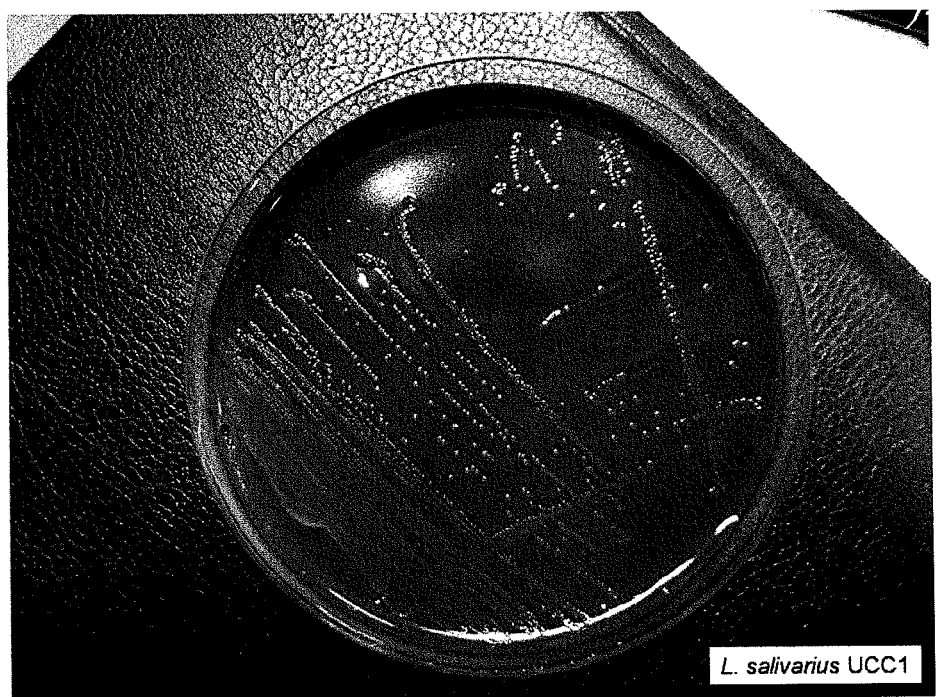
FIG. 12 is a photograph of *L. salivarius* UCC1 grown on a Congo Red Agar plate.

Disclosed herein is an isolated polynucleotide of SEQ ID No. 1. The polynucleotide of SEQ ID No. 1 encodes a strain of *Bifidobacterium*. The *Bifidobacterium* encoded by the isolated polynucleotide sequence has a number of unique genes. The unique genes encoded by the polynucleotide have a unique order in the sequence of SEQ ID No. 1. As used herein, the term "unique genes", mean genes that are not found in the currently available sequences of Bifodobacterium. As used herein, the term "unique order", means that the position/sequence of the genes in the polynucleotide is not found in the currently available sequences of Bifodobacterium. The unique genes present in the isolated polynucleotide may be interspersed with nucleic acid residues that code for other (known) genes or stretches of non-coding sequence but the overall order/sequence of the unique genes in the isolated polynucleotide is in itself unique compared to the order of genes found in the currently available sequences of *Bifodobacterium*.

The polynucleotide was isolated from a strain of the bacterial species *Bifidobacterium longum* biotype infantis with the strain designation UCC 35624. A deposit of *Bifidobacterium longum* biotype infantis strain UCC 35624 was made at the National Collections of Industrial and Marine Bacteria Limited (NCIMB) Ferguson Building, Craibstone Estate, Bucksburn, Aberdeen, AB21 9YA, Scotland, UK on Jan. 13, 1999 and accorded the accession number NCIMB 41003.

A deposit of *Bifidobacteria infantis* strain BL1207 was made at the American Type Culture Collection (ATTC) 10801 University Boulevard, Manassas, Va. 20110-2209, USA on Nov. 14, 2008 and accorded the accession number PTA-9608.

A deposit of *Bifidobacterium longum* strain AH121A was made at the National Collections of Industrial and Marine Bacteria Limited (NCIMB) Ferguson Building, Craibstone Estate, Bucksburn, Aberdeen, AB21 9YA, Scotland, UK on Nov. 5, 2009 and accorded the accession number NCIMB 41675.

A deposit of *Bifidobacterium longum* strain AH1714 was made at the National Collections of Industrial and Marine Bacteria Limited (NCIMB) Ferguson Building, Craibstone Estate, Bucksburn, Aberdeen, AB21 9YA, Scotland, UK on Nov. 5, 2009 and accorded the accession number NCIMB 41676.

Given the size of the isolated polynucleotide it would not be uncommon for a point mutation or some other form of mutation to be present in the sequence. As such we encompass variants of SEQ ID No. 1 in the disclosure. As used herein, the term "variants", means strains of *Bifidobacteria* that have a sequence identity of at least 99.5% or more with SEQ ID No. 1.

SEQ ID No. 1 contains a large number of open reading frames which represent the predicted genes. We have identified 1,836 protein coding regions or genes within this polynucleotide. As such, our disclosure encompasses fragments of the polynucleotide of SEQ ID No. 1. The fragments may correspond to portions of the polynucleotide sequence that encode one or more proteins. Alternatively, the fragments may correspond to portions of the polynucleotide sequence that specify part of a gene or genes for example the fragment may correspond to a portion of the polynucleotide sequence that spans a part of two or more genes.

The sequence of SEQ ID No. 1 is a DNA polynucleotide sequence, our disclosure encompasses sequences that are complementary to the DNA sequence for example complementary DNA (cDNA) or RNA sequences including messenger RNA (mRNA) and transfer RNA (tRNA) or protein sequences such as amino acid sequences encoded by the polynucleotide sequence.

The polynucleotide of SEQ ID No.1 and complementary sequences thereof may take many forms for example an isolated polynucleotide sequence; an isolated protein sequence; a biologically pure culture of a Bifidobacterial strain comprising the nucleic acid of SEQ ID NO. 1; a plasmid comprising the polynucleotide of SEQ ID No. 1; and the like. All of these forms of the sequence of SEQ ID No. 1 are encompassed in this disclosure.

As used herein, the term "expresses an exopolysaccharide", may be interpreted to mean that a bacterial strain contains a DNA sequence encoding an exopolysaccharide for example a DNA sequence that encodes at least one gene from SEQ ID No. 2 and/or at least one gene from SEQ ID No. 3 or a functional fragment or variant thereof.

As used herein, the term "sequence homology" encompasses sequence homology at a nucleic acid and/or an amino acid (protein) level. Sequence homology is indicated as the overall percentage of identity across the nucleic acid and/or amino acid sequence. The sequence homology may be determined using standard techniques known to those skilled in the art. For example sequence homology may be determined using the on-line homology algorithm "BLAST" program, publicly available at. A sequence may have at least 85% or at least 86% or at least 87% or at least 88% or at least 89% or at lest 90% or at least 91% or at least 92% or at least 93% or at least 94% or at least 95% or at least 96% or at least 97% or at least 98% or at least 99% sequence homology with the nucleic acid sequences described herein or the amino acid (protein) encoded thereby.

The present invention is based on the whole genome sequence of *Bifidobacterium longum* biotype infantis UCC 35624. The genome sequence is listed in SEQ ID No. 1 of the attached sequence listing and comprises 2,264374 base pairs. Analysis of the genome sequence identified 1,836 genes having the open reading frames as set out in Table 1 below.

TABLE 1

| GeneID | Start | End | Strand | Description |
| --- | --- | --- | --- | --- |
| BI00001 | 1667321 | 1667608 | − | CRISPR-associated protein Cas2 |
| BI00002 | 1667697 | 1668593 | − | CRISPR-associated protein Cas1 |
| BI00002a | 1668725 | 1669423 | − | CRISPR-associated protein Cas4 |
| BI00003 | 1669465 | 1670313 | − | CRISPR-associated protein, TM1801 family |
| BI00004 | 1670320 | 1672275 | − | CRISPR-associated protein, CT1133 family |
| BI00005 | 1672281 | 1672982 | − | CRISPR-associated protein, CT1134 family |
| BI00006 | 1672992 | 1675427 | − | hypothetical CRISPR-associated helicase Cas3 |
| BI00007 | 1676109 | 1676426 | − | COG3464: Transposase and inactivated derivatives |
| BI00008 | 1677053 | 1680283 | − | isoleucyl-tRNA synthetase |
| BI00009 | 1680955 | 1682163 | + | aminotransferase, class I, putative |
| BI00010 | 1682280 | 1683785 | − | galactoside symporter |
| BI00011 | 1684111 | 1687299 | + | beta-galactosidase, putative |
| BI00012 | 1687365 | 1688372 | − | sugar-binding transcriptional regulator, LacI family, putative |
| BI00013 | 1688522 | 1689889 | − | Putative antibiotic resistance protein (membrane protein) |
| BI00014 | 1690007 | 1690906 | − | hypothetical pfkB family carbohydrate kinase |
| BI00015 | 1690909 | 1692111 | − | alcohol dehydrogenase, iron-containing |
| BI00016 | 1692111 | 1692794 | − | hypothetical haloacid dehalogenase-like hydrolase |
| BI00017 | 1692921 | 1693901 | − | inosine-uridine preferring nucleoside hydrolase |
| BI00018 | 1693960 | 1694913 | − | hypothetical pfkB family carbohydrate kinase |
| BI00019 | 1694909 | 1695553 | − | hypothetical N-(5'phosphoribosyl)anthranilate isomerase |
| BI00020 | 1695603 | 1696415 | − | ABC transporter, ATP-binding protein |
| BI00021 | 1696415 | 1697242 | − | conserved hypothetical protein |
| BI00022 | 1697246 | 1698055 | − | hypothetical Cobalt transport protein |
| BI00023 | 1698062 | 1698712 | − | conserved hypothetical protein |
| BI00024 | 1698969 | 1700846 | + | transcriptional regulator, LacI family/carbohydrate kinase, PfkB family protein |
| BI00026 | 1700977 | 1702989 | − | ABC transporter, ATP-binding/permease protein |
| BI00027 | 1702989 | 1704944 | − | ABC transporter, ATP-binding protein |
| BI00028 | 1704944 | 1705402 | − | transcriptional regulator, MarR family, putative |
| BI00029 | 1705699 | 1706610 | − | COG1472: Beta-glucosidase-related glycosidases |
| BI00030 | 1706029 | 1706937 | + | COG1309: Transcriptional regulator |
| BI00031 | 1707015 | 1708373 | − | unnamed protein product |
| BI00032 | 1708509 | 1710902 | − | xylosidase/arabinosidase [imported] |
| BI00033 | 1710937 | 1711287 | − | hypothetical protein |
| BI00034 | 1711383 | 1712762 | − | glutamate--cysteine ligase, putative |
| BI00035 | 1712905 | 1718037 | + | conserved domain protein |
| BI00036 | 1718044 | 1718883 | + | hypothetical protein |
| BI00037 | 1719052 | 1724187 | − | BadF/BadG/BcrA/BcrD ATPase family family |
| BI00038 | 1724418 | 1725143 | − | anaerobic ribonucleoside-triphosphate reductase activating protein |
| BI00039 | 1725294 | 1727699 | − | anaerobic ribonucleoside-triphosphate reductase |
| BI00040 | 1728167 | 1729534 | + | exodeoxyribonuclease VII, large subunit |
| BI00041 | 1729587 | 1729886 | + | exodeoxyribonuclease VII, small subunit |
| BI00042 | 1730013 | 1730534 | + | NADP(H) oxidoreductase CC0205 [imported] |
| BI00043 | 1730676 | 1732529 | − | long-chain-fatty-acid--CoA ligase, putative |
| BI00044 | 1732662 | 1732787 | − | COG1970: Large-conductance mechanosensitive channel |
| BI00045 | 1732765 | 1733166 | − | hypothetical Large-conductance mechanosensitive channel, MscL |
| BI00046 | 1733337 | 1733762 | − | UNKNOWN PROTEIN, putative |
| BI00047 | 1733887 | 1734102 | − | COG0454: Histone acetyltransferase HPA2 and related acetyltransferases |
| BI00048 | 1734587 | 1735696 | + | hypothetical transmembrane protein with unknown function |
| BI00049 | 1735718 | 1736683 | − | exopolyphosphatase, putative |
| BI00050 | 1736864 | 1737967 | − | aminotransferase, class I |
| BI00051 | 1738178 | 1739230 | + | oxidoreductase, Gfo/Idh/MocA family, putative |
| BI00052 | 1739267 | 1739779 | − | patch repair protein [imported] |
| BI00053 | 1739931 | 1740377 | + | acetyltransferase, GNAT family |
| BI00054 | 1740356 | 1740841 | − | conserved hypothetical protein |
| BI00055 | 1741026 | 1745207 | − | helicase, Snf2 family |
| BI00056 | 1745285 | 1746367 | + | conserved hypothetical protein |
| BI00057 | 1746358 | 1746504 | − | hypothetical protein |
| BI00058 | 1746604 | 1747620 | + | tetrahydrodipicolinate N-succinyltransferase (dapD) |
| BI00059 | 1747840 | 1749129 | − | citrate synthase I |
| BI00060 | 1749406 | 1750242 | − | methionine aminopeptidase, type I |
| BI00061 | 1750378 | 1751355 | − | membrane protein, putative |
| BI00062 | 1751532 | 1753703 | + | belongs to peptidase family M13 |
| BI00063 | 1753792 | 1754526 | − | single-stranded DNA-binding protein (ssb) subfamily |

TABLE 1-continued

Open reading frames of the genome of UCC 35624.

| GeneID | Start | End | Strand | Description |
|---|---|---|---|---|
| BI00064 | 1754805 | 1756616 | − | prolyl-tRNA synthetase |
| BI00065 | 1757008 | 1757361 | + | hypothetical protein |
| BI00066 | 1757392 | 1758561 | − | pflA |
| BI00067 | 1758551 | 1760338 | − | Protein of unknown function family |
| BI00068 | 1760391 | 1761806 | − | TPR domain protein |
| BI00069 | 1761858 | 1762505 | − | oligoribonuclease |
| BI00070 | 1762676 | 1764259 | − | inosine-5'-monophosphate dehydrogenase |
| BI00071 | 1764282 | 1765562 | − | undecaprenyl-phosphate alpha-N-acetylglucosaminyltransferase |
| BI00072 | 1765562 | 1766233 | − | Sua5/YciO/YrdC/YwlC family protein |
| BI00073 | 1766408 | 1767082 | + | maltose O-acetyltransferase |
| BI00074 | 1767220 | 1767921 | − | branched-chain amino acid ABC transporter, ATP-binding protein |
| BI00075 | 1767924 | 1768781 | − | branched chain amino acid ABC transporter, ATP-binding protein |
| BI00076 | 1768781 | 1769854 | − | branched-chain amino acid ABC transporter, permease protein |
| BI00077 | 1769874 | 1770797 | − | branched-chain amino acid ABC transporter, permease protein |
| BI00078 | 1771042 | 1772226 | − | branched-chain amino acid ABC transporter, amino acid-binding protein, putative |
| BI00079 | 1772502 | 1773407 | − | N-methylase PapM |
| BI00080 | 1773473 | 1774492 | − | peptide chain release factor 1 |
| BI00003g | 1774715 | 1774924 | − | ribosomal protein L31 |
| BI00081 | 1775256 | 1776482 | − | transcription regulator ROK family VC2007 [imported], putative |
| BI00082 | 1776702 | 1778219 | + | xylulokinase |
| BI00083 | 1778416 | 1778760 | + | lipoprotein, putative |
| BI00084 | 1778773 | 1779114 | + | hypothetical protein |
| BI00085 | 1779393 | 1779737 | − | possible sugar permease |
| BI00086 | 1779656 | 1780930 | − | transposase, Mutator family |
| BI00087 | 1781199 | 1782545 | − | xylose isomerase |
| BI00088 | 1782842 | 1783072 | + | drug resistance transporter, EmrB/QacA subfamily |
| BI00089 | 1783095 | 1783409 | + | drug resistance transporter, EmrB/QacA subfamily |
| BI00090 | 1783425 | 1784222 | − | conserved hypothetical protein |
| BI00091 | 1785149 | 1785661 | − | polypeptide deformylase |
| BI00092 | 1785576 | 1786421 | − | oxidoreductase, aldo/keto reductase family superfamily |
| BI00093 | 1786497 | 1786673 | − | COG0477: Permeases of the major facilitator superfamily |
| BI00094 | 1786761 | 1787264 | − | hypothetical COG0477: Permeases of the major facilitator superfamily |
| BI00095 | 1787291 | 1787791 | − | possible MarR-type transcriptional regulator |
| BI00011g | 1787998 | 1788333 | − | hypothetical protein Blon02136 |
| BI00096 | 1788358 | 1789572 | − | sugar ABC transporter, permease protein |
| BI00097 | 1789575 | 1791125 | − | sugar ABC transporter, ATP-binding protein |
| BI00098 | 1791229 | 1792383 | − | sugar ABC transporter, periplasmic sugar-binding protein |
| BI00099 | 1792462 | 1792608 | − | hypothetical protein |
| BI00100 | 1792854 | 1793801 | + | probable repressor protein in (NagC/XylR) family |
| BI00101 | 1793842 | 1794705 | + | sugar ABC transporter, ATP-binding protein, putative |
| BI00102 | 1794736 | 1795683 | − | glucokinase, putative |
| BI00103 | 1796537 | 1798192 | + | ATP binding protein of ABC transporter |
| BI00104 | 1798507 | 1799409 | + | acyl-CoA thioesterase II |
| BI00105 | 1799511 | 1800035 | − | hypothetical membrane protein with unknown function |
| BI00106 | 1800213 | 1801622 | − | dihydroneopterin aldolase |
| BI00107 | 1801736 | 1802608 | − | dihydropteroate synthase |
| BI00108 | 1802699 | 1803295 | − | GTP cyclohydrolase I |
| BI00109 | 1803391 | 1805478 | − | cell division protein FtsH |
| BI00110 | 1805478 | 1806038 | − | hypoxanthine phosphoribosyltransferase |
| BI00111 | 1806028 | 1807191 | − | COG0037: Predicted ATPase of the PP-loop superfamily implicated |
| BI00112 | 1807285 | 1808772 | − | D-alanyl-D-alanine carboxypeptidase/D-alanyl-D-alanine-endopeptidase |
| BI00113 | 1808798 | 1810468 | − | hypothetical transmembrane protein with unknown function |
| BI00114 | 1810468 | 1811421 | − | ATP-binding protein of ABC transporter system |
| BI00115 | 1811519 | 1812739 | − | glycosyl transferase domain protein, putative |
| BI00116 | 1812742 | 1814496 | − | hypothetical integral membrane protein in upfo118 |
| BI00117 | 1814587 | 1815252 | + | probable glycosyltransferase |
| BI00118 | 1815481 | 1816629 | − | alcohol dehydrogenase, iron-containing |

TABLE 1-continued

Open reading frames of the genome of UCC 35624.

| GeneID | Start | End | Strand | Description |
| --- | --- | --- | --- | --- |
| BI00119 | 1817069 | 1818370 | + | cyclopropane-fatty-acyl-phospholipid synthase |
| BI00120 | 1818383 | 1819687 | + | hypothetical COG0477: Permeases of the major facilitator superfamily |
| BI00121 | 1820205 | 1821215 | − | UDP-glucose 4-epimerase |
| BI00122 | 1821585 | 1822400 | + | methyltransferase, putative |
| BI00123 | 1822698 | 1823195 | − | hypothetical protein |
| BI00124 | 1823244 | 1823708 | − | Orf2 |
| BI00125 | 1823795 | 1824079 | + | hypothetical Helix-turn-helix |
| BI00126 | 1824492 | 1824788 | − | hypothetical protein |
| BI00127 | 1825086 | 1826453 | − | gp22 |
| BI00128 | 1827148 | 1827699 | − | hypothetical protein |
| BI00170t | 1827699 | 1828901 | − | hypothetical Phage integrase family |
| BI00129 | 1829429 | 1830229 | + | azlC protein, putative |
| BI00130 | 1830229 | 1830558 | + | branched-chain amino acid permease |
| BI00131 | 1830743 | 1831258 | − | phosphotyrosine protein phosphatase, putative |
| BI00132 | 1831385 | 1832044 | − | dihydrofolate reductase |
| BI00133 | 1832157 | 1832936 | − | thymidylate synthase |
| BI00134 | 1833154 | 1833564 | + | conserved hypothetical protein |
| BI00135 | 1833629 | 1834663 | − | demannu, putative |
| BI00136 | 1834835 | 1835572 | − | P60 extracellular protein, invasion associated protein Iap |
| BI00137 | 1835733 | 1836476 | − | NLP/P60 family domain protein |
| BI00138 | 1836692 | 1837645 | − | N-acetylmuramoyl-L-alanine amidase domain protein |
| BI00139 | 1838255 | 1839178 | + | phosphoserine aminotransferase, putative |
| BI00140 | 1839305 | 1839562 | + | conserved hypothetical protein |
| BI00141 | 1839693 | 1840874 | − | sensor histidine kinase, putative |
| BI00142 | 1841128 | 1841745 | + | phosphate transport system regulatory protein PhoU, putative |
| BI00143 | 1842110 | 1842847 | − | phosphoglycerate mutase |
| BI00144 | 1842910 | 1843872 | − | 1,4-dihydroxy-2-naphthoate octaprenyltransferase |
| BI00145 | 1843937 | 1845412 | − | lysyl-tRNA synthetase |
| BI00146 | 1846534 | 1847304 | + | AraJ-like protein probably involved in transport of arabinose polymers |
| BI00147 | 1847394 | 1849754 | + | TPR Domain domain protein |
| BI00148 | 1849833 | 1850462 | + | conserved hypothetical protein |
| BI00149 | 1850618 | 1852216 | − | hypothetical membrane protein possibly involved in transport |
| BI00150 | 1852325 | 1853029 | − | conserved hypothetical protein |
| BI00151 | 1853062 | 1854903 | − | conserved hypothetical protein |
| BI00152 | 1854930 | 1856174 | + | possible histidine kinase sensor of two component system |
| BI00153 | 1856174 | 1856866 | + | transcription regulator, LuxR family NMB1250 [imported] |
| BI00154 | 1856920 | 1857939 | − | UDP-glucose 4-epimerase |
| BI00155 | 1858012 | 1859556 | − | galactose-1-phosphate uridylyltransferase |
| BI00156 | 1859606 | 1860682 | − | putative desulfatase possibly for mucin |
| BI00157 | 1860713 | 1862965 | − | conserved hypothetical protein |
| BI00158 | 1863426 | 1864382 | − | sugar ABC transporter, permease protein |
| BI00159 | 1864382 | 1865278 | − | sugar ABC transporter, permease protein, putative |
| BI00160 | 1865546 | 1866859 | − | solute binding protein of ABC transporter for sugars |
| BI00161 | 1867217 | 1867369 | − | hypothetical protein |
| BI00162 | 1867867 | 1868856 | − | seryl-tRNA synthetase |
| BI00163 | 1869384 | 1870562 | + | Diacylglycerol kinase catalytic domain (presumed) protein |
| BI00164 | 1870573 | 1871409 | − | transcription antiterminator, BglG family, putative |
| BI00165 | 1871430 | 1873829 | − | PTS system component, putative |
| BI00166 | 1874293 | 1875843 | + | major facilitator family transporter CC0814 [imported], putative |
| BI00167 | 1875934 | 1877607 | + | phosphoglucomutase, alpha-D-glucose phosphate-specific |
| BI00222t | 1878343 | 1879437 | − | conserved hypothetical protein |
| BI00168 | 1879668 | 1880087 | + | conserved hypothetical protein |
| BI00169 | 1880224 | 1881837 | + | oxidoreductase, pyridine nucleotide-disulfide, class I |
| BI00170 | 1882002 | 1882151 | − | hypothetical protein |
| BI00171 | 1882305 | 1883360 | + | RNase H |
| BI00172 | 1883494 | 1884189 | + | ribose 5-phosphate isomerase |
| BI00173 | 1884629 | 1885258 | − | conserved hypothetical protein |
| BI00174 | 1885386 | 1886921 | + | DNA repair protein RadA |
| BI00175 | 1886942 | 1888063 | − | riboflavin biosynthesis protein RibF |
| BI00176 | 1888164 | 1889324 | − | tRNA pseudouridine synthase B |
| BI00177 | 1889329 | 1889799 | − | ribosome-binding factor A |
| BI00178 | 1889953 | 1892799 | − | translation initiation factor IF-2 |
| BI00179 | 1893150 | 1894214 | − | N utilization substance protein A |

TABLE 1-continued

Open reading frames of the genome of UCC 35624.

| GeneID | Start | End | Strand | Description |
|---|---|---|---|---|
| BI00180 | 1894422 | 1895147 | + | lipoprotein, putative |
| BI00181 | 1895194 | 1896234 | − | transcriptional regulator, LacI family, putative |
| BI00182 | 1896528 | 1896629 | − | hypothetical protein |
| BI00183 | 1896770 | 1897798 | − | hypothetical |
| BI00184 | 1897936 | 1898568 | − | alpha-L-arabinosidase |
| BI00185 | 1899147 | 1899917 | − | Transglutaminase-like superfamily domain protein |
| BI00186 | 1900154 | 1902331 | − | Domain of unknown function (DUF404) family |
| BI00187 | 1902473 | 1902586 | − | hypothetical protein |
| BI00188 | 1902727 | 1903515 | + | tRNA pseudouridine synthase A |
| BI00189 | 1903603 | 1904142 | − | ribosomal protein L17 |
| BI00190 | 1904245 | 1905237 | − | RNA polymerases L/13 to 16 kDa subunit |
| BI00191 | 1905321 | 1905716 | − | ribosomal protein S11 |
| BI00192 | 1905807 | 1906181 | − | ribosomal protein S13p/S18e |
| BI00193 | 1906333 | 1906443 | − | ribosomal protein L36 |
| BI00194 | 1906470 | 1906685 | − | translation initiation factor IF-1 |
| BI00195 | 1906865 | 1907422 | − | adenylate kinase |
| BI00196 | 1907595 | 1908722 | − | preprotein translocase, SecY subunit |
| BI00197 | 1909207 | 1909656 | − | ribosomal protein L15 |
| BI00198 | 1909662 | 1909844 | − | ribosomal protein L30 |
| BI00199 | 1909853 | 1910581 | − | ribosomal protein S5 |
| BI00200 | 1910581 | 1910991 | − | ribosomal protein L18 |
| BI00201 | 1910954 | 1911490 | − | ribosomal protein L6 |
| BI00202 | 1911511 | 1911906 | − | ribosomal protein S8 |
| BI00203 | 1911999 | 1912181 | − | ribosomal protein S14p/S29e |
| BI00204 | 1912186 | 1912755 | − | ribosomal protein L5 VC2584 [imported] |
| BI00205 | 1912755 | 1913087 | − | ribosomal protein L24 |
| BI00206 | 1913092 | 1913457 | − | ribosomal protein L14 |
| BI00207 | 1913555 | 1913812 | − | ribosomal protein S17 |
| BI00208 | 1913818 | 1914066 | − | ribosomal protein L29 |
| BI00209 | 1914069 | 1914485 | − | ribosomal protein L16 |
| BI00210 | 1914495 | 1915295 | − | ribosomal protein S3 |
| BI00211 | 1915301 | 1915657 | − | ribosomal protein L22 |
| BI00212 | 1915677 | 1915952 | − | ribosomal protein S19 |
| BI00213 | 1915971 | 1916798 | − | ribosomal protein L2 |
| BI00214 | 1916838 | 1917131 | − | ribosomal protein L23 |
| BI00215 | 1917140 | 1917793 | − | ribosomal protein L4/L1 family |
| BI00216 | 1917803 | 1918441 | − | ribosomal protein L3 |
| BI00217 | 1918461 | 1918766 | − | ribosomal protein S10 |
| BI00218 | 1919023 | 1920027 | + | membrane protein, putative |
| BI00219 | 1920366 | 1923092 | − | Unknown |
| BI00220 | 1923607 | 1924797 | + | probable repressor in the Rok (NagC/XylR) family |
| BI00221 | 1924797 | 1927334 | + | glycogen operon protein GlgX |
| BI00222 | 1927431 | 1927919 | − | ribosomal protein S9 |
| BI00223 | 1927945 | 1928391 | − | ribosomal protein L13 |
| BI00224 | 1928792 | 1930954 | − | 4-alpha-glucanotransferase |
| BI00225 | 1931125 | 1931931 | − | hypothetical Leucine rich repeat variant |
| BI00226 | 1931876 | 1932514 | − | conserved hypothetical protein TIGR00257 |
| BI00227 | 1932579 | 1933592 | − | possible 2-hydroxyacid dehydrogenase |
| BI00228 | 1933669 | 1935009 | − | capA protein, putative |
| BI00229 | 1935547 | 1936608 | − | COG0697: Permeases of the drug/metabolite transporter (DMT) superfamily |
| BI00230 | 1936648 | 1937991 | + | DNA-damage-inducible protein P |
| BI00231 | 1938024 | 1939256 | − | aminotransferase, putative |
| BI00232 | 1939374 | 1939691 | − | fdxC |
| BI00233 | 1939755 | 1941278 | − | possible cationic amino acid transporter |
| BI00234 | 1941433 | 1942398 | − | UDP-N-acetylenolpyruvoylglucosamine reductase |
| BI00235 | 1942930 | 1943094 | − | ribosomal protein L33 |
| BI00236 | 1943529 | 1944245 | + | possible cystathionine gamma lyase |
| BI00237 | 1944924 | 1945214 | − | chaperonin, 10 kDa |
| BI00238 | 1945390 | 1946604 | − | conserved hypothetical protein |
| BI00239 | 1946895 | 1947557 | − | rimJ |
| BI00240 | 1947644 | 1948360 | + | 5-formyltetrahydrofolate cyclo-ligase-related protein |
| BI00241 | 1948527 | 1948709 | + | conserved hypothetical protein |
| BI00242 | 1948950 | 1949516 | + | conserved hypothetical protein |
| BI00243 | 1949617 | 1949814 | − | hypothetical protein Blon021580 |
| BI00244 | 1949820 | 1953440 | − | conserved hypothetical protein |
| BI00245 | 1953452 | 1954999 | − | conserved hypothetical protein |
| BI00246 | 1955200 | 1955577 | − | ribosomal protein L7/L12 |
| BI00247 | 1955689 | 1956207 | − | ribosomal protein L10 |
| BI00248 | 1956479 | 1957222 | − | conserved hypothetical protein |
| BI00249 | 1957561 | 1958952 | + | Unknown |
| BI00250 | 1959385 | 1962123 | − | polyribonucleotide nucleotidyltransferase |
| BI00251 | 1962444 | 1962710 | − | ribosomal protein S15 |

TABLE 1-continued

Open reading frames of the genome of UCC 35624.

| GeneID | Start | End | Strand | Description |
|---|---|---|---|---|
| BI00252 | 1962882 | 1963562 | − | conserved hypothetical protein |
| BI00253 | 1963721 | 1963951 | − | hypothetical protein |
| BI00254 | 1964091 | 1966964 | − | possible extracellular exo-xylanase |
| BI00255 | 1967190 | 1969712 | − | endo-1,4-beta-xylanase D |
| BI00256 | 1970329 | 1971432 | + | IS30 family, transposase [imported] |
| BI00257 | 1971591 | 1972274 | − | conserved hypothetical protein |
| BI00334t | 1972174 | 1972389 | + | conserved hypothetical protein |
| BI00258 | 1972411 | 1973094 | − | hypothetical protein Blon021028 |
| BI00259 | 1973553 | 1974914 | − | possible cell surface protein |
| BI00260 | 1974994 | 1977351 | − | von Willebrand factor type A domain protein |
| BI00261 | 1978150 | 1978326 | − | hypothetical protein Blon021305 |
| BI00262 | 1978353 | 1978820 | − | phosphopantethiene protein transferase |
| BI00263 | 1979459 | 1988974 | − | MaoC like domain protein |
| BI00264 | 1989016 | 1990635 | − | propionyl-CoA carboxylase, beta chain |
| BI00265 | 1990631 | 1992514 | − | accA3 |
| BI00266 | 1993105 | 1993701 | + | bioY protein |
| BI00267 | 1993739 | 1994710 | − | biotin--acetyl-CoA-carboxylase ligase |
| BI00268 | 1994853 | 1996895 | + | membrane protein, putative |
| BI00269 | 1996904 | 1997731 | + | conserved hypothetical protein |
| BI00270 | 1997829 | 1998524 | − | transcriptional regulator, putative |
| BI00350t | 1998629 | 1999459 | − | hypothetical transcriptional regulator, IclR family |
| BI00271 | 2011598 | 2011726 | − | hypothetical protein |
| BI00272 | 2011797 | 2012486 | − | ribosomal protein L1 |
| BI00273 | 2012505 | 2012933 | − | ribosomal protein L11 |
| BI00274 | 2013199 | 2014089 | − | transcription termination/antitermination factor NusG |
| BI00275 | 2014122 | 2014346 | − | preprotein translocase SecE subunit |
| BI00276 | 2014593 | 2015795 | − | aspartate aminotransferase [imported] |
| BI00277 | 2015889 | 2016986 | − | glutamate 5-kinase |
| BI00278 | 2017023 | 2018711 | − | GTP-binding protein |
| BI00279 | 2018783 | 2019028 | − | ribosomal protein L27 |
| BI00280 | 2019054 | 2019359 | − | ribosomal protein L21 |
| BI00281 | 2019502 | 2022534 | − | hypothetical ribonuclease, Rne/Rng family |
| BI00282 | 2022850 | 2024121 | − | succinyl-diaminopimelate desuccinylase |
| BI00283 | 2024159 | 2025100 | + | transporter, putative |
| BI00284 | 2025282 | 2026727 | − | permease, putative domain protein |
| BI00285 | 2026727 | 2027818 | − | ABC transporter, ATP-binding protein |
| BI00286 | 2027996 | 2029441 | − | Maf-like protein |
| BI00287 | 2029581 | 2030690 | − | homoserine kinase |
| BI00288 | 2030800 | 2032113 | − | homoserine dehydrogenase |
| BI00289 | 2032276 | 2033865 | − | diaminopimelate decarboxylase |
| BI00290 | 2033871 | 2035541 | − | arginyl-tRNA synthetase |
| BI00291 | 2035944 | 2036606 | + | possible TetR-type transcriptional regulator |
| BI00292 | 2036606 | 2037880 | + | permease, putative |
| BI00293 | 2037742 | 2038899 | + | transcription regulator LysR family VC1588 [imported], putative |
| BI00294 | 2038996 | 2040246 | + | probable aminotransferase |
| BI00295 | 2040298 | 2041521 | − | UDP-N-acetylglucosamine 1-carboxyvinyltransferase |
| BI00296 | 2041869 | 2043212 | + | NADH oxidase |
| BI00297 | 2043424 | 2044548 | − | dihydroorotate dehydrogenase family protein, putative |
| BI00298 | 2044591 | 2046468 | − | CAAX amino terminal protease family protein family |
| BI00299 | 2046594 | 2047283 | − | 3-isopropylmalate dehydratase small subunit |
| BI00300 | 2047369 | 2048769 | − | 3-isopropylmalate dehydratase, large subunit |
| BI00301 | 2049087 | 2049860 | + | transcriptional regulator, IclR family |
| BI00302 | 2050021 | 2051391 | − | Ser/Thr protein phosphatase family |
| BI00303 | 2051896 | 2054130 | + | polyphosphate kinase |
| BI00304 | 2054291 | 2055487 | + | mutT1 |
| BI00305 | 2055480 | 2056298 | + | hypothetical protein Blon021115 |
| BI00306 | 2056564 | 2057871 | − | conserved hypothetical protein |
| BI00307 | 2057963 | 2058121 | − | hypothetical protein |
| BI00308 | 2058175 | 2058813 | + | uracil phosphoribosyltransferase |
| BI00309 | 2058864 | 2059340 | + | conserved hypothetical protein TIGR00246 |
| BI00310 | 2059542 | 2060648 | − | possible phosphodiesterase |
| BI00311 | 2060677 | 2061747 | − | glutamyl-tRNA synthetase domain protein |
| BI00312 | 2061933 | 2064599 | − | ATP-dependent Clp protease, ATP-binding subunit ClpB |
| BI00313 | 2064821 | 2066371 | − | histidine ammonia-lyase |
| BI00314 | 2066617 | 2067489 | + | transcriptional regulator, IclR family, putative |
| BI00315 | 2067489 | 2067662 | + | conserved hypothetical protein |
| BI00316 | 2067741 | 2068559 | − | possible 2-hydroxyhepta-2,4-diene-1,7-dioate isomerase in the fumarylacetoacetate hydrolase family |

TABLE 1-continued

Open reading frames of the genome of UCC 35624.

| GeneID | Start | End | Strand | Description |
|---|---|---|---|---|
| BI00317 | 2068665 | 2069873 | − | hypothetical membrane protein with unknown function |
| BI00318 | 2070097 | 2071272 | − | UDP-galactopyranose mutase |
| BI00319 | 2071426 | 2072670 | + | dTDP-glucose 4,6-dehydratase |
| BI00320 | 2072827 | 2074311 | + | conserved hypothetical protein |
| BI00321 | 2074367 | 2075068 | + | conserved hypothetical protein |
| BI00423t | 2075382 | 2075687 | + | putative transposase |
| BI00322 | 2075763 | 2076530 | − | IS1533, OrfB |
| BI00323 | 2076530 | 2077987 | − | transposase (25) BH3998 [imported], putative |
| BI00324 | 2078280 | 2078996 | − | glycosyltransferase, putative |
| BI00325 | 2079313 | 2079666 | − | sialic acid-specific 9-O-acetylesterase |
| BI00326 | 2080049 | 2081173 | + | hypothetical Acyltransferase family |
| BI00327 | 2081181 | 2082893 | − | hypothetical membrane protein with unknown function |
| BI00328 | 2082902 | 2085811 | − | hypothetical Glycosyl transferase family 8 |
| BI00329 | 2085935 | 2087170 | − | hypothetical glycosyl transferase, group 2 family protein |
| BI00330 | 2087259 | 2088509 | − | polysaccharide ABC transporter, ATP-binding protein |
| BI00331 | 2088515 | 2089351 | − | polysaccharide ABC transporter, permease protein, putative |
| BI00332 | 2089580 | 2091367 | + | hypothetical Glycosyl transferase family 8 |
| BI00333 | 2091457 | 2092698 | − | UDP-glucose 6-dehydrogenase |
| BI00334 | 2092974 | 2093636 | + | hypothetical NAD dependent epimerase/dehydratase family |
| BI00335 | 2093654 | 2094844 | − | membrane protein, putative |
| BI00336 | 2094847 | 2097099 | − | conserved hypothetical protein |
| BI00337 | 2097441 | 2098844 | + | hypothetical membrane protein with unknown function |
| BI00338 | 2098844 | 2099962 | + | possible ATP binding protein of ABC transporter |
| BI00339 | 2100089 | 2100790 | + | HDIG domain protein |
| BI00340 | 2100871 | 2101728 | − | conserved hypothetical protein |
| BI00341 | 2101825 | 2104335 | − | Kup system potassium uptake protein [imported] |
| BI00342 | 2104481 | 2105188 | − | hydrolase, TatD family |
| BI00343 | 2105717 | 2106784 | + | Fic protein family family |
| BI00344 | 2106816 | 2108621 | − | ABC transporter, ATP-binding/permease protein |
| BI00345 | 2108635 | 2110542 | − | ABC transporter, ATP-binding/permease protein |
| BI00346 | 2110935 | 2111099 | − | hypothetical protein |
| BI00347 | 2111297 | 2112703 | − | possible alpha-galactosidase |
| BI00348 | 2113077 | 2114231 | + | transcriptional regulator, LacI family, putative |
| BI00349 | 2114409 | 2115356 | − | probable AraC/XylS-type transcriptional regulator |
| BI00350 | 2115401 | 2117626 | − | conserved hypothetical protein |
| BI00351 | 2117851 | 2119374 | + | aminopeptidase C |
| BI00352 | 2119555 | 2120628 | + | conserved hypothetical protein |
| BI00353 | 2121673 | 2123403 | − | methionyl-tRNA synthetase |
| BI00354 | 2123873 | 2124496 | + | conserved hypothetical protein |
| BI00466t | 2124496 | 2124864 | + | conserved hypothetical protein |
| BI00355 | 2124897 | 2125922 | − | conserved hypothetical protein TIGR00096 |
| BI00356 | 2126487 | 2127902 | − | possible symporter |
| BI00357 | 2127864 | 2129027 | + | conserved hypothetical protein |
| BI00358 | 2129186 | 2131012 | − | ABC transporter, ATP-binding/permease protein |
| BI00359 | 2131231 | 2133099 | − | ABC transporter, ATP-binding/permease protein |
| BI00360 | 2133289 | 2133684 | − | transcriptional regulator, MarR family, putative |
| BI00475t | 2134267 | 2134506 | + | DNA-damage-inducible protein of Escherichia coli |
| BI00361 | 2135008 | 2138841 | − | LPXTG-motif cell wall anchor domain protein |
| BI00362 | 2139056 | 2139151 | − | hypothetical protein |
| BI00363 | 2139209 | 2143594 | − | secreted protein |
| BI00364 | 2143901 | 2145394 | − | ATP-dependent DNA helicase recG |
| BI00365 | 2145737 | 2147257 | − | amino acid permease |
| BI00366 | 2147448 | 2151185 | − | permease, putative |
| BI00367 | 2151199 | 2151897 | − | ABC transporter, ATP-binding protein |
| BI00368 | 2152041 | 2152607 | + | probable TetR-like transcriptional regulator |
| BI00369 | 2152832 | 2154310 | + | aromatic amino acid transport protein AroP |
| BI00370 | 2154575 | 2155774 | + | putative invertase/transposase |
| BI00371 | 2155961 | 2160952 | − | hypothetical Glycosyl hydrolases family 43 |
| BI00372 | 2161359 | 2164649 | − | hypothetical |
| BI00373 | 2164997 | 2168173 | − | possible arabinosidase |
| BI00374 | 2168529 | 2169131 | − | conserved hypothetical protein |
| BI00375 | 2169340 | 2170179 | − | sugar ABC transporter, permease protein, putative |
| BI00376 | 2170182 | 2171033 | − | sugar ABC transporter, permease protein, putative |
| BI00377 | 2171416 | 2172429 | + | transcription regulator, LacI family [imported], putative |
| BI00378 | 2172690 | 2174015 | − | possible solute binding protein of ABC transporter |

TABLE 1-continued

Open reading frames of the genome of UCC 35624.

| GeneID | Start | End | Strand | Description |
|---|---|---|---|---|
| BI00379 | 2174424 | 2175134 | − | phosphoglycerate mutase family protein |
| BI00380 | 2175226 | 2175600 | + | hypothetical COG0531: Amino acid transporters |
| BI00381 | 2175612 | 2176550 | + | hypothetical nitroreductase family protein |
| BI00382 | 2176846 | 2179572 | + | phage infectio, putative |
| BI00383 | 2179572 | 2181908 | + | phage infection protein, putative |
| BI00384 | 2188511 | 2189263 | + | regulatory protein, SIR2 family |
| BI00385 | 2189415 | 2190791 | − | threonine dehydratase |
| BI00386 | 2190928 | 2192745 | − | glucan 1,6-alpha-glucosidase |
| BI00387 | 2192872 | 2194731 | − | hypothetical Raffinose synthase or seed imbibition protein Sip1 |
| BI00388 | 2194766 | 2196433 | − | alpha-amylase family protein |
| BI00389 | 2196537 | 2197358 | − | hypothetical abc transporter permease protein yurm. {bacillus |
| BI00390 | 2197364 | 2198383 | − | hypothetical Binding-protein-dependent transport systems inner membrane component |
| BI00391 | 2198408 | 2199730 | − | hypothetical Bacterial extracellular solute-binding protein |
| BI00392 | 2199980 | 2201095 | − | hypothetical protein Efae022644 |
| BI00393 | 2201159 | 2202484 | − | hypothetical Bacterial extracellular solute-binding protein |
| BI00394 | 2202692 | 2203717 | + | transcription regulator, LacI family [imported], putative |
| BI00395 | 2203838 | 2204854 | + | transcription regulator, LacI family [imported], putative |
| BI00396 | 2204919 | 2205782 | − | sugar ABC transporter, permease protein |
| BI00397 | 2205804 | 2206730 | − | sugar ABC transporter, permease protein |
| BI00398 | 2206755 | 2208041 | − | sugar ABC transporter, sugar-binding protein, putative |
| BI00399 | 2208215 | 2209420 | + | transcription regulator ROK family VC2007 [imported], putative |
| BI00400 | 2209591 | 2211894 | − | alpha-galactosidase |
| BI00401 | 2212017 | 2212445 | − | hypothetical Cytidine and deoxycytidylate deaminase zinc-binding region |
| BI00402 | 2212589 | 2214658 | + | Na+/H+ antiporter |
| BI00403 | 2214858 | 2215613 | − | serine esterase, putative |
| BI00404 | 2215613 | 2215714 | − | hypothetical protein |
| BI00405 | 2215735 | 2216592 | − | conserved hypothetical protein |
| BI00406 | 2216949 | 2217527 | + | deoxycytidine triphosphate deaminase |
| BI00407 | 2217593 | 2219320 | + | cell wall surface anchor family protein, putative |
| BI00408 | 2219543 | 2222527 | − | calcium E1-E2-type ATPase |
| BI00409 | 2222713 | 2223447 | − | protein probably involved in xylan degradation, possible xylan esterase |
| BI00410 | 2223622 | 2225049 | − | hypothetical major facilitator superfamily protein |
| BI00411 | 2225005 | 2225994 | + | RNA methyltransferase, TrmH family, group 3 |
| BI00412 | 2226107 | 2227516 | − | conserved hypothetical protein |
| BI00413 | 2227740 | 2228864 | − | ATP binding protein of ABC transporter for sugars |
| BI00414 | 2229226 | 2230419 | − | glycosyl transferase domain protein |
| BI00415 | 2230486 | 2231475 | − | Ribonucleotide reductase, beta subunit |
| BI00416 | 2231704 | 2233896 | − | ribonucleoside-diphosphate reductase, alpha subunit |
| BI00417 | 2234015 | 2234470 | − | nrdI protein |
| BI00418 | 2234470 | 2234733 | − | COG0695: Glutaredoxin and related proteins |
| BI00419 | 2235324 | 2235767 | − | hypothetical Helix-turn-helix |
| BI00420 | 2235958 | 2236635 | − | conserved hypothetical protein |
| BI00421 | 2236828 | 2237592 | + | ion transporter |
| BI00422 | 2237788 | 2238891 | + | conserved hypothetical protein |
| BI00423 | 2239035 | 2239349 | − | beta-glucosidase-related glycosidase |
| BI00424 | 2239828 | 2241951 | + | widely conserved protein with eukaryotic protein kinase domain |
| BI00425 | 2242132 | 2243106 | + | conserved hypothetical protein |
| BI00426 | 2243627 | 2245111 | + | conserved hypothetical protein |
| BI00427 | 2245147 | 2246067 | + | dimethyladenosine transferase |
| BI00428 | 2246067 | 2247014 | + | kinase, GHMP family, group 2 |
| BI00429 | 2246860 | 2247690 | + | hypothetical protein BL0655 |
| BI00430 | 2247781 | 2249193 | − | pcnA |
| BI00431 | 2249280 | 2250569 | + | NUDIX domain protein |
| BI00432 | 2250569 | 2252836 | + | cell wall surface anchor family protein, putative |
| BI00433 | 2252836 | 2254560 | + | conserved hypothetical membrane protein in MviN family |
| BI00434 | 2254646 | 2256706 | + | conserved hypothetical protein |
| BI00435 | 2256829 | 2257845 | + | thioredoxin reductase |
| BI00436 | 2258158 | 2259516 | − | chromosome partitioning protein ParB |
| BI00437 | 2259519 | 2260487 | − | Soj family protein |
| BI00438 | 2260741 | 2261403 | − | methyltransferase GidB |
| BI00439 | 2261558 | 2262088 | − | R3H domain protein |

TABLE 1-continued

Open reading frames of the genome of UCC 35624.

| GeneID | Start | End | Strand | Description |
|---|---|---|---|---|
| BI00440 | 2262215 | 2263219 | − | inner membrane protein, 60 kDa VC0004 [imported] |
| BI00143g | 2263219 | 2263533 | − | conserved hypothetical protein TIGR00278 |
| BI00576t | 2263533 | 2264063 | − | ribonuclease P protein component |
| BI00441 | 2263925 | 2264056 | − | ribosomal protein L34 |
| BI00442 | 1 | 1500 | + | chromosomal replication initiator protein DnaA |
| BI00443 | 2239 | 3360 | + | DNA polymerase III, beta subunit |
| BI00444 | 3442 | 4626 | + | recF protein |
| BI00445 | 4626 | 5093 | + | conserved hypothetical protein |
| BI00446 | 5229 | 7364 | + | DNA gyrase, B subunit |
| BI00447 | 7534 | 10083 | + | DNA gyrase, A subunit |
| BI00448 | 10156 | 10719 | + | conserved hypothetical protein |
| BI00449 | 11406 | 12116 | + | hypothetical protein |
| BI00450 | 12179 | 13699 | + | hypothetical Pectinesterase |
| BI00451 | 14103 | 15446 | − | NADP-specific glutamate dehydrogenase |
| BI00452 | 15768 | 16199 | − | AsnC-type transcriptional regulator |
| BI00453 | 16405 | 17736 | + | aspartate aminotransferase |
| BI00454 | 17757 | 18746 | − | hypothetical protein Blon021073 |
| BI00455 | 19007 | 19600 | + | hypothetical protein BL0627 |
| BI00456 | 19770 | 20462 | + | hypothetical protein Blon021075 |
| BI00457 | 20579 | 20821 | + | Putative acrab operon repressor transcription regulator protein |
| BI00599t | 21403 | 21735 | − | IS1557, transposase, putative |
| BI00146g | 21834 | 22397 | − | conserved hypothetical protein |
| BI00458 | 22130 | 23497 | − | hypothetical COG1167: Transcriptional regulators containing a DNA-binding HTH domain and an aminotransferase domain (MocR family) and their eukaryotic orthologs |
| BI00459 | 24132 | 25454 | + | aminotransferase, class III superfamily |
| BI00460 | 25495 | 26397 | + | Zinc metalloprotease |
| BI00461 | 26414 | 26509 | − | hypothetical protein |
| BI00462 | 26487 | 26849 | + | COG3265: Gluconate kinase |
| BI00463 | 27114 | 28424 | − | conserved hypothetical protein |
| BI00464 | 28662 | 29138 | − | Dps family protein, putative |
| BI00465 | 29238 | 30608 | − | CBS domain protein, putative |
| BI00466 | 30841 | 31521 | − | Prokaryotic-type carbonic anhydrases |
| BI00467 | 31727 | 32287 | + | alkyl hydrogen peroxide reductase |
| BI00468 | 32458 | 34371 | + | thioredoxin reductase |
| BI00469 | 34494 | 35963 | − | oxalate: formate antiporter |
| BI00470 | 35948 | 36094 | + | hypothetical protein |
| BI00471 | 36333 | 37328 | + | LacI-type transcriptional regulator |
| BI00472 | 37558 | 40308 | − | phosphoenolpyruvate carboxylase |
| BI00473 | 40594 | 42471 | + | membrane protein, putative |
| BI00474 | 42737 | 44344 | + | possible sodium/proline symporter |
| BI00475 | 44680 | 45663 | − | narrowly conserved hypothetical protein |
| BI00476 | 45917 | 47533 | + | conserved hypothetical protein |
| BI00477 | 47717 | 48805 | − | tryptophanyl-tRNA synthetase |
| BI00478 | 49056 | 49325 | + | hypothetical protein |
| BI00479 | 49437 | 49967 | − | conserved hypothetical protein |
| BI00480 | 49986 | 52505 | + | glycogen phosphorylase |
| BI00481 | 52725 | 52940 | − | hypothetical protein BL0595 |
| BI00482 | 53195 | 53887 | + | Rhomboid family protein |
| BI00483 | 54562 | 55029 | − | conserved hypothetical protein |
| BI00484 | 55119 | 55907 | + | conserved hypothetical protein |
| BI00485 | 55907 | 57142 | + | hypothetical transmembrane protein with unknown function |
| BI00486 | 57196 | 57837 | + | pabA |
| BI00487 | 58067 | 60136 | − | serine/threonine protein kinase |
| BI00488 | 60136 | 60942 | − | serine/threonine protein kinase |
| BI00489 | 61083 | 62546 | − | pbpA |
| BI00490 | 62546 | 64204 | − | Unknown, putative |
| BI00491 | 64204 | 65895 | − | possible phosphoprotein phosphatase |
| BI00492 | 65903 | 66430 | − | FHA-domain-containing proteins |
| BI00493 | 66463 | 67161 | − | FHA domain protein |
| BI00494 | 67349 | 69790 | − | dipeptidyl peptidase IV, putative |
| BI00495 | 69951 | 70997 | + | lysophospholipase L2, putative |
| BI00496 | 71080 | 72228 | + | von Willebrand factor type A domain protein |
| BI00497 | 72231 | 72947 | + | conserved hypothetical protein |
| BI00498 | 72947 | 73348 | + | hypothetical protein Blon021556 |
| BI00654t | 73348 | 73497 | + | hypothetical protein Blon021556 |
| BI00499 | 73873 | 74724 | + | tellurite resistance protein |
| BI00500 | 75108 | 75608 | + | heat shock protein, Hsp20 family |
| BI00501 | 75938 | 76891 | + | Probable transmembrane protein |
| BI00502 | 77065 | 77520 | − | conserved hypothetical protein |
| BI00503 | 77753 | 79132 | + | COG0627: Predicted esterase |
| BI00504 | 79132 | 81702 | + | COG2898: Uncharacterized BCR |

TABLE 1-continued

Open reading frames of the genome of UCC 35624.

| GeneID | Start | End | Strand | Description |
|---|---|---|---|---|
| BI00505 | 82241 | 83212 | + | peptide methionine sulfoxide reductase |
| BI00506 | 83218 | 83304 | + | hypothetical protein BL0567 |
| BI00668t | 83341 | 83496 | + | COG0463: Glycosyltransferases involved in cell wall biogenesis |
| BI00507 | 83506 | 86709 | − | helicase-related protein |
| BI00509 | 86785 | 87195 | − | mutator MutT protein, putative |
| BI00510 | 87337 | 88587 | + | hypothetical Domain of unknown function |
| BI00511 | 88678 | 89139 | + | acetyltransferase, GNAT family family |
| BI00512 | 89226 | 90080 | − | hypothetical |
| BI00513 | 90187 | 90420 | − | hypothetical protein |
| BI00514 | 90480 | 90842 | + | conserved hypothetical protein |
| BI00515 | 91329 | 92639 | − | queuine tRNA-ribosyltransferase |
| BI00516 | 93056 | 95065 | + | heat shock protein HtrA |
| BI00517 | 95480 | 97636 | + | cation-transporting ATPase, E1-E2 family |
| BI00684t | 97816 | 98862 | + | transcriptional regulator, LacI family |
| BI00518 | 98874 | 99131 | − | hypothetical mttA/Hcf106 family |
| BI00519 | 99136 | 100215 | − | Sec-independent protein translocase TatC |
| BI00687t | 100215 | 100730 | − | hypothetical twin-arginine translocation protein, TatA/E family |
| BI00520 | 101182 | 103581 | + | hypothetical Tat (twin-arginine translocation) pathway signal sequence |
| BI00521 | 103674 | 106151 | + | hypothetical |
| BI00522 | 106547 | 107707 | − | conserved hypothetical protein |
| BI00523 | 107911 | 109359 | + | ferredoxin/ferredoxin--NADP reductase, putative |
| BI00524 | 109452 | 110450 | + | heat shock protein HtpX |
| BI00525 | 110667 | 111731 | − | fructose-bisphosphate aldolase, class II |
| BI00526 | 111947 | 113230 | + | adenylosuccinate synthetase |
| BI00527 | 113524 | 114837 | + | chloride channel |
| BI00528 | 115027 | 116094 | + | CrcB-like protein family |
| BI00700t | 116097 | 116489 | + | protein with similarity to CrcB |
| BI00529 | 116581 | 116691 | + | hypothetical protein |
| BI00530 | 116767 | 117849 | + | sugar-binding transcriptional regulator, LacI family, putative |
| BI00531 | 118274 | 119842 | + | Kup system potassium uptake protein [imported] |
| BI00532 | 120262 | 121806 | + | alpha-L-arabinofuranosidase |
| BI00533 | 121981 | 123012 | + | transcription regulator, LacI family [imported], putative |
| BI00534 | 123104 | 124012 | − | glycosyl hydrolase, family 31 |
| BI00535 | 124149 | 124370 | − | IS861, transposase OrfB |
| BI00711t | 124604 | 125803 | + | probable integrase/recombinase |
| BI00712t | 125878 | 126765 | + | probable integrase/recombinase |
| BI00536 | 126765 | 127817 | + | integrase/recombinase XerC, probable [imported], putative |
| BI00537 | 127910 | 128956 | − | IS3 family transposase |
| BI00538 | 129291 | 130814 | + | sucrose phosphorylase |
| BI00539 | 131035 | 132669 | + | hypothetical transmembrane protein with unknown function |
| BI00540 | 132736 | 133776 | + | sugar-binding transcriptional regulator, LacI family, putative |
| BI00541 | 134407 | 135771 | + | major facilitator family transporter |
| BI00542 | 135971 | 137020 | + | ketol-acid reductoisomerase |
| BI00543 | 137452 | 138501 | + | ketol-acid reductoisomerase |
| BI00544 | 138689 | 140500 | − | alpha-amylase family protein |
| BI00545 | 140663 | 141694 | − | transcription regulator, LacI family [imported], putative |
| BI00546 | 142008 | 144242 | − | 4-alpha-glucanotransferase |
| BI00547 | 144506 | 144784 | − | hypothetical protein Blon021648 |
| BI00548 | 144856 | 145482 | + | conserved hypothetical protein |
| BI00549 | 145500 | 146507 | − | transcription regulator, LacI family [imported], putative |
| BI00550 | 146777 | 147490 | + | sugar ABC transporter, permease protein |
| BI00551 | 147605 | 150139 | + | glycosyl hydrolase, family 31 |
| BI00552 | 151125 | 153002 | + | dnaK protein |
| BI00553 | 153005 | 153658 | + | co-chaperone GrpE |
| BI00554 | 153753 | 154769 | + | DnaJ protein [imported] |
| BI00555 | 154787 | 155371 | + | hspR |
| BI00556 | 155647 | 156996 | + | xanthine permease, putative |
| BI00557 | 157036 | 158154 | + | possible acyl protein synthase/acyl-CoA reductase-like protein |
| BI00558 | 158144 | 159640 | + | possible acyl-CoA reductase |
| BI00559 | 159715 | 160497 | + | 3-oxoacyl-acyl carrier protein reductase |
| BI00560 | 160553 | 161281 | + | beta-phosphoglucomutase, putative |
| BI00561 | 161435 | 162157 | + | DedA protein |
| BI00749t | 162383 | 163330 | + | conserved hypothetical protein |
| BI00562 | 163340 | 164404 | + | trbB |
| BI00751t | 164410 | 165060 | + | conserved hypothetical protein |

TABLE 1-continued

Open reading frames of the genome of UCC 35624.

| GeneID | Start | End | Strand | Description |
|---|---|---|---|---|
| BI00752t | 165060 | 165659 | + | hypothetical membrane protein with unknown function |
| BI00563 | 165947 | 166231 | + | hypothetical protein BL0505 |
| BI00754t | 166240 | 166614 | + | conserved hypothetical protein |
| BI00564 | 166715 | 167041 | + | conserved hypothetical protein |
| BI00565 | 167093 | 168220 | + | BmrU protein, putative |
| BI00566 | 168424 | 169020 | − | possible TetR-type transcriptional regulator |
| BI00567 | 169297 | 172125 | + | DNA polymerase III, tau/gamma subunit |
| BI00568 | 172154 | 172753 | + | recombination protein RecR |
| BI00569 | 172756 | 173886 | − | sortase family protein |
| BI00570 | 174774 | 176054 | + | conserved hypothetical protein |
| BI00571 | 176649 | 177179 | + | hypothetical Amino acid kinase family |
| BI00572 | 177262 | 177801 | + | aspartokinase, alpha and beta subunits |
| BI00573 | 177889 | 178980 | − | aspartate-semialdehyde dehydrogenase |
| BI00574 | 179055 | 179765 | + | conserved hypothetical protein |
| BI00575 | 179774 | 181351 | − | Ser/Thr protein phosphatase family |
| BI00576 | 182040 | 183953 | + | 2-isopropylmalate synthase |
| BI00577 | 184031 | 186493 | − | penicillin-binding protein, putative |
| BI00578 | 186772 | 187959 | + | possible pre-pilin peptidase |
| BI00579 | 188086 | 191169 | + | DNA topoisomerase I |
| BI00580 | 191549 | 192067 | + | thymidylate kinase |
| BI00581 | 192067 | 193215 | + | DNA polymerase III, delta subunit |
| BI00582 | 193337 | 193888 | + | conserved hypothetical protein TIGR00481 |
| BI00583 | 194034 | 195632 | + | Unknown |
| BI00584 | 195767 | 197281 | + | formate--tetrahydrofolate ligase |
| BI00585 | 197684 | 198028 | − | conserved hypothetical protein |
| BI00586 | 198149 | 198763 | + | narrowly conserved hypothetical membrane protein |
| BI00587 | 198817 | 200226 | − | hypothetical membrane protein with unknown function |
| BI00588 | 200521 | 201177 | + | phosphoglycerate mutase family protein |
| BI00589 | 201278 | 202228 | + | conserved hypothetical protein |
| BI00590 | 202352 | 203224 | + | transglycolase, epimerase |
| BI00591 | 203348 | 204496 | − | extensin precursor (cell wall hydroxyproline-rich glycoprotein) |
| BI00790t | 204684 | 204866 | + | hypothetical protein BL0470 |
| BI00592 | 205053 | 206570 | + | glutamyl-tRNA synthetase |
| BI00593 | 207503 | 207988 | + | hypothetical protein Blon021299 |
| BI00594 | 207946 | 208221 | − | hypothetical protein BL0466 |
| BI00595 | 208388 | 214285 | + | cell wall surface anchor family protein, authentic frameshift |
| BI00596 | 214390 | 215208 | − | hypothetical |
| BI00597 | 216652 | 218460 | + | conserved hypothetical integral membrane protein |
| BI00598 | 218637 | 219317 | + | membrane antigen, putative |
| BI00599 | 219470 | 220744 | + | Integral membrane protein |
| BI00600 | 220769 | 222070 | + | possible permease protein of ABC transporter system |
| BI00601 | 222107 | 223327 | + | possible permease protein of ABC transporter system |
| BI00602 | 223346 | 224140 | + | ABC transporter, ATP-binding protein |
| BI00603 | 224259 | 224819 | + | lipoprotein, putative |
| BI00604 | 224831 | 225427 | − | transcriptional regulator, TetR family, putative |
| BI00605 | 225545 | 227704 | − | phage infection protein, putative |
| BI00606 | 227704 | 230250 | − | phage infection protein, putative |
| BI00607 | 230686 | 231969 | + | membrane protein, putative |
| BI00608 | 232037 | 233602 | + | 6-phosphogluconate dehydrogenase, decarboxylating |
| BI00609 | 233756 | 234595 | − | 6-phosphogluconolactonase |
| BI00610 | 234825 | 235847 | − | oxppcycle protein OpcA |
| BI00611 | 235847 | 237499 | − | glucose-6-phosphate 1-dehydrogenase |
| BI00612 | 237652 | 239337 | + | Unknown |
| BI00613 | 239417 | 240448 | − | Glycosyltransferase involved in cell wall biogenesis |
| BI00614 | 240475 | 241311 | − | transcriptional regulator, TetR family |
| BI00615 | 241407 | 242675 | + | signal recognition particle-docking protein FtsY |
| BI00616 | 243046 | 244338 | + | ammonium transporter |
| BI00617 | 244343 | 244678 | + | Nitrogen regulatory protein P-II |
| BI00618 | 244832 | 246613 | + | protein-pII, uridylyltransferase |
| BI00619 | 246653 | 248095 | − | DNA-damage-inducible protein F, putative |
| BI00620 | 248301 | 249827 | + | replicative DNA helicase |
| BI00621 | 249830 | 251299 | + | UDP-N-acetylmuramyl tripeptide synthase |
| BI00622 | 251405 | 252154 | + | cobyric acid synthase |
| BI00623 | 252306 | 252590 | + | conserved hypothetical protein |
| BI00624 | 252590 | 254407 | + | ABC1 family family |
| BI00625 | 254428 | 255447 | − | transcriptional regulator, LacI family |
| BI00626 | 255933 | 257255 | + | solute binding protein of ABC transporter system |

TABLE 1-continued

Open reading frames of the genome of UCC 35624.

| GeneID | Start | End | Strand | Description |
|---|---|---|---|---|
| BI00627 | 257546 | 258469 | + | sugar ABC transporter, permease protein, putative |
| BI00628 | 258493 | 259308 | + | ABC transporter, permease protein, MalFG family |
| BI00629 | 259473 | 261446 | + | conserved hypothetical protein |
| BI00630 | 262147 | 267966 | + | hypothetical |
| BI00631 | 268074 | 271778 | + | cell wall surface anchor family protein, putative |
| BI00632 | 271911 | 272741 | + | conserved hypothetical protein TIGR00044 |
| BI00633 | 272825 | 273835 | − | prsA |
| BI00634 | 273960 | 274439 | − | hypothetical COG3210: Large exoproteins involved in heme utilization or adhesion |
| BI00635 | 274604 | 274891 | + | ribosomal protein S6 |
| BI00636 | 274951 | 275604 | + | hypothetical single-strand binding protein |
| BI00637 | 275668 | 275913 | + | ribosomal protein S18 |
| BI00638 | 275936 | 276379 | + | ribosomal protein L9 |
| BI00639 | 276769 | 277026 | + | ptsH |
| BI00640 | 277029 | 278705 | + | phosphoenolpyruvate-protein phosphotransferase |
| BI00641 | 278942 | 279673 | + | glycerol uptake facilitator protein |
| BI00642 | 279763 | 282468 | − | copper-translocating P-type ATPase |
| BI00643 | 282580 | 282858 | + | COG1937 family protein |
| BI00644 | 283012 | 284325 | + | Uncharacterized BCR, YigN family, COG1322 family |
| BI00645 | 284325 | 284951 | + | conserved hypothetical protein |
| BI00646 | 285048 | 285893 | + | COG0566: rRNA methylases |
| BI00647 | 285787 | 286359 | + | glutamyl-tRNA(Gln) amidotransferase, C subunit |
| BI00648 | 286366 | 287904 | + | glutamyl-tRNA(Gln) amidotransferase, A subunit |
| BI00649 | 287933 | 289429 | + | glutamyl-tRNA(Gln) amidotransferase, B subunit |
| BI00650 | 289728 | 290789 | + | possible acetyltransferase |
| BI00651 | 290803 | 291114 | + | conserved hypothetical protein |
| BI00652 | 291501 | 293141 | + | conserved hypothetical protein |
| BI00653 | 293363 | 294973 | + | BarJ |
| BI00654 | 295245 | 297248 | + | transcription termination factor Rho |
| BI00655 | 297358 | 297501 | + | hypothetical protein |
| BI00656 | 297559 | 297945 | + | chorismate mutase |
| BI00657 | 298070 | 300151 | + | cell wall surface anchor family protein, putative |
| BI00658 | 300383 | 303220 | − | valyl-tRNA synthetase, putative |
| BI00659 | 303262 | 304686 | − | ABC transporter, periplasmic substrate-binding protein, putative |
| BI00660 | 304850 | 305533 | − | endonuclease III |
| BI00661 | 305595 | 306374 | − | transcriptional regulator |
| BI00662 | 306556 | 307212 | − | membrane protein, putative |
| BI00663 | 307369 | 307950 | − | integral membrane protein in the upf0059 |
| BI00664 | 308187 | 308678 | − | inorganic pyrophosphatase |
| BI00665 | 308908 | 311145 | − | alpha-amylase family protein |
| BI00666 | 311386 | 313377 | + | conserved hypothetical protein |
| BI00667 | 313988 | 315019 | + | homoserine O-succinyltransferase |
| BI00668 | 315484 | 316293 | + | ATP synthase F0, A subunit |
| BI00669 | 316400 | 316624 | + | ATP synthase F0, C subunit |
| BI00670 | 316684 | 317199 | + | ATP synthase F0, B subunit |
| BI00671 | 317237 | 318070 | + | ATP synthase F1, delta subunit |
| BI00672 | 318149 | 319777 | + | ATP synthase F1, alpha subunit |
| BI00673 | 319784 | 320704 | + | ATP synthase F1, gamma subunit |
| BI00674 | 320716 | 322185 | + | ATP synthase F1, beta subunit |
| BI00675 | 322188 | 322478 | + | ATP synthase F1, epsilon subunit, putative |
| BI00676 | 322539 | 323336 | + | Predicted nuclease of the RecB family |
| BI00677 | 323388 | 324374 | − | possible secreted peptidyl-prolyl cis-trans isomerase protein |
| BI00678 | 324455 | 325531 | + | conserved hypothetical protein |
| BI00679 | 325534 | 326538 | + | conserved hypothetical protein |
| BI00680 | 326790 | 327761 | + | thioredoxin [imported], putative |
| BI00681 | 327850 | 328473 | − | Adenylate cyclase |
| BI00682 | 329012 | 329398 | + | endoribonuclease L-PSP, putative |
| BI00683 | 329536 | 330498 | + | Acyltransferase domain protein |
| BI00684 | 330595 | 331593 | + | glycerol-3-phosphate dehydrogenase, NAD-dependent |
| BI00685 | 331783 | 332967 | + | D-ala D-ala ligase |
| BI00686 | 333223 | 334386 | + | ABC transporter, periplasmic substrate-binding protein |
| BI00687 | 334206 | 335348 | + | spermidine/putrescine ABC transporter, permease protein, putative |
| BI00688 | 335348 | 336199 | + | spermidine/putrescine ABC transporter, permease protein, putative |
| BI00689 | 336207 | 337481 | + | spermidine/putrescine ABC transporter, ATP-binding protein |
| BI00690 | 337788 | 338828 | + | CAAX amino terminal protease family protein family |

TABLE 1-continued

Open reading frames of the genome of UCC 35624.

| GeneID | Start | End | Strand | Description |
|---|---|---|---|---|
| BI00691 | 338873 | 339667 | − | Mechanosensitive ion channel family |
| BI00692 | 339751 | 341181 | − | aspartate ammonia-lyase |
| BI00693 | 341302 | 342030 | − | transcriptional regulator, TetR family domain protein |
| BI00694 | 342124 | 343527 | − | conserved hypothetical protein |
| BI00695 | 343852 | 344400 | − | methylated-DNA--protein-cysteine methyltransferase |
| BI00696 | 345228 | 346055 | + | hypothetical protein with helix turn helix motif |
| BI00697 | 345928 | 347202 | − | MFS transporter family protein, putative |
| BI00698 | 347393 | 348406 | − | ribokinase [imported] |
| BI00939t | 348735 | 349001 | + | ribosomal protein L28 |
| BI00699 | 349116 | 351944 | + | ATP-dependent DNA helicase RecG |
| BI00700 | 352204 | 352782 | + | methyltransferase, putative |
| BI00701 | 352812 | 353624 | − | tRNA (guanine-N1)-methyltransferase |
| BI00702 | 353623 | 355341 | + | Unknown |
| BI00703 | 355422 | 356399 | + | conserved hypothetical protein |
| BI00704 | 356482 | 357354 | + | 4-diphosphocytidyl-2C-methyl-D-erythritol synthase, putative |
| BI00705 | 357367 | 358041 | + | pyrrolidone-carboxylate peptidase, putative |
| BI00706 | 358303 | 359766 | + | IgA-specific serine endopeptidase, putative |
| BI00707 | 359884 | 361224 | + | aminopeptidase C |
| BI00708 | 361519 | 362649 | + | phospho-2-dehydro-3-deoxyheptonate aldolase |
| BI00709 | 362781 | 364010 | + | phospho-2-dehydro-3-deoxyheptonate aldolase |
| BI00710 | 364141 | 364845 | + | MTA/SAH nucleosidase |
| BI00711 | 365444 | 366427 | + | hypothetical ATPase, histidine kinase-, DNA gyrase B-, and HSP90-like domain protein |
| BI00712 | 366563 | 367330 | + | DNA-binding response regulator RegX3 |
| BI00713 | 367583 | 368713 | + | phosphate ABC transporter, phosphate-binding protein |
| BI00714 | 368927 | 369877 | + | pstC2 |
| BI00715 | 369997 | 370875 | + | phosphate ABC transporter, permease protein |
| BI00716 | 370931 | 371707 | + | phoT |
| BI00717 | 372005 | 372580 | + | lemA protein |
| BI00718 | 372647 | 374902 | + | conserved hypothetical protein |
| BI00719 | 374971 | 375831 | + | oxidoreductase, aldo/keto reductase family |
| BI00720 | 375932 | 376981 | + | inosine-uridine preferring nucleoside hydrolase |
| BI00721 | 377109 | 377729 | − | 16S rRNA processing protein RimM |
| BI00722 | 377755 | 377985 | − | KH domain protein |
| BI00723 | 378009 | 378467 | − | ribosomal protein S16 |
| BI00724 | 378703 | 379809 | − | Endonuclease/Exonuclease/phosphatase family family |
| BI00725 | 379889 | 381634 | − | signal recognition particle protein |
| BI00726 | 381843 | 382748 | + | cation efflux family protein superfamily |
| BI00727 | 382773 | 384488 | − | cysteinyl-tRNA synthetase |
| BI00728 | 384518 | 385363 | + | possible amidotransferase |
| BI00729 | 385627 | 387687 | + | ABC transporter, ATP-binding protein |
| BI00730 | 387746 | 388162 | − | plasmid stability protein StbB |
| BI00731 | 388175 | 388450 | − | hypothetical protein |
| BI00732 | 388609 | 389160 | − | acetolactate synthase, small subunit |
| BI00733 | 389180 | 391144 | − | acetolactate synthase, large subunit, biosynthetic type |
| BI00734 | 391308 | 392033 | − | ribonuclease III |
| BI00735 | 392189 | 392380 | − | ribosomal protein L32 |
| BI00736 | 392472 | 393098 | − | Uncharacterized ACR, COG1399 |
| BI00737 | 393191 | 394078 | − | conserved hypothetical protein |
| BI00738 | 394089 | 394586 | − | pantetheine-phosphate adenylyltransferase |
| BI00739 | 394860 | 395150 | + | conserved hypothetical protein |
| BI00740 | 395198 | 396205 | − | K+ channel, beta subunit |
| BI00741 | 396379 | 396804 | + | transcription regulator, MerR family NMB1303 [imported], putative |
| BI00742 | 396910 | 397533 | − | hypothetical transmembrane protein with unknown function |
| BI00743 | 397764 | 399083 | + | nicotinate phosphoribosyltransferase, putative |
| BI00744 | 399381 | 400142 | + | ribonuclease PH |
| BI00745 | 400189 | 400944 | + | Ham1 family |
| BI00746 | 401106 | 402659 | + | hypothetical FemAB family |
| BI00747 | 402736 | 404043 | + | FemAB family protein, putative |
| BI00748 | 404096 | 405373 | + | beta-lactam resistance factor, putative |
| BI00749 | 405462 | 406460 | − | membrane protein, putative |
| BI00750 | 407182 | 408879 | + | glucose-6-phosphate isomerase |
| BI00751 | 409515 | 409877 | + | ribosomal protein L19 |
| BI00752 | 410047 | 410901 | + | lepB |
| BI00753 | 411024 | 411860 | + | ribonuclease HII |
| BI00754 | 411990 | 413102 | + | transcription regulator, LacI family [imported] |
| BI00755 | 413261 | 414904 | + | probable sugar kinase |
| BI00756 | 414992 | 415681 | + | sugar isomerase |

TABLE 1-continued

Open reading frames of the genome of UCC 35624.

| GeneID | Start | End | Strand | Description |
| --- | --- | --- | --- | --- |
| BI00757 | 416114 | 417430 | + | L-arabinose isomerase |
| BI00758 | 417620 | 418240 | − | trp-G type glutamine amidotransferase/dipeptidase |
| BI00759 | 418178 | 420178 | + | membrane protein, putative |
| BI00760 | 420330 | 421694 | + | permease, putative |
| BI00761 | 421694 | 422914 | + | transmembrane protein Vexp1, putative |
| BI00762 | 422930 | 423562 | + | Vexp2 |
| BI00763 | 423886 | 425706 | − | long-chain-fatty-acid--CoA ligase, putative |
| BI00764 | 425820 | 426098 | + | fragment of arabinose permease |
| BI00765 | 426765 | 429890 | + | hypothetical ABC transporter |
| BI00766 | 430170 | 430436 | − | major facilitator family transporter CC0814 [imported], putative |
| BI00767 | 431272 | 432618 | + | solute binding protein of ABC transporter system |
| BI00768 | 432750 | 433799 | + | sugar ABC transporter, permease protein, putative |
| BI00769 | 433820 | 434809 | + | Unknown |
| BI00770 | 435125 | 437128 | + | beta-D-galactosidase, putative |
| BI00771 | 437175 | 438227 | + | transcription regulator, LacI family [imported], putative |
| BI00772 | 438426 | 441116 | + | arabinogalactan endo-1,4-beta-galactosidase, putative |
| BI00773 | 441755 | 442621 | + | oxidoreductase, aldo/keto reductase family |
| BI00774 | 442628 | 443368 | + | conserved hypothetical protein |
| BI00775 | 443378 | 444745 | − | conserved hypothetical protein |
| BI00776 | 445003 | 446367 | + | transport protein, NRAMP family |
| BI00777 | 446472 | 448073 | − | drug resistance transporter, EmrB/QacA subfamily |
| BI00778 | 448424 | 450007 | + | glycosyl transferase CpsE |
| BI00779 | 450302 | 452029 | + | COG0840: Methyl-accepting chemotaxis protein |
| BI00780 | 452064 | 453566 | + | possible Etk-like tyrosine kinase involved in Eps biosynthesis |
| BI00781 | 453760 | 454725 | + | hypothetical glycosyl transferase, group 1 family protein |
| BI00782 | 454725 | 456065 | + | putative glycosyltransferase protein |
| BI00783 | 456065 | 457126 | + | NAD dependent epimerase/dehydratase family protein |
| BI00784 | 457201 | 458448 | + | UDP-glucose 6-dehydrogenase |
| BI00785 | 458489 | 459550 | + | hypothetical glycosyl transferase, group 1 family protein |
| BI00786 | 459581 | 460408 | + | hypothetical Eps11I |
| BI00787 | 460446 | 460952 | + | hypothetical Bacterial transferase hexapeptide (three repeats) |
| BI00788 | 460985 | 461998 | + | hypothetical Capsular polysaccharide synthesis protein |
| BI00789 | 462020 | 463360 | + | hypothetical protein |
| BI00790 | 463363 | 464292 | + | Eps9K |
| BI00791 | 464362 | 465753 | + | hypothetical Polysaccharide biosynthesis protein |
| BI00792 | 465789 | 466280 | + | hypothetical Bacterial transferase hexapeptide (three repeats) |
| BI00793 | 466366 | 467514 | − | NAD-dependent epimerase/dehydratase family protein, putative |
| BI00794 | 467785 | 468363 | − | transposase, degenerate |
| BI00795 | 468615 | 468770 | − | hypothetical COG2963: Transposase and inactivated derivatives |
| BI00796 | 469189 | 470208 | + | dTDP-glucose 4,6-dehydratase |
| BI00797 | 470347 | 471303 | + | dTDP-4-dehydrorhamnose 3,5-epimerase |
| BI00798 | 471349 | 472245 | + | glucose-1-phosphate thymidylyltransferase |
| BI00799 | 472858 | 473046 | − | hypothetical protein |
| BI00800 | 473371 | 473802 | − | conserved hypothetical protein |
| BI00801 | 474083 | 474640 | − | hypothetical Low molecular weight phosphotyrosine protein phosphatase |
| BI00802 | 474825 | 475331 | − | hypothetical protein |
| BI00803 | 475655 | 475867 | − | hypothetical Helix-turn-helix |
| BI00804 | 475860 | 476042 | − | hypothetical protein |
| BI00805 | 475971 | 476312 | + | hypothetical protein |
| BI00806 | 476415 | 477422 | − | conserved hypothetical protein |
| BI00807 | 477471 | 478751 | + | narrowly conserved hypothetical protein |
| BI00808 | 477495 | 477866 | − | thioredoxin |
| BI00809 | 478880 | 479734 | + | 3-oxoadipate enol-lactonase, putative |
| BI00810 | 479747 | 481036 | + | MutT/nudix family protein |
| BI00811 | 481065 | 481475 | + | glycine cleavage system H protein |
| BI00812 | 481547 | 482875 | + | conserved hypothetical protein |
| BI00813 | 482973 | 485453 | + | protease II |
| BI00814 | 485521 | 486549 | + | 3-isopropylmalate dehydrogenase |
| BI00815 | 486610 | 487692 | + | lipoate-protein ligase a |
| BI00817 | 487934 | 488650 | + | probable transcriptional regulator with cyclic nucleotide-binding domain |

TABLE 1-continued

Open reading frames of the genome of UCC 35624.

| GeneID | Start | End | Strand | Description |
|---|---|---|---|---|
| BI00818 | 488757 | 491069 | + | ponA, putative |
| BI00819 | 491264 | 492634 | + | NADH-dependent flavin oxidoreductase, putative |
| BI00820 | 492807 | 493955 | − | dihydroorotate dehydrogenase, putative |
| BI00821 | 494409 | 495122 | + | glycerol-3-phosphate regulon repressor |
| BI00822 | 495118 | 496365 | + | galactose-1-phosphate uridylyltransferase |
| BI00823 | 496241 | 497632 | + | galactokinase |
| BI00824 | 497718 | 497987 | + | ACT domain protein |
| BI00825 | 498201 | 499487 | + | similar to unknown proteins |
| BI00826 | 499800 | 500516 | − | spoU |
| BI00827 | 500612 | 501463 | + | mutY |
| BI00828 | 501531 | 502250 | + | conserved hypothetical protein |
| BI00829 | 502633 | 505968 | + | DNA-directed RNA polymerase, beta subunit |
| BI00830 | 506139 | 510173 | + | DNA-directed RNA polymerase, beta-prime subunit |
| BI00831 | 510338 | 510967 | − | FHA domain protein |
| BI00832 | 510986 | 511498 | − | hypothetical protein Blon020438 |
| BI00833 | 511528 | 512457 | − | possible phosphoprotein phosphatase |
| BI00834 | 512457 | 514967 | − | membrane protein, putative |
| BI00835 | 514967 | 516187 | − | Protein of unknown function family |
| BI00836 | 516215 | 517585 | − | moxR2 |
| BI00837 | 517599 | 523580 | − | cell wall surface anchor family protein, putative |
| BI00838 | 523750 | 525168 | − | serine/threonine protein kinase, putative |
| BI00839 | 525300 | 529592 | + | hypothetical COG0210: Superfamily I DNA and RNA helicases |
| BI00840 | 529427 | 533620 | + | UvrD/REP helicase domain protein |
| BI00841 | 533962 | 535152 | + | possible transport protein |
| BI00842 | 535527 | 536243 | + | dihydrodipicolinate reductase |
| BI00843 | 536388 | 537311 | + | dihydrodipicolinate synthase |
| BI00844 | 537585 | 539246 | + | metallo-beta-lactamase superfamily protein |
| BI00845 | 539291 | 541897 | + | Peptidase family M1 domain protein |
| BI00846 | 542078 | 542971 | + | hypothetical transmembrane protein with unknown function |
| BI00847 | 543164 | 543502 | + | conserved hypothetical protein |
| BI00848 | 543954 | 545336 | + | phosphoglucosamine mutase |
| BI00849 | 545362 | 546012 | + | polypeptide deformylase |
| BI00850 | 546072 | 547472 | + | conserved hypothetical protein |
| BI00851 | 547492 | 547620 | + | hypothetical protein |
| BI00852 | 547858 | 548979 | + | peptide chain release factor 2 |
| BI00853 | 548991 | 550121 | + | ftsE |
| BI00854 | 550135 | 551055 | + | cell division ABC transporter, permease protein FtsX, putative |
| BI00855 | 551161 | 552519 | + | autolysin, putative |
| BI00856 | 552673 | 553146 | + | SsrA-binding protein |
| BI00857 | 553192 | 554265 | + | amino acid ABC transporter, permease protein |
| BI00858 | 554479 | 555420 | + | amino acid ABC transporter, permease protein |
| BI00859 | 555554 | 556546 | + | amino acid ABC transporter, permease protein |
| BI00860 | 556566 | 557393 | + | glutamine ABC transporter, ATP-binding protein |
| BI00861 | 557604 | 559493 | + | glucosamine--fructose-6-phosphate aminotransferase, isomerizing |
| BI00862 | 559699 | 560271 | + | COG0564: Pseudouridylate synthases, 23S RNA-specific |
| BI00863 | 560313 | 560525 | − | hypothetical protein Blon020898 |
| BI00864 | 560565 | 561548 | − | transcriptional regulator, LacI family, putative |
| BI00865 | 561794 | 562717 | + | sugar ABC transporter, permease protein, putative |
| BI00866 | 562776 | 563780 | + | Unknown |
| BI00867 | 563975 | 566047 | + | beta-D-galactosidase |
| BI00868 | 566259 | 567185 | + | transcriptional regulator, LacI family, putative |
| BI00869 | 567311 | 569008 | − | alpha-L-arabinofuranosidase |
| BI00870 | 569168 | 570517 | + | solute binding protein of ABC transporter system |
| BI00871 | 570852 | 572192 | + | probable solute binding protein of ABC transporter system for sugars |
| BI00872 | 572449 | 573729 | + | sugar binding protein Sbp |
| BI00873 | 573795 | 574562 | − | transcription activator, probable Baf family [imported] |
| BI00874 | 574688 | 576304 | + | ABC transporter, periplasmic substrate-binding protein, putative |
| BI00875 | 576372 | 577346 | + | membrane protein, putative |
| BI00876 | 577346 | 578245 | + | peptide ABC transporter, permease protein, putative |
| BI00877 | 578245 | 579033 | + | ABC transporter, nucleotide binding/ATPase protein |
| BI00878 | 579029 | 579811 | + | ABC transporter, ATP-binding protein |
| BI00879 | 580296 | 581360 | + | cystathionine beta-synthase |
| BI00880 | 581455 | 582636 | + | cystathionine beta-lyase |
| BI00881 | 582780 | 584501 | − | ErfK/YbiS/YcfS/YnhG family |
| BI00882 | 584781 | 586613 | + | ATP-dependent DNA helicase RecQ |

TABLE 1-continued

Open reading frames of the genome of UCC 35624.

| GeneID | Start | End | Strand | Description |
|---|---|---|---|---|
| BI00883 | 586729 | 587220 | + | autoinducer-2 production protein LuxS |
| BI00884 | 587453 | 587917 | + | acetyltransferase, GNAT family, putative |
| BI00885 | 588181 | 589638 | − | hypothetical protein Blon020876 |
| BI00886 | 589890 | 591347 | − | amino acid permease |
| BI00887 | 591542 | 592891 | + | alanine racemase |
| BI00888 | 593087 | 594370 | + | deoxyguanosinetriphosphate triphosphohydrolase, putative |
| BI00889 | 594546 | 596642 | + | DNA primase, putative |
| BI00890 | 596961 | 597710 | + | pyridoxine biosynthesis protein |
| BI00891 | 597799 | 598434 | + | SNO glutamine amidotransferase family superfamily |
| BI00892 | 598495 | 600156 | + | aminotransferase, class I, putative |
| BI00893 | 600514 | 601443 | + | asparaginase family protein |
| BI00894 | 601476 | 601607 | + | hypothetical protein Blon020867 |
| BI00895 | 601574 | 601897 | − | hypothetical protein |
| BI00896 | 601995 | 603179 | + | possible transport protein |
| BI00897 | 603210 | 603467 | − | hypothetical protein Blon020865 |
| BI00898 | 603634 | 603723 | + | hypothetical protein |
| BI00899 | 603651 | 605795 | − | similar to alpha-L-arabinofuranosidase A |
| BI00900 | 605923 | 606921 | + | EF0065, putative |
| BI00901 | 607014 | 608087 | − | conserved hypothetical protein |
| BI00902 | 608687 | 609373 | + | ABC transporter, ATP-binding protein |
| BI00903 | 609373 | 610545 | + | conserved hypothetical protein |
| BI00904 | 610560 | 612116 | + | ABC transporter, ATP-binding protein |
| BI00905 | 612106 | 614304 | − | 1-deoxyxylulose-5-phosphate synthase |
| BI00906 | 614478 | 615467 | + | oxidoreductase, zinc-binding, putative |
| BI00907 | 615572 | 616069 | + | phosphoribosylaminoimidazole carboxylase, catalytic subunit |
| BI00908 | 616095 | 617231 | + | phosphoribosylaminoimidazole carboxylase, ATPase subunit |
| BI00909 | 617243 | 617668 | + | furB |
| BI00910 | 617709 | 617954 | − | conserved hypothetical protein |
| BI00911 | 618183 | 619103 | + | possible solute binding protein of ABC transporter system |
| BI00912 | 619367 | 621439 | + | membrane protein, putative |
| BI00913 | 621563 | 623197 | + | aldehyde dehydrogenase |
| BI00914 | 623577 | 624842 | − | phosphoribosylamine--glycine ligase |
| BI00915 | 624872 | 625702 | − | phosphoribosylformylglycinamidine cyclo-ligase |
| BI00916 | 626029 | 627537 | − | amidophosphoribosyltransferase |
| BI00917 | 627944 | 628726 | − | glutamine ABC transporter, ATP-binding protein |
| BI00918 | 628726 | 629610 | − | amino acid ABC transporter, permease protein |
| BI00919 | 629723 | 630583 | − | amino acid ABC transporter, periplasmic amino acid-binding protein |
| BI00920 | 630788 | 631255 | − | conserved hypothetical protein |
| BI00921 | 631328 | 632698 | − | Atz/Trz family protein, putative |
| BI00922 | 632741 | 634240 | − | S-adenosyl-L-homocysteine hydrolase, NAD binding domain |
| BI00923 | 634405 | 635991 | + | structural gene for ultraviolet resistance |
| BI00924 | 635991 | 636206 | + | hypothetical protein Blon020836 |
| BI00925 | 636246 | 637220 | − | K+ channel, beta subunit |
| BI00926 | 637331 | 638293 | − | transcriptional regulator, HTH_1 family, putative |
| BI00927 | 638512 | 640023 | + | Na+/H+ antiporter, putative |
| BI00928 | 640043 | 640699 | − | membrane protein, putative |
| BI00929 | 640699 | 642066 | − | conserved hypothetical protein |
| BI00930 | 642042 | 643337 | − | possible carboxylesterase or lipase |
| BI00931 | 643478 | 647209 | − | phosphoribosylformylglycinamidine synthase |
| BI00932 | 647275 | 648024 | − | phosphoribosylaminoimidazole-succinocarboxamide synthase |
| BI00933 | 648113 | 648232 | − | hypothetical protein |
| BI00934 | 648420 | 649754 | − | phosphoribosylglycinamide formyltransferase 2 VC1228 [imported] |
| BI00935 | 649928 | 651085 | + | type 1 capsular polysaccharide biosynthesis protein J (capJ) |
| BI00936 | 651238 | 652260 | − | conserved hypothetical protein |
| BI00937 | 652822 | 653880 | + | transporter |
| BI00938 | 654695 | 654967 | + | ribosomal protein S12 |
| BI00939 | 654976 | 655443 | + | ribosomal protein S7 |
| BI00940 | 655478 | 657598 | + | translation elongation factor G |
| BI00941 | 657774 | 658970 | + | translation elongation factor Tu |
| BI00942 | 659184 | 659909 | + | conserved hypothetical protein |
| BI00943 | 660169 | 660864 | + | transcriptional regulator, LysR family, putative |
| BI00944 | 661085 | 662098 | + | membrane protein, putative |
| BI00945 | 662161 | 662637 | − | COG2246: Predicted membrane protein |
| BI00946 | 662721 | 663083 | − | CrcB protein |
| BI00947 | 663086 | 663619 | − | protein with similarity to CrcB |
| BI00948 | 663706 | 663987 | + | hypothetical protein |

TABLE 1-continued

Open reading frames of the genome of UCC 35624.

| GeneID | Start | End | Strand | Description |
|---|---|---|---|---|
| BI00949 | 664023 | 665063 | + | alcohol dehydrogenase, zinc-containing |
| BI00950 | 665437 | 665625 | + | hypothetical protein |
| BI00951 | 665652 | 667028 | − | conserved hypothetical protein |
| BI00952 | 667295 | 667462 | − | possible MarR-type transcriptional regulator |
| BI00953 | 667902 | 670487 | + | excinuclease ABC, subunit A |
| BI00954 | 670548 | 671903 | + | MATE efflux family protein, putative |
| BI00955 | 671914 | 672603 | + | endonuclease III, putative |
| BI00956 | 672783 | 673076 | − | hypothetical protein Blon020400 |
| BI00957 | 673098 | 673766 | + | Unknown |
| BI00958 | 673782 | 674042 | − | hexapeptide-repeat containing-acetyltransferase |
| BI00959 | 674207 | 675292 | + | possible integral membrane permease protein |
| BI00960 | 675273 | 675902 | + | hypothetical Glycosyl hydrolases family 2, TIM barrel domain |
| BI00961 | 676090 | 677316 | − | glutamine synthetase, type I |
| BI00962 | 677846 | 678625 | − | narrowly conserved hypothetical transmembrane protein |
| BI00963 | 678712 | 680199 | − | dihydrolipoamide dehydrogenase |
| BI00964 | 680351 | 680971 | − | conserved hypothetical protein |
| BI00965 | 681063 | 682427 | + | widely conserved protein in peptidase or deacetlylase family |
| BI00966 | 682730 | 683326 | + | conserved hypothetical protein |
| BI00967 | 683329 | 684801 | + | ABC transporter, ATP-binding protein, putative |
| BI00968 | 684801 | 685625 | + | possible permease protein of ABC transporter for cobalt |
| BI00969 | 685824 | 686699 | + | spoU rRNA methylase family protein [imported] |
| BI00970 | 686891 | 687820 | + | phenylalanyl-tRNA synthetase, alpha subunit |
| BI00971 | 687831 | 690437 | + | phenylalanyl-tRNA synthetase, beta subunit |
| BI00972 | 690471 | 691154 | + | conserved hypothetical protein |
| BI00973 | 691385 | 692347 | + | N-acetyl-gamma-glutamyl-phosphate reductase |
| BI00974 | 692434 | 693519 | + | arginine biosynthesis bifunctional protein ArgJ |
| BI00013g | 693503 | 693979 | − | hypothetical protein Magn025872 |
| BI00975 | 693809 | 694612 | + | acetylglutamate kinase |
| BI00976 | 694605 | 695897 | + | acetylornithine aminotransferase |
| BI00977 | 695944 | 696906 | + | ornithine carbamoyltransferase |
| BI00978 | 696906 | 697415 | + | arginine repressor |
| BI00979 | 697501 | 698736 | + | argininosuccinate synthase |
| BI00980 | 699184 | 700653 | + | argininosuccinate lyase |
| BI01326t | 701005 | 701196 | + | thiamine biosynthesis protein ThiS |
| BI00981 | 701211 | 702077 | + | thiG protein |
| BI00982 | 702157 | 702963 | + | moeB |
| BI00983 | 703023 | 703376 | + | rhodanese-like domain protein |
| BI00984 | 703541 | 704071 | + | HD domain protein |
| BI00985 | 703978 | 704835 | + | hypothetical |
| BI00986 | 704964 | 706283 | + | tyrosyl-tRNA synthetase |
| BI00987 | 706314 | 708086 | + | hypothetical protein BL1050 |
| BI00988 | 708098 | 709135 | + | Predicted sugar phosphatases of the HAD superfamily |
| BI00989 | 709395 | 710165 | + | hemolysin A |
| BI00990 | 710153 | 710719 | − | conserved hypothetical protein |
| BI00991 | 710729 | 710881 | + | hypothetical protein |
| BI00992 | 710965 | 711624 | − | similar to a bacterial K(+)-uptake system |
| BI00993 | 711678 | 713141 | − | Cation transport protein domain protein |
| BI00994 | 713388 | 714407 | + | poly(P)/ATP-NAD kinase |
| BI00995 | 714410 | 716233 | + | DNA repair protein RecN |
| BI00996 | 716266 | 716910 | + | hydrolase, haloacid dehalogenase-like family, putative |
| BI00997 | 717154 | 717525 | + | transcriptional regulator, GntR family |
| BI00998 | 717550 | 718467 | + | ABC transporter, ATP-binding protein |
| BI01351t | 718477 | 719091 | + | membrane protein, putative |
| BI00999 | 719985 | 722768 | − | calcium-translocating P-type ATPase, PMCA-type |
| BI01000 | 722966 | 723238 | + | hypothetical protein BL1037 |
| BI01001 | 723291 | 724778 | − | threonine synthase |
| BI01356t | 725001 | 725699 | + | serine hydroxymethyltransferase |
| BI01002 | 726028 | 727116 | + | gamma-glutamyl phosphate reductase |
| BI01003 | 727134 | 727694 | + | conserved hypothetical protein |
| BI01004 | 727694 | 728476 | + | nicotinate (nicotinamide) nucleotide adenylyltransferase |
| BI01005 | 728580 | 729857 | − | glycosyl hydrolase, family 3, putative |
| BI01006 | 729952 | 733203 | + | Uncharacterized ACR |
| BI01007 | 733340 | 733834 | + | phosphinothricin acetyltransferase |
| BI01008 | 734033 | 734629 | + | peptidyl-tRNA hydrolase |
| BI01009 | 734622 | 738203 | + | transcription-repair coupling factor |
| BI01010 | 738346 | 739290 | + | oxidoreductase, putative |
| BI01011 | 739444 | 740739 | + | enolase |
| BI01012 | 740809 | 741423 | + | hypothetical Septum formation initiator |

TABLE 1-continued

Open reading frames of the genome of UCC 35624.

| GeneID | Start | End | Strand | Description |
|---|---|---|---|---|
| BI01013 | 741423 | 741986 | + | conserved hypothetical protein |
| BI01014 | 742052 | 743050 | + | possible exopolyphosphatase-like protein |
| BI01015 | 743578 | 744711 | + | IS30 family, transposase [imported] |
| BI01016 | 744846 | 747062 | + | L-serine dehydratase 1 |
| BI01018 | 747207 | 747611 | + | peptidyl-prolyl cis-trans isomerase, FKBP-type |
| BI01019 | 747713 | 748189 | + | transcription elongation factor GreA |
| BI01020 | 748250 | 749191 | − | hemolysin, putative |
| BI01021 | 749361 | 750086 | + | conserved hypothetical protein |
| BI01022 | 750474 | 751736 | + | histidine kinase-like protein |
| BI01023 | 751815 | 752090 | − | hypothetical Transcription factor WhiB |
| BI01024 | 752207 | 753922 | − | diarrheal toxin |
| BI01025 | 754203 | 755633 | − | Transcriptional regulator |
| BI01389t | 755884 | 756180 | + | whiB1 |
| BI01026 | 756350 | 759319 | + | membrane protein, putative |
| BI01027 | 759319 | 760857 | + | LPXTG-motif cell wall anchor domain protein, putative |
| BI01028 | 760966 | 761391 | − | conserved hypothetical protein |
| BI01029 | 761660 | 762283 | + | conserved hypothetical protein |
| BI01030 | 762332 | 763015 | + | Phosphoribosyl transferase domain protein |
| BI00019g | 762937 | 763509 | − | hypothetical Peptidase family S24 |
| BI01031 | 763391 | 764464 | − | sensory box histidine kinase, putative |
| BI01032 | 764464 | 765183 | − | DNA-binding response regulator MtrA |
| BI01033 | 765222 | 767432 | − | 1,4-alpha-glucan branching enzyme |
| BI01034 | 767649 | 768239 | + | possible transcriptional regulator |
| BI01035 | 768351 | 768872 | + | 2C-methyl-D-erythritol 2,4-cyclodiphosphate synthase |
| BI01036 | 768930 | 769760 | − | zinc ABC transporter, permease protein, putative |
| BI01037 | 769830 | 770834 | − | ABC transporter, ATP-binding protein |
| BI01038 | 770893 | 772419 | − | possible solute binding protein of ABC transporter system |
| BI01039 | 772190 | 773062 | + | methylenetetrahydrofolate dehydrogenase/methenyltetrahydrofolate cyclohydrolase |
| BI01040 | 773185 | 774657 | + | ribosomal protein S1 [imported] |
| BI01041 | 774834 | 775448 | + | dephospho-CoA kinase |
| BI01042 | 775463 | 777571 | + | excinuclease ABC, B subunit |
| BI01043 | 777887 | 778726 | + | TerC family protein [imported] |
| BI01044 | 778897 | 780336 | + | pyruvate kinase |
| BI01045 | 780490 | 781086 | − | possible NTP pyrophosphatase in MutT family |
| BI01046 | 781432 | 782214 | + | response regulator |
| BI01047 | 782278 | 785127 | + | DNA polymerase I |
| BI01048 | 785291 | 786217 | + | conserved hypothetical protein TIGR00486 |
| BI01049 | 786266 | 786937 | + | MutT/nudix family protein, putative |
| BI01050 | 787135 | 789132 | + | glycogen operon protein GlgX |
| BI01424t | 789186 | 789413 | + | hypothetical protein with helix turn helix motif |
| BI01051 | 789420 | 790067 | + | conserved hypothetical protein |
| BI01052 | 790243 | 790794 | − | DNA-3-methyladenine glycosylase I |
| BI01053 | 791884 | 792942 | − | hypothetical protein |
| BI01054 | 793226 | 793780 | + | hypothetical protein |
| BI01055 | 793761 | 794246 | − | hypothetical protein |
| BI00021g | 794049 | 794498 | + | transposase B |
| BI00020g | 794300 | 794749 | + | IS1601-D |
| BI01056 | 794665 | 794844 | + | transposase subunit B |
| BI01057 | 794937 | 795989 | − | integrase/recombinase XerC, probable [imported], putative |
| BI01434t | 795989 | 796876 | − | probable integrase/recombinase |
| BI01058 | 796951 | 798150 | − | probable integrase/recombinase |
| BI01059 | 798284 | 799564 | − | IS3-Spn1, transposase |
| BI01060 | 799635 | 800477 | − | putative transposase subunit |
| BI01061 | 800762 | 802579 | − | hypothetical Protein of unknown function DUF262 |
| BI01062 | 802742 | 803464 | − | hypothetical protein |
| BI01063 | 803748 | 804065 | − | conserved hypothetical protein |
| BI01064 | 804058 | 804405 | − | hypothetical protein |
| BI01065 | 804667 | 808221 | + | DNA polymerase III, alpha chain VC2245 [imported] |
| BI01066 | 808312 | 808743 | + | conserved hypothetical protein |
| BI01067 | 808952 | 810826 | + | antigen, 67 kDa |
| BI01068 | 810916 | 811413 | + | NH2-acetyltransferase |
| BI01069 | 817553 | 818377 | − | oxidoreductase, aldo/keto reductase family |
| BI01070 | 818538 | 819956 | + | sugar kinase, FGGY family, putative |
| BI01451t | 819972 | 820262 | + | Acylphosphatase |
| BI01071 | 820382 | 821761 | + | histidinol dehydrogenase |
| BI01072 | 821761 | 822918 | + | histidinol-phosphate aminotransferase |
| BI01073 | 823007 | 823603 | + | imidazoleglycerol-phosphate dehydratase |
| BI01074 | 823606 | 824397 | + | hypothetical protein Blon020586 |

TABLE 1-continued

Open reading frames of the genome of UCC 35624.

| GeneID | Start | End | Strand | Description |
|---|---|---|---|---|
| BI01075 | 824435 | 825079 | + | imidazole glycerol phosphate synthase, glutamine amidotransferase subunit |
| BI01076 | 825152 | 825874 | + | bifunctional HisA/TrpF protein |
| BI01077 | 825984 | 826103 | − | narrowly conserved hypothetical protein |
| BI01463t | 826039 | 827637 | − | conserved hypothetical protein |
| BI01078 | 827738 | 828898 | + | Glutamine synthetase, catalytic domain |
| BI01079 | 829137 | 829604 | + | transporter, putative |
| BI01080 | 829657 | 830625 | − | conserved hypothetical protein |
| BI01081 | 830625 | 834758 | − | ATP-dependent helicase HrpA |
| BI01082 | 834751 | 835404 | − | conserved hypothetical protein |
| BI01083 | 835647 | 837065 | + | GTP-binding protein |
| BI01084 | 837405 | 838208 | + | L-lactate dehydrogenase |
| BI01085 | 838356 | 839291 | − | cation efflux system protein |
| BI01086 | 839460 | 840182 | − | LexA repressor |
| BI01087 | 840333 | 840680 | + | LysM domain protein |
| BI01088 | 840736 | 841173 | + | conserved hypothetical protein TIGR00244 |
| BI01089 | 841314 | 842510 | − | D-3-phosphoglycerate dehydrogenase |
| BI01090 | 842524 | 844800 | − | COG3973: Superfamily I DNA and RNA helicases |
| BI01091 | 845133 | 845651 | + | conserved hypothetical protein TIGR00242 |
| BI01092 | 845654 | 846730 | + | S-adenosyl-methyltransferase MraW |
| BI01093 | 846740 | 847186 | + | hypothetical protein Blon020568 |
| BI01094 | 847186 | 848985 | + | penicillin-binding protein, putative |
| BI01095 | 849015 | 849884 | + | conserved hypothetical protein |
| BI01096 | 849936 | 851384 | + | UDP-N-acetylmuramoylalanyl-D-glutamyl-2,6-diaminopimelate--D-alanyl-D-alanyl ligase |
| BI01097 | 851453 | 852535 | + | phospho-N-acetylmuramoyl-pentapeptide-transferase |
| BI01098 | 852593 | 854035 | + | UDP-N-acetylmuramoylalanine--D-glutamate ligase |
| BI01099 | 854025 | 855239 | + | cell division protein, FtsW/RodA/SpoVE family, putative |
| BI01100 | 855258 | 856436 | + | UDP-N-acetylglucosamine--N-acetylmuramyl-(pentapeptide) pyrophosphoryl-undecaprenol N-acetylglucosamine transferase |
| BI01101 | 856651 | 858075 | + | UDP-N-acetylmuramate--alanine ligase |
| BI01102 | 858078 | 859139 | + | hypothetical Cell division protein FtsQ |
| BI01103 | 859565 | 860983 | + | hypothetical Appr-1-p processing enzyme family |
| BI01104 | 861241 | 861813 | + | unknown |
| BI01105 | 861640 | 861885 | − | hypothetical protein |
| BI01106 | 861906 | 862391 | + | D-tyrosyl-tRNA(Tyr) deacylase |
| BI01107 | 862494 | 863735 | − | glucose/galactose transporter, putative |
| BI01108 | 863844 | 864230 | − | hypothetical glyoxalase family protein |
| BI01109 | 864308 | 865201 | − | fructokinase, putative |
| BI01110 | 865277 | 866488 | − | transcription regulator ROK family VC2007 [imported], putative |
| BI01111 | 866715 | 867626 | + | glucokinase, putative |
| BI01112 | 867792 | 868913 | − | NagC/XylR-type transcriptional regulator |
| BI01113 | 869251 | 870060 | + | glucosamine-6-phosphate isomerase |
| BI01114 | 870119 | 871393 | + | N-acetylglucosamine-6-phosphate deacetylase |
| BI01115 | 871646 | 873307 | + | dipeptide ABC transporter, dipeptide-binding protein |
| BI01116 | 873480 | 874568 | + | oligopeptide ABC transporter, permease protein |
| BI01117 | 874714 | 875739 | + | dipeptide ABC transporter, permease protein |
| BI01118 | 875746 | 877452 | + | ATP binding protein of ABC transporter |
| BI01119 | 877508 | 878026 | − | MutT/nudix family protein |
| BI01120 | 878078 | 879670 | − | Xaa-Pro aminopeptidase I |
| BI01121 | 879977 | 880954 | − | conserved hypothetical protein |
| BI01122 | 882044 | 883672 | + | folC |
| BI01123 | 883736 | 887410 | + | SMC family, C-terminal domain family |
| BI01124 | 887535 | 888527 | − | conserved hypothetical protein |
| BI01125 | 888652 | 890202 | − | UDP-N-acetylmuramoylalanyl-D-glutamate-2,6-diaminopimelate ligase |
| BI01126 | 890377 | 891126 | + | RNA polymerase sigma-70 factor, ECF subfamily |
| BI01127 | 891129 | 891446 | + | conserved hypothetical protein |
| BI01128 | 891719 | 892660 | − | Aldose 1-epimerase superfamily |
| BI01129 | 892788 | 893741 | − | Aldose 1-epimerase superfamily |
| BI01130 | 894032 | 895021 | + | hydroxymethylbutenyl pyrophosphate reductase |
| BI01131 | 895067 | 895573 | − | transcriptional regulator, putative |
| BI01132 | 895670 | 896725 | − | glyceraldehyde-3-phosphate dehydrogenase, type I |
| BI01133 | 896968 | 897690 | − | Thiamin pyrophosphokinase, catalytic domain family |
| BI01134 | 897586 | 898923 | + | hypothetical Spermine/spermidine synthase |
| BI01135 | 899364 | 899930 | + | Translation initiation factor IF-3, C-terminal domain |

TABLE 1-continued

Open reading frames of the genome of UCC 35624.

| GeneID | Start | End | Strand | Description |
|---|---|---|---|---|
| BI00041g | 899764 | 900105 | + | ribosomal protein L35 |
| BI01136 | 900161 | 900541 | + | ribosomal protein L20 |
| BI01137 | 900605 | 901537 | + | Integrase |
| BI01138 | 901668 | 904511 | + | ABC transporter, ATP-binding protein |
| BI01139 | 904656 | 905612 | + | Soj family protein |
| BI01140 | 905634 | 906545 | + | Uncharacterised ACR, COG1354 |
| BI01141 | 906675 | 907274 | + | conserved hypothetical protein TIGR00281 |
| BI01142 | 907409 | 908233 | + | MutT/nudix family protein |
| BI01143 | 908296 | 909573 | + | quinolinate synthetase complex, A subunit |
| BI01144 | 909668 | 911296 | + | L-aspartate oxidase |
| BI01145 | 911303 | 912193 | + | nicotinate-nucleotide pyrophosphorylase |
| BI01146 | 912292 | 913443 | + | possible pyridoxal-phosphate-dependent aminotransferase |
| BI01147 | 913478 | 914824 | + | major facilitator family transporter |
| BI01148 | 915142 | 917070 | + | GTP-binding protein TypA |
| BI01149 | 917197 | 917616 | + | conserved hypothetical protein |
| BI01150 | 917699 | 918673 | + | prephenate dehydratase, putative |
| BI01151 | 918670 | 919734 | + | prephenate dehydrogenase |
| BI01152 | 919947 | 920201 | + | conserved hypothetical protein |
| BI01153 | 920239 | 921303 | + | phage integrase family protein |
| BI01154 | 921559 | 923196 | + | solute binding protein of ABC transporter system possibly for peptides |
| BI01155 | 923500 | 924423 | + | dppB |
| BI01156 | 924445 | 925446 | + | dppC |
| BI01157 | 925505 | 927478 | + | ABC-type transporter, duplicated ATPase component |
| BI01158 | 927793 | 928650 | − | exodeoxyribonuclease III |
| BI01159 | 928775 | 929626 | + | conserved hypothetical protein |
| BI01160 | 929645 | 930400 | + | narrowly conserved hypothetical transmembrane protein |
| BI01161 | 930393 | 931658 | + | RNA methyltransferase, TrmA family |
| BI01162 | 931673 | 932365 | + | lipoprotein, putative |
| BI01163 | 932483 | 935032 | + | cation-transporting ATPase, E1-E2 family |
| BI01164 | 935156 | 937852 | + | aconitate hydratase 1 |
| BI01165 | 938001 | 938360 | + | Ribbon-helix-helix protein, copG family domain protein |
| BI01166 | 938363 | 938851 | + | PIN domain, putative |
| BI01167 | 938917 | 941019 | − | Protein of unknown function DUF262 family |
| BI01168 | 941112 | 941777 | − | acetyltransferase, GNAT family family |
| BI01169 | 941793 | 942608 | − | DNA-binding response regulator, putative |
| BI01170 | 942553 | 943935 | − | atypical histidine kinase sensor of two-component system |
| BI01171 | 944117 | 944959 | + | conserved hypothetical protein |
| BI01172 | 945143 | 946039 | + | membrane protein, putative |
| BI01173 | 946326 | 947195 | + | membrane protein, putative |
| BI01174 | 947234 | 948073 | − | GTP pyrophosphokinase [imported] |
| BI01175 | 948115 | 949554 | + | tRNA-i(6)A37 thiotransferase enzyme MiaB |
| BI01176 | 949568 | 950551 | + | tRNA delta(2)-isopentenylpyrophosphate transferase |
| BI01177 | 950591 | 951517 | − | Fic protein family family |
| BI01178 | 951663 | 954437 | + | cell division protein FtsK |
| BI01179 | 954635 | 955267 | + | CDP-diacylglycerol--glycerol-3-phosphate 3-phosphatidyltransferase |
| BI01180 | 955282 | 955812 | + | competence/damage-inducible protein CinA domain protein |
| BI01181 | 955881 | 956387 | + | possible DNA binding protein |
| BI01182 | 956502 | 956732 | + | conserved hypothetical protein |
| BI01183 | 957036 | 958226 | + | recA protein |
| BI01184 | 958232 | 958822 | + | regulatory protein RecX |
| BI01185 | 959702 | 960361 | + | S30AE family protein |
| BI01186 | 960556 | 963417 | + | preprotein translocase, SecA subunit |
| BI00044g | 963734 | 963970 | − | COG3464: Transposase and inactivated derivatives |
| BI01187 | 963974 | 964096 | − | COG3464: Transposase and inactivated derivatives |
| BI00045g | 964219 | 964602 | + | hypothetical protein BL0497 |
| BI01188 | 964674 | 965717 | + | anthranilate phosphoribosyltransferase |
| BI01189 | 965964 | 966686 | − | hypothetical transmembrane protein with unknown function |
| BI01190 | 966447 | 967418 | + | hypothetical Acyltransferase |
| BI01191 | 967476 | 969722 | + | serine/threonine protein kinase, putative |
| BI01192 | 969893 | 970858 | − | idsA2 |
| BI01193 | 971179 | 971838 | + | conserved hypothetical protein |
| BI01194 | 972002 | 973465 | + | RNA polymerase principal sigma factor, sigma 70 |
| BI01195 | 973526 | 975799 | + | DNA gyrase, subunit B |
| BI01196 | 975969 | 977192 | + | membrane protein, putative |

TABLE 1-continued

Open reading frames of the genome of UCC 35624.

| GeneID | Start | End | Strand | Description |
|---|---|---|---|---|
| BI01197 | 977269 | 978228 | + | ribokinase |
| BI01198 | 978247 | 982977 | + | DEAD/DEAH box helicase domain protein |
| BI01199 | 982994 | 983779 | − | DNA-binding response regulator TcrA, putative |
| BI01200 | 983927 | 986953 | − | DNA gyrase A subunit |
| BI01201 | 986925 | 988169 | + | conserved hypothetical protein |
| BI01202 | 988185 | 989189 | − | conserved hypothetical protein |
| BI01203 | 989432 | 989722 | + | conserved hypothetical protein |
| BI01204 | 989725 | 990198 | + | deoxyuridine 5triphosphate nucleotidohydrolase |
| BI01205 | 990335 | 992656 | + | GTP pyrophosphokinase |
| BI01206 | 992780 | 993058 | − | orfB |
| BI01207 | 993226 | 994425 | + | probable integrase/recombinase |
| BI01640t | 994500 | 995387 | + | probable integrase/recombinase |
| BI01208 | 995387 | 996439 | + | integrase/recombinase XerC, probable [imported], putative |
| BI01209 | 996532 | 997095 | − | COG2801: Transposase and inactivated derivatives |
| BI00053g | 997107 | 997619 | − | ASOPSNART-11OSRSI |
| BI01210 | 997719 | 998264 | − | possible peptidyl-prolyl cis-trans isomerase |
| BI01211 | 998331 | 999296 | − | COG3391: Uncharacterized conserved protein |
| BI01212 | 999519 | 999623 | − | hypothetical protein |
| BI01213 | 999683 | 1000615 | − | membrane protein, putative |
| BI01214 | 1000747 | 1001295 | + | Hypothetical cytosolic protein |
| BI01215 | 1001329 | 1002621 | − | conserved hypothetical protein |
| BI01216 | 1002648 | 1003532 | + | possible phosphoglycerate mutase |
| BI01217 | 1003650 | 1004597 | + | magnesium transporter, CorA family |
| BI01218 | 1004615 | 1005538 | + | glnH, putative |
| BI01219 | 1005776 | 1008544 | + | leucyl-tRNA synthetase |
| BI01220 | 1008708 | 1009484 | + | competence protein ComEA helix-hairpin-helix repeat region domain protein |
| BI01221 | 1009553 | 1011235 | + | conserved hypothetical transmembrane protein related to ComA |
| BI01222 | 1011378 | 1012721 | + | possible prolidase (X-Pro dipeptidase) or chlorohydrolase |
| BI01223 | 1012791 | 1013759 | + | conserved hypothetical protein |
| BI01224 | 1013783 | 1014346 | + | conserved hypothetical protein TIGR00150 |
| BI01225 | 1014411 | 1015289 | + | conserved hypothetical protein |
| BI01226 | 1015308 | 1015859 | + | ribosomal-protein-alanine acetyltransferase |
| BI01227 | 1015859 | 1016899 | + | O-sialoglycoprotein endopeptidase |
| BI01228 | 1017438 | 1017539 | − | hypothetical protein |
| BI01229 | 1017569 | 1018501 | + | probable integrase/recombinse |
| BI01230 | 1018564 | 1018887 | − | conserved hypothetical protein |
| BI01231 | 1018909 | 1019787 | − | conserved hypothetical protein |
| BI01232 | 1019849 | 1020361 | − | conserved hypothetical protein |
| BI01233 | 1020474 | 1021376 | − | Fic protein family family |
| BI01234 | 1021357 | 1021929 | − | hypothetical protein BL1463 |
| BI01235 | 1021949 | 1023763 | − | conserved hypothetical protein |
| BI01236 | 1023782 | 1024864 | − | conserved hypothetical protein |
| BI01237 | 1024893 | 1025600 | − | conserved hypothetical protein |
| BI01238 | 1025761 | 1026843 | − | possible TraG-related protein |
| BI01239 | 1026843 | 1027799 | − | hypothetical protein Blon020262 |
| BI01240 | 1027799 | 1028164 | − | hypothetical protein Blon020261 |
| BI01242 | 1028379 | 1028669 | + | hypothetical protein Blon020260 |
| BI01241 | 1028588 | 1030942 | + | DNA topoisomerase III |
| BI01243 | 1030771 | 1031448 | + | hypothetical protein Blon020258 |
| BI01244 | 1031753 | 1032193 | + | COG1758: DNA-directed RNA polymerase, subunit K/omega |
| BI01245 | 1032161 | 1032553 | − | hypothetical protein Blon020256 |
| BI01246 | 1032621 | 1033400 | − | Fic protein family family |
| BI01247 | 1033518 | 1034822 | + | MC38, putative |
| BI01248 | 1034848 | 1036128 | − | PUTATIVE HIPA TRANSCRIPTION REGULATOR PROTEIN |
| BI01249 | 1036128 | 1036439 | − | hypothetical protein Blon020251 |
| BI01250 | 1036545 | 1037675 | − | conserved hypothetical protein |
| BI01251 | 1038618 | 1040387 | − | MC40 |
| BI01252 | 1040507 | 1041145 | − | conserved hypothetical protein |
| BI01253 | 1041250 | 1042281 | − | conserved hypothetical protein |
| BI01254 | 1042389 | 1042865 | − | conserved hypothetical protein |
| BI01255 | 1043244 | 1044842 | − | ATP binding protein-like protein |
| BI01256 | 1044857 | 1046341 | − | conserved hypothetical protein |
| BI01257 | 1046369 | 1048195 | − | lipoprotein, putative |
| BI01258 | 1048370 | 1048669 | − | conserved hypothetical protein |
| BI01259 | 1048710 | 1049189 | − | MC47, putative |
| BI01713t | 1049183 | 1050538 | + | hypothetical protein BL1487 |
| BI01260 | 1049206 | 1050405 | − | hypothetical protein |
| BI01261 | 1050435 | 1051070 | − | hypothetical protein Blon020236 |
| BI01262 | 1051396 | 1056213 | − | hypothetical COG2217: Cation transport ATPase |

TABLE 1-continued

Open reading frames of the genome of UCC 35624.

| GeneID | Start | End | Strand | Description |
|---|---|---|---|---|
| BI01263 | 1056508 | 1057458 | − | hypothetical protein Blon020231 |
| BI01264 | 1057844 | 1058440 | − | hypothetical COG1192: ATPases involved in chromosome partitioning |
| BI01265 | 1059167 | 1059430 | − | COG1192: ATPases involved in chromosome partitioning |
| BI01266 | 1059569 | 1060042 | − | possible WhiB-like transcription factor |
| BI01267 | 1060036 | 1061400 | − | conserved hypothetical protein |
| BI01727t | 1061400 | 1061597 | − | hypothetical protein Blon020220 |
| BI01268 | 1061748 | 1061894 | − | hypothetical protein |
| BI01730t | 1061882 | 1062055 | − | hypothetical protein Blon020217 |
| BI01269 | 1062779 | 1062997 | − | conserved hypothetical protein |
| BI01270 | 1063127 | 1063546 | + | Helix-turn-helix domain protein |
| BI01733t | 1064092 | 1064778 | + | conserved hypothetical protein |
| BI01271 | 1064862 | 1066490 | − | lipoprotein, putative |
| BI01272 | 1066742 | 1067959 | − | isocitrate dehydrogenase, NADP-dependent |
| BI01273 | 1068051 | 1069208 | + | IMP dehydrogenase family protein |
| BI01274 | 1069373 | 1069861 | + | hypothetical protein Blon020211 |
| BI01275 | 1069955 | 1072039 | + | long-chain-fatty-acid--CoA ligase, putative |
| BI01276 | 1072049 | 1072534 | + | polypeptide deformylase |
| BI01277 | 1072876 | 1073736 | + | ribosomal protein S2 |
| BI01278 | 1073818 | 1074666 | + | translation elongation factor Ts |
| BI01279 | 1074978 | 1075580 | + | uridylate kinase |
| BI01280 | 1075660 | 1076208 | + | ribosome recycling factor |
| BI01281 | 1076309 | 1077217 | + | phosphatidate cytidylyltransferase |
| BI01282 | 1077557 | 1078597 | + | radical SAM enzyme, Cfr family |
| BI01283 | 1078604 | 1079149 | − | protease I |
| BI01284 | 1079324 | 1080091 | + | imidazoleglycerol phosphate synthase, cyclase subunit |
| BI01285 | 1080228 | 1080620 | + | phosphoribosyl-AMP cyclohydrolase |
| BI01286 | 1080704 | 1082257 | + | anthranilate synthase component I |
| BI01287 | 1082328 | 1082564 | − | conserved hypothetical protein |
| BI01288 | 1082576 | 1084174 | + | ATP binding protein of ABC transporter |
| BI01289 | 1084221 | 1084925 | + | oxidoreductase, short-chain dehydrogenase/reductase family, putative |
| BI01290 | 1084999 | 1085364 | + | narrowly conserved protein with unknown function |
| BI01291 | 1085423 | 1086091 | − | conserved hypothetical protein |
| BI01292 | 1086091 | 1087701 | − | ABC transporter, ATP-binding protein |
| BI01293 | 1087704 | 1088600 | − | possible ABC transporter permease for cobalt |
| BI01294 | 1088405 | 1089049 | − | narrowly conserved protein with unknown function |
| BI01295 | 1089261 | 1090877 | + | conserved hypothetical protein |
| BI01296 | 1090916 | 1091548 | + | conserved hypothetical protein |
| BI01297 | 1091551 | 1095093 | + | hypothetical myosin-like protein with unknown function |
| BI01298 | 1095170 | 1096351 | + | conserved hypothetical protein |
| BI01299 | 1096680 | 1097084 | + | hypothetical protein BL0701 |
| BI01300 | 1097367 | 1100384 | + | excinuclease ABC, A subunit |
| BI01301 | 1100532 | 1102895 | + | excinuclease ABC, C subunit |
| BI01302 | 1103007 | 1103975 | + | aroE |
| BI01303 | 1103978 | 1104961 | + | Predicted P-loop-containing kinase |
| BI01304 | 1105247 | 1106110 | + | Uncharacterized BCR, COG1481 |
| BI01305 | 1106282 | 1107484 | + | phosphoglycerate kinase |
| BI01306 | 1107546 | 1108346 | + | triosephosphate isomerase |
| BI01307 | 1108365 | 1108658 | + | preprotein translocase, SecG subunit |
| BI01308 | 1108763 | 1109710 | + | L-lactate dehydrogenase |
| BI01309 | 1109710 | 1110558 | + | Cof family protein |
| BI01310 | 1110672 | 1112225 | + | aminotransferase, class I |
| BI01311 | 1112360 | 1113466 | − | membrane protein, putative |
| BI01312 | 1113642 | 1114943 | − | branched-chain amino acid transport system II carrier protein |
| BI01313 | 1115108 | 1116208 | − | transaldolase |
| BI01314 | 1116332 | 1118392 | − | transketolase |
| BI01315 | 1118812 | 1119927 | + | heat-inducible transcription repressor HrcA |
| BI01316 | 1119986 | 1121128 | + | dnaJ protein |
| BI01317 | 1121180 | 1121968 | − | COG3001: Uncharacterized BCR |
| BI01318 | 1122113 | 1122994 | + | undecaprenol kinase, putative |
| BI01319 | 1123157 | 1124146 | − | conserved hypothetical protein |
| BI01320 | 1124807 | 1126837 | + | threonyl-tRNA synthetase |
| BI01321 | 1127061 | 1127561 | + | HIT family protein |
| BI01322 | 1127703 | 1128455 | + | conserved hypothetical protein TIGR01033 |
| BI01323 | 1128464 | 1129045 | + | crossover junction endodeoxyribonuclease RuvC |
| BI01324 | 1129106 | 1129729 | + | Holliday junction DNA helicase RuvA |
| BI01325 | 1129732 | 1130793 | + | Holliday junction DNA helicase RuvB |
| BI01326 | 1130876 | 1131292 | + | preprotein translocase, YajC subunit |
| BI01327 | 1131359 | 1131937 | + | adenine phosphoribosyltransferase |

TABLE 1-continued

Open reading frames of the genome of UCC 35624.

| GeneID | Start | End | Strand | Description |
|---|---|---|---|---|
| BI01328 | 1132037 | 1133236 | + | succinyl-CoA synthetase, beta subunit |
| BI01329 | 1133239 | 1134147 | + | succinyl-CoA synthase, alpha subunit |
| BI01330 | 1133954 | 1135546 | + | membrane protein, putative |
| BI01331 | 1135497 | 1137131 | + | phosphoribosylaminoimidazolecarboxamide formyltransferase/IMP cyclohydrolase |
| BI01332 | 1137280 | 1137579 | + | hypothetical protein |
| BI01333 | 1137484 | 1138449 | − | aquaporin Z, putative |
| BI01334 | 1138645 | 1139412 | + | ribosomal large subunit pseudouridine synthase B |
| BI01335 | 1139514 | 1141538 | + | possible GTP-binding protein |
| BI01336 | 1141896 | 1143422 | + | UDP-glucose pyrophosphorylase |
| BI01337 | 1143565 | 1145475 | + | conserved hypothetical protein |
| BI01338 | 1145489 | 1145803 | + | hypothetical protein Blon020144 |
| BI01339 | 1145819 | 1148407 | + | helY |
| BI01340 | 1148524 | 1148868 | + | conserved hypothetical protein |
| BI01341 | 1149001 | 1149717 | + | hydrolase, haloacid dehalogenase-like family |
| BI01833t | 1149744 | 1149995 | + | conserved hypothetical protein |
| BI01342 | 1150135 | 1150497 | − | hypothetical protein Blon020140 |
| BI01343 | 1150673 | 1151302 | − | COG0789: Predicted transcriptional regulators |
| BI01344 | 1151406 | 1151846 | − | possible signal transduction protein |
| BI01345 | 1151856 | 1152596 | − | conserved hypothetical protein |
| BI01346 | 1152693 | 1153022 | − | small basic protein |
| BI01347 | 1153025 | 1153999 | − | conserved hypothetical protein |
| BI01348 | 1153992 | 1154684 | − | CDP-diacylglycerol--glycerol-3-phosphate 3-phosphatidyltransferase, putative |
| BI01349 | 1154623 | 1155471 | − | ATP phosphoribosyltransferase |
| BI01350 | 1155486 | 1155746 | − | phosphoribosyl-ATP pyrophosphohydrolase |
| BI01351 | 1155812 | 1156477 | − | ribulose-phosphate 3-epimerase |
| BI01352 | 1156556 | 1157500 | − | prolipoprotein diacylglyceryl transferase |
| BI01353 | 1157614 | 1158480 | − | tryptophan synthase, alpha subunit |
| BI01354 | 1158507 | 1160591 | − | tryptophan synthase, beta subunit |
| BI01355 | 1161120 | 1161968 | − | endonuclease IV |
| BI00066g | 1161414 | 1162400 | + | amino acid permease |
| BI01356 | 1162340 | 1162834 | + | amino acid permease |
| BI01357 | 1162503 | 1162667 | + | amino acid permease |
| BI01358 | 1163206 | 1164216 | − | hypothetical membrane protein with unknown function |
| BI01359 | 1164333 | 1164536 | − | hypothetical protein |
| BI01360 | 1164570 | 1164860 | − | abortive infection protein AbiGI, putative |
| BI01361 | 1164981 | 1165262 | + | hypothetical protein |
| BI01362 | 1165260 | 1165715 | − | lin2984 |
| BI01363 | 1165903 | 1166406 | + | acetyltransferase, GNAT family, putative |
| BI01364 | 1166567 | 1166746 | + | lin0863 |
| BI01365 | 1166793 | 1167323 | − | acetyltransferase, GNAT family |
| BI01366 | 1167392 | 1167961 | − | acetyltransferase, GNAT family |
| BI01367 | 1168315 | 1168992 | − | hypothetical protein |
| BI01368 | 1169017 | 1169823 | − | hypothetical protein |
| BI01369 | 1169832 | 1170527 | − | ABC transporter, ATP-binding protein |
| BI01370 | 1170352 | 1171263 | + | hypothetical Response regulator receiver domain |
| BI01371 | 1171317 | 1172225 | + | hypothetical protein |
| BI01372 | 1172194 | 1172631 | − | hypothetical Integral membrane protein |
| BI01373 | 1172956 | 1173576 | − | hypothetical protein |
| BI01374 | 1173576 | 1174301 | − | hypothetical protein |
| BI01873t | 1174309 | 1174962 | − | bacteriocin ABC transporter, ATP-binding protein, putative |
| BI01375 | 1175274 | 1176518 | + | IS30 family, transposase [imported] |
| BI01376 | 1176714 | 1177379 | − | DNA-binding response regulator |
| BI01377 | 1177379 | 1179001 | − | hypothetical ATPase, histidine kinase-, DNA gyrase B-, and HSP90-like domain protein |
| BI01378 | 1179039 | 1179881 | − | hypothetical permease, putative |
| BI01379 | 1180057 | 1180956 | − | ABC transporter, ATP-binding protein |
| BI01380 | 1181077 | 1181259 | + | hypothetical protein |
| BI01381 | 1181154 | 1181684 | − | hypothetical protein |
| BI01382 | 1182016 | 1182315 | + | BlsA |
| BI01383 | 1182321 | 1182662 | + | hypothetical protein |
| BI01384 | 1182847 | 1183050 | − | hypothetical protein |
| BI01385 | 1183324 | 1183446 | + | hypothetical protein BL0771 |
| BI01386 | 1183489 | 1183932 | + | hypothetical protein Blon020116 |
| BI01387 | 1183955 | 1184314 | − | COG0388: Predicted amidohydrolase |
| BI01388 | 1184376 | 1184531 | − | hypothetical protein |
| BI01389 | 1184840 | 1185853 | − | inner membrane protein, 60 kDa VC0004 [imported] |
| BI01390 | 1186097 | 1186555 | − | hypothetical protein |
| BI01391 | 1186942 | 1187067 | + | hypothetical protein |
| BI01392 | 1187122 | 1188783 | + | amino acid permease |
| BI01393 | 1188993 | 1189640 | − | Signal peptidase I |
| BI00067g | 1189800 | 1190303 | + | conserved hypothetical protein |

TABLE 1-continued

Open reading frames of the genome of UCC 35624.

| GeneID | Start | End | Strand | Description |
|---|---|---|---|---|
| BI01394 | 1189721 | 1190146 | − | hypothetical protein Blon020104 |
| BI01395 | 1190467 | 1191420 | + | lin0466 |
| BI01396 | 1191479 | 1191799 | + | narrowly conserved hypothetical protein |
| BI01397 | 1191887 | 1192165 | + | narrowly conserved hypothetical protein |
| BI01398 | 1192540 | 1193727 | + | Unknown, putative |
| BI01399 | 1193770 | 1195530 | + | YjeF family protein, putative |
| BI01400 | 1195635 | 1196261 | + | possible alpha beta hydrolase |
| BI01401 | 1196417 | 1197286 | + | transcriptional regulator, LysR family |
| BI01402 | 1197447 | 1198565 | − | conserved hypothetical protein |
| BI01403 | 1198783 | 1198932 | − | hypothetical protein |
| BI01404 | 1199044 | 1199736 | − | orotate phosphoribosyltransferase |
| BI01405 | 1199748 | 1200716 | − | dihydroorotate dehydrogenase |
| BI01406 | 1200722 | 1201543 | − | dihydroorotate dehydrogenase, electron transfer subunit |
| BI01407 | 1201682 | 1202632 | − | orotidine 5'-phosphate decarboxylase |
| BI01408 | 1202653 | 1203939 | − | dihydroorotase |
| BI01921t | 1204146 | 1204562 | − | Aspartate carbamoyltransferase regulatory chain, allosteric domain |
| BI01409 | 1204565 | 1205524 | − | aspartate carbamoyltransferase |
| BI01410 | 1205669 | 1208896 | − | glutamate-ammonia ligase adenylyltransferase family |
| BI01411 | 1208955 | 1209905 | − | EF0040 |
| BI01412 | 1210042 | 1210893 | − | 5,10-methylenetetrahydrofolate reductase |
| BI01413 | 1210955 | 1213255 | − | 5-methyltetrahydropteroyltriglutamate--homocysteine S-methyltransferase |
| BI01414 | 1213369 | 1213923 | − | phosphohistidine phosphatase SixA, putative |
| BI01415 | 1214024 | 1215091 | − | conserved hypothetical protein |
| BI01416 | 1215168 | 1215803 | + | serine esterase, putative |
| BI01417 | 1215850 | 1216806 | − | oxidoreductase, aldo/keto reductase 2 family |
| BI01418 | 1217063 | 1217995 | + | lipC, putative |
| BI01419 | 1218234 | 1219178 | + | hypothetical oxidoreductase, zinc-binding dehydrogenase family |
| BI01420 | 1219340 | 1219642 | − | probable ATP binding protein of ABC transporter |
| BI01421 | 1220459 | 1221484 | + | transposase (25) BH3998 [imported], putative |
| BI00069g | 1221277 | 1221948 | + | hypothetical protein |
| BI01422 | 1221948 | 1222706 | + | Tpase2 |
| BI01423 | 1222896 | 1223972 | + | hypothetical protein |
| BI01424 | 1224236 | 1224811 | + | hypothetical protein |
| BI01425 | 1224888 | 1225190 | − | transcriptional regulator, HTH_3 family |
| BI01426 | 1225221 | 1226144 | − | hypothetical protein |
| BI01427 | 1226238 | 1227140 | − | hypothetical protein |
| BI01428 | 1227158 | 1228765 | − | hypothetical protein |
| BI01429 | 1229279 | 1230097 | − | hypothetical ADP-ribosylglycohydrolase |
| BI01430 | 1231271 | 1231726 | − | hypothetical protein |
| BI01431 | 1232085 | 1232906 | + | conserved hypothetical protein |
| BI01432 | 1233000 | 1233539 | − | bcp |
| BI01433 | 1233681 | 1234511 | − | probable amidase [imported] |
| BI01434 | 1234511 | 1235365 | − | hydrolase, haloacid dehalogenase-like family, putative |
| BI01435 | 1235520 | 1236365 | − | amino acid transport protein |
| BI01436 | 1236462 | 1237709 | − | possible glycosyltransferase |
| BI01437 | 1237841 | 1238302 | − | conserved hypothetical protein |
| BI01438 | 1238382 | 1239917 | − | gltD |
| BI01439 | 1239922 | 1244265 | − | Conserved region in glutamate synthase family |
| BI01440 | 1244835 | 1245116 | + | transcription regulator, LacI family [imported] |
| BI01441 | 1245175 | 1246197 | − | conserved hypothetical protein |
| BI01442 | 1246656 | 1246979 | + | conserved hypothetical protein |
| BI01443 | 1247042 | 1247227 | − | hypothetical protein |
| BI01444 | 1247493 | 1248536 | − | transcriptional regulator, LacI family, putative |
| BI01445 | 1249246 | 1250073 | + | conserved hypothetical protein |
| BI01446 | 1250275 | 1250571 | − | hypothetical protein |
| BI00071g | 1250541 | 1250888 | − | conserved hypothetical protein |
| BI01447 | 1250658 | 1250807 | + | hypothetical protein |
| BI01448 | 1251252 | 1252538 | + | MATE efflux family protein, putative |
| BI01449 | 1252678 | 1252794 | − | hypothetical protein |
| BI01450 | 1253083 | 1254216 | + | IS30 family, transposase [imported] |
| BI01451 | 1254323 | 1255327 | − | glycerate kinase |
| BI01452 | 1255679 | 1256734 | + | transcriptional regulator, LacI family, putative |
| BI01453 | 1256820 | 1258094 | − | oxygen-independent coproporphyrinogen III oxidase, putative |
| BI01454 | 1258229 | 1259890 | − | GTP-binding protein LepA |
| BI01455 | 1260253 | 1260510 | + | ribosomal protein S20 |
| BI01456 | 1260768 | 1261556 | − | conserved hypothetical transmembrane protein with unknown function |
| BI01457 | 1261807 | 1262703 | − | transcriptional regulator, MazG family |
| BI01458 | 1262903 | 1264027 | − | branched-chain amino acid aminotransferase |

TABLE 1-continued

Open reading frames of the genome of UCC 35624.

| GeneID | Start | End | Strand | Description |
|---|---|---|---|---|
| BI01459 | 1264254 | 1264871 | − | ribosomal 5S rRNA E-loop binding protein Ctc/L25/TL5 |
| BI01460 | 1265298 | 1266332 | + | conserved hypothetical protein |
| BI01461 | 1266474 | 1267895 | − | NAD(P) transhydrogenase, beta subunit [imported] |
| BI01462 | 1267898 | 1268200 | − | NAD(P) transhydrogenase, alpha subunit |
| BI01463 | 1268219 | 1269379 | − | NAD(P) transhydrogenase, alpha subunit [imported] |
| BI01464 | 1269798 | 1271828 | + | long-chain-fatty-acid--CoA ligase |
| BI01465 | 1271887 | 1272948 | − | GTP-binding protein Era |
| BI01466 | 1272953 | 1274383 | − | CBS domain protein |
| BI01467 | 1274462 | 1275052 | − | conserved hypothetical protein TIGR00043 |
| BI01468 | 1275000 | 1276172 | − | PhoH family protein |
| BI01469 | 1276194 | 1276529 | − | Hit family protein |
| BI01470 | 1276581 | 1277375 | − | conserved hypothetical protein TIGR00046 |
| BI01471 | 1277619 | 1278494 | + | spoU rRNA methylase family protein |
| BI01472 | 1278758 | 1279939 | + | glucose-1-phosphate adenylyltransferase |
| BI01473 | 1280035 | 1280532 | − | mrp protein homolog |
| BI01474 | 1280635 | 1281171 | − | SUF system FeS assembly protein, NifU family |
| BI01475 | 1281201 | 1282472 | − | aminotransferase, class-V |
| BI01476 | 1282614 | 1283390 | − | FeS assembly ATPase SufC |
| BI01477 | 1283419 | 1284651 | − | FeS assembly protein SufD |
| BI01478 | 1284660 | 1286156 | − | FeS assembly protein SufB |
| BI01479 | 1286383 | 1287849 | − | conserved hypothetical protein |
| BI01480 | 1288225 | 1289883 | − | CTP synthase |
| BI01481 | 1290032 | 1291585 | − | dipeptidase, putative |
| BI01482 | 1291684 | 1292127 | − | 3-dehydroquinate dehydratase, type II |
| BI01483 | 1292294 | 1293835 | − | 3-dehydroquinate synthase |
| BI01484 | 1293999 | 1295132 | − | chorismate synthase |
| BI01485 | 1295247 | 1295717 | + | COG0477: Permeases of the major facilitator superfamily |
| BI01486 | 1295891 | 1297003 | − | Uncharacterized BCR, YceG family COG1559 |
| BI01487 | 1297083 | 1297535 | − | conserved hypothetical protein TIGR00250 |
| BI01488 | 1297550 | 1300228 | − | alanyl-tRNA synthetase |
| BI01489 | 1300359 | 1300592 | − | hypothetical protein Blon020010 |
| BI01490 | 1300595 | 1300990 | − | conserved hypothetical protein |
| BI01491 | 1301196 | 1301921 | − | phosphoglycerate mutase |
| BI01492 | 1302158 | 1304008 | + | Acyltransferase family domain protein |
| BI01493 | 1304105 | 1304728 | − | ribosomal protein S4 |
| BI01494 | 1304930 | 1305895 | − | ABC transporter, ATP-binding protein |
| BI01495 | 1305900 | 1307114 | − | hypothetical transmembrane protein with unknown function |
| BI01496 | 1307208 | 1307603 | − | conserved hypothetical protein |
| BI01497 | 1307751 | 1310450 | − | hypothetical UvrD/REP helicase |
| BI01498 | 1310567 | 1311145 | + | xanthine phosphoribosyltransferase |
| BI01499 | 1311199 | 1312560 | + | xanthine/uracil permease family protein |
| BI01500 | 1312696 | 1312902 | − | transcription regulator, Cro/CI family [imported]-related protein |
| BI01501 | 1312912 | 1313169 | − | hypothetical protein |
| BI01502 | 1313326 | 1314144 | − | hydrolase, alpha/beta fold family, putative |
| BI01503 | 1314432 | 1315367 | + | conserved hypothetical protein |
| BI01504 | 1315462 | 1315860 | − | glyoxalase family protein |
| BI01505 | 1316019 | 1316630 | + | isochorismatase |
| BI01506 | 1316885 | 1318360 | + | conserved hypothetical protein |
| BI01507 | 1318371 | 1319780 | − | membrane protein, putative |
| BI01508 | 1319770 | 1321005 | − | membrane protein, putative |
| BI01509 | 1321109 | 1322089 | − | daunorubicin resistance ATP-binding protein |
| BI01510 | 1322192 | 1322296 | − | hypothetical protein |
| BI01511 | 1322475 | 1323824 | + | histidine kinase sensor of two-component system |
| BI01512 | 1323917 | 1324477 | + | DNA-binding response regulator |
| BI01513 | 1324667 | 1325287 | − | Protein of unknown function subfamily |
| BI01514 | 1325308 | 1326324 | − | phosphate transporter family protein |
| BI01515 | 1326480 | 1326674 | − | conserved hypothetical protein |
| BI01516 | 1326735 | 1329005 | − | carbon starvation protein A |
| BI01517 | 1329406 | 1330668 | + | glycosyl hydrolase, family 13, putative |
| BI01518 | 1330703 | 1331404 | − | transcriptional regulator, TetR family, putative |
| BI01519 | 1331486 | 1333669 | − | possible ATP-dependent RNA helicase |
| BI01520 | 1334052 | 1335338 | − | uracil-xanthine permease |
| BI01521 | 1335446 | 1336273 | − | phosphoglycerate mutase family domain protein |
| BI01522 | 1336327 | 1336905 | − | conserved hypothetical protein |
| BI01523 | 1337061 | 1337612 | + | conserved hypothetical protein |
| BI01524 | 1337738 | 1338898 | − | conserved hypothetical protein |
| BI01525 | 1339275 | 1340816 | − | conserved hypothetical protein |
| BI01526 | 1341250 | 1341687 | + | hypothetical COG0653: Preprotein translocase subunit SecA (ATPase, RNA helicase) |

TABLE 1-continued

Open reading frames of the genome of UCC 35624.

| GeneID | Start | End | Strand | Description |
|---|---|---|---|---|
| BI01527 | 1341752 | 1343449 | + | Protein kinase domain protein |
| BI01528 | 1343493 | 1344980 | − | permease, putative |
| BI01529 | 1345295 | 1347565 | − | drug resistance transporter, EmrB/QacA subfamily |
| BI01530 | 1347576 | 1347776 | − | hypothetical protein |
| BI01531 | 1347947 | 1348309 | + | hypothetical Domain of unknown function (DUF307) |
| BI01532 | 1348405 | 1349910 | − | hypothetical protein |
| BI01533 | 1349906 | 1351072 | − | hypothetical protein |
| BI01534 | 1351166 | 1351474 | − | hypothetical protein |
| BI02085t | 1351280 | 1351477 | + | hypothetical protein Blon021394 |
| BI01535 | 1351807 | 1352478 | + | COG4186: Predicted phosphoesterase or phosphohydrolase |
| BI01536 | 1352565 | 1354004 | + | conserved hypothetical protein |
| BI01537 | 1354044 | 1354253 | + | hypothetical protein BL0925 |
| BI01538 | 1354253 | 1354612 | + | hypothetical protein BL0925 |
| BI01539 | 1354729 | 1355193 | + | hypothetical protein |
| BI01540 | 1355496 | 1356380 | − | hypothetical protein |
| BI01541 | 1356380 | 1357450 | − | hypothetical Phage integrase family |
| BI01542 | 1357650 | 1358675 | + | transposase (25) BH3998 [imported], putative |
| BI00076g | 1358468 | 1359139 | + | hypothetical protein |
| BI01543 | 1359139 | 1359897 | + | Tpase2 |
| BI01544 | 1360305 | 1361546 | − | GTP-binding protein YchF |
| BI01545 | 1361533 | 1362351 | − | pyrroline-5-carboxylate reductase |
| BI01546 | 1362416 | 1363891 | − | proline iminopeptidase |
| BI01547 | 1363977 | 1366433 | + | histidine kinase sensor of two-component system |
| BI01548 | 1366551 | 1367345 | + | DNA-binding response regulator |
| BI01549 | 1367384 | 1370233 | − | possible transport protein |
| BI01550 | 1370265 | 1371176 | − | ABC transporter, ATP-binding protein |
| BI01551 | 1371528 | 1372841 | − | O-acetylhomoserine sulfhydrylase |
| BI01552 | 1373315 | 1374184 | + | pyridoxal kinase, putative |
| BI01553 | 1374424 | 1374924 | + | conserved hypothetical protein TIGR00252 |
| BI01554 | 1374983 | 1376515 | + | Mg chelatase-related protein |
| BI01555 | 1376515 | 1378212 | + | DNA processing protein DprA, putative |
| BI01556 | 1378272 | 1380134 | + | sdhA |
| BI01557 | 1380233 | 1381195 | + | sdhB |
| BI01558 | 1381277 | 1381954 | + | probable methyltransferase |
| BI01559 | 1382006 | 1382944 | − | conserved hypothetical protein TIGR00730 |
| BI01560 | 1383180 | 1384595 | − | Na+/H+ antiporter [imported] |
| BI01561 | 1385070 | 1386485 | − | ATP-dependent Clp protease, ATP-binding subunit ClpX |
| BI01562 | 1386610 | 1387308 | − | ATP-dependent Clp protease, proteolytic subunit ClpP |
| BI01563 | 1387317 | 1387907 | − | ATP-dependent Clp protease, proteolytic subunit ClpP |
| BI01564 | 1388046 | 1388423 | − | hypothetical protein Blon021418 |
| BI01565 | 1388538 | 1390001 | − | voltage-gated chloride channel family protein, putative |
| BI01566 | 1390189 | 1391565 | − | trigger factor |
| BI01567 | 1391623 | 1392921 | − | 3-5 exonuclease domain protein |
| BI01568 | 1392921 | 1393730 | − | COG0477: Permeases of the major facilitator superfamily |
| BI01569 | 1393622 | 1394500 | − | pyruvate formate-lyase 1 activating enzyme |
| BI01570 | 1394613 | 1396985 | − | formate acetyltransferase |
| BI01571 | 1397254 | 1397475 | − | conserved hypothetical protein |
| BI01572 | 1397531 | 1399093 | − | NH(3)-dependent NAD+ synthetase |
| BI01573 | 1399577 | 1400725 | − | Peptidase, M20/M25/M40 family |
| BI01574 | 1400817 | 1401500 | − | permease protein of ABC transporter system |
| BI01575 | 1401500 | 1402702 | − | ABC transporter, ATP-binding protein |
| BI01576 | 1402839 | 1403816 | − | lipoprotein, YaeC family |
| BI01577 | 1404020 | 1404847 | + | hydrolase, haloacid dehalogenase-like family |
| BI01578 | 1404975 | 1407449 | − | D-xylulose 5-phosphate/D-fructose 6-phosphate phosphoketolase |
| BI01579 | 1407895 | 1409454 | + | GMP synthase |
| BI01580 | 1409723 | 1410304 | + | COG0798: Arsenite efflux pump ACR3 and related permeases |
| BI01581 | 1410343 | 1410720 | + | arsenical resistance protein/arsenate reductase |
| BI01582 | 1411265 | 1411771 | + | hypothetical Transposase IS66 family |
| BI00078g | 1411579 | 1412214 | + | hypothetical protein Blon021471 |
| BI01583 | 1412111 | 1413136 | + | transposase (25) BH3998 [imported], putative |
| BI00079g | 1412929 | 1413600 | + | hypothetical protein |
| BI01584 | 1413600 | 1414358 | + | Tpase2 |
| BI01585 | 1414423 | 1414911 | + | hypothetical COG3436: Transposase and inactivated derivatives |
| BI02159t | 1415037 | 1416323 | − | COG0477: Permeases of the major facilitator superfamily |

TABLE 1-continued

Open reading frames of the genome of UCC 35624.

| GeneID | Start | End | Strand | Description |
|---|---|---|---|---|
| BI01586 | 1416510 | 1417160 | + | putative ATP-binding protein |
| BI01587 | 1417164 | 1418444 | + | Uncharacterized conserved protein |
| BI01588 | 1418440 | 1418820 | + | hypothetical protein Blon021466 |
| BI01589 | 1418965 | 1420548 | + | conserved hypothetical protein |
| BI01590 | 1420796 | 1422598 | + | acyltransferase, putative |
| BI01591 | 1422687 | 1423706 | + | prsA |
| BI01592 | 1423991 | 1425370 | + | UDP-N-acetylglucosamine pyrophosphorylase |
| BI01593 | 1425377 | 1425787 | + | iojap-related protein |
| BI01594 | 1425942 | 1426637 | + | phosphoglycerate mutase, putative |
| BI01595 | 1427363 | 1428961 | + | phosphate acetyltransferase |
| BI01596 | 1429099 | 1429695 | + | acetate kinase |
| BI01597 | 1429811 | 1430326 | + | hypothetical COG0282: Acetate kinase |
| BI01598 | 1430503 | 1431867 | − | 3-phosphoshikimate 1-carboxyvinyltransferase |
| BI01599 | 1431867 | 1433036 | − | membrane protein, putative |
| BI01600 | 1433757 | 1434125 | − | hypothetical COG2217: Cation transport ATPase |
| BI01601 | 1434688 | 1436172 | − | galactoside symporter |
| BI01602 | 1436515 | 1439583 | + | beta-galactosidase, putative |
| BI01603 | 1440389 | 1441246 | + | hypothetical protein |
| BI01604 | 1441301 | 1441966 | − | hypothetical protein Blon020709 |
| BI01605 | 1442167 | 1442559 | − | hypothetical protein |
| BI01606 | 1442574 | 1442990 | − | hypothetical protein |
| BI01607 | 1442990 | 1444792 | − | hypothetical protein |
| BI01608 | 1444688 | 1445566 | + | COG3757: Lyzozyme M1 (1,4-beta-N-acetylmuramidase) |
| BI01609 | 1445667 | 1445948 | + | hypothetical protein |
| BI01610 | 1446119 | 1446796 | + | hypothetical protein |
| BI01611 | 1447212 | 1448801 | + | hypothetical C-5 cytosine-specific DNA methylase |
| BI01612 | 1448804 | 1449997 | − | hypothetical protein Psyc022392 |
| BI01613 | 1450130 | 1450393 | + | hypothetical protein |
| BI01614 | 1450514 | 1450891 | − | hypothetical protein |
| BI01615 | 1451253 | 1452203 | − | hypothetical protein |
| BI01616 | 1452503 | 1452802 | − | TnpB |
| BI01617 | 1452909 | 1453127 | + | IS861, transposase OrfB |
| BI01618 | 1453248 | 1453586 | + | putative transposase subunit |
| BI01619 | 1455179 | 1455604 | − | cell division protein FtsZ |
| BI01620 | 1455752 | 1459864 | − | hypothetical UvrD/REP helicase |
| BI01621 | 1459861 | 1463163 | − | COG3857: ATP-dependent nuclease, subunit B |
| BI01622 | 1463295 | 1465877 | − | hypothetical DNA polymerase III, alpha subunit |
| BI01623 | 1466012 | 1467055 | + | conserved hypothetical protein |
| BI01624 | 1467089 | 1467886 | − | narrowly conserved hypothetical membrane protein |
| BI01625 | 1468160 | 1468507 | − | hypothetical protein BL0124 |
| BI01626 | 1468949 | 1469908 | − | Pseudouridylate synthases, 23S RNA-specific |
| BI01627 | 1469911 | 1470456 | − | lipoprotein signal peptidase |
| BI01628 | 1470481 | 1471857 | − | conserved hypothetical protein |
| BI01629 | 1472000 | 1472299 | − | COG0762: Predicted integral membrane protein |
| BI01630 | 1472424 | 1472900 | − | conserved hypothetical protein |
| BI01631 | 1472916 | 1473830 | − | hypothetical Tubulin/FtsZ family, C-terminal domain |
| BI01632 | 1474239 | 1475480 | − | TIM-barrel protein, NifR3 family |
| BI01633 | 1475628 | 1476938 | − | glycyl-tRNA synthetase |
| BI01634 | 1477533 | 1478474 | + | hydroxyethylthiazole kinase |
| BI01635 | 1478743 | 1481310 | + | thiamine biosynthesis protein ThiC |
| BI01636 | 1481353 | 1481679 | − | hypothetical protein |
| BI01637 | 1481820 | 1482626 | + | phosphomethylpyrimidine kinase |
| BI01638 | 1482680 | 1483054 | + | COG0011: Uncharacterized ACR |
| BI01639 | 1483563 | 1484939 | + | permease, putative |
| BI02235t | 1485571 | 1485978 | + | conserved hypothetical protein |
| BI01640 | 1486039 | 1487433 | + | Serpin (serine protease inhibitor) superfamily |
| BI01641 | 1487717 | 1488517 | + | transcriptional regulator, LacI family, putative |
| BI01642 | 1488728 | 1490068 | + | sucrose transport protein |
| BI01643 | 1490082 | 1491635 | + | sucrose-6-phosphate hydrolase, putative |
| BI01644 | 1491833 | 1492612 | + | ABC transporter, permease protein, cysTW family, putative |
| BI01645 | 1492927 | 1493943 | + | pyrimidine precursor biosynthesis enzyme, putative |
| BI02246t | 1494070 | 1495254 | + | inosine-uridine preferring nucleoside hydrolase |
| BI01646 | 1495416 | 1496207 | − | undecaprenyl diphosphate synthase |
| BI01647 | 1496207 | 1496923 | − | DNA repair protein RecO |
| BI01648 | 1496975 | 1498684 | − | conserved hypothetical protein |
| BI01649 | 1498808 | 1500028 | − | 1-hydroxy-2-methyl-2-(E)-butenyl 4-diphosphate synthase |
| BI01650 | 1500028 | 1501215 | − | 1-deoxy-D-xylulose 5-phosphate reductoisomerase |

TABLE 1-continued

Open reading frames of the genome of UCC 35624.

| GeneID | Start | End | Strand | Description |
|---|---|---|---|---|
| BI01651 | 1501215 | 1502915 | − | conserved hypothetical protein |
| BI01652 | 1503387 | 1503809 | − | conserved hypothetical protein |
| BI01653 | 1503919 | 1504797 | − | PDZ domain family protein |
| BI01654 | 1505129 | 1506760 | + | conserved hypothetical protein |
| BI01655 | 1506836 | 1508407 | − | ATP-dependent DNA helicase PcrA |
| BI01656 | 1508553 | 1510205 | + | conserved hypothetical protein |
| BI01657 | 1510357 | 1510578 | + | putative ATP-binding protein |
| BI01658 | 1510645 | 1511535 | − | PHP domain N-terminal region family |
| BI01659 | 1511673 | 1512407 | + | narrowly conserved hypothetical transmembrane protein |
| BI01660 | 1512419 | 1513309 | − | diaminopimelate epimerase |
| BI01661 | 1513417 | 1514208 | + | glutamate racemase |
| BI01662 | 1514340 | 1515182 | + | Patatin family |
| BI01663 | 1515255 | 1516151 | − | Unknown |
| BI01664 | 1516314 | 1516580 | − | trans-sulfuration enzyme |
| BI00087g | 1516749 | 1517024 | − | ABC transporter, ATP-binding protein, putative |
| BI00086g | 1517139 | 1517573 | + | conserved hypothetical protein in upf0074 |
| BI01665 | 1517692 | 1517940 | − | conserved hypothetical protein |
| BI01666 | 1518187 | 1519422 | − | cystathionine beta-lyase |
| BI01667 | 1519661 | 1520560 | − | glutamine ABC transporter, periplasmic glutamine-binding protein (glnH) |
| BI01668 | 1520629 | 1521417 | − | amino acid ABC transporter, ATP-binding protein |
| BI01669 | 1521413 | 1521952 | − | amino acid ABC transporter, permease protein SP0710 [imported] |
| BI01670 | 1522074 | 1522730 | − | amino acid ABC transporter, permease protein |
| BI01671 | 1522793 | 1523605 | + | hypothetical Phospholipase/Carboxylesterase |
| BI01672 | 1523620 | 1525872 | − | Tn916, tetracycline resistance protein, putative |
| BI01673 | 1526091 | 1526723 | + | DNA polymerase III, epsilon subunit |
| BI01674 | 1526731 | 1527318 | − | guanylate kinase |
| BI01675 | 1527501 | 1528418 | − | orotidine 5'-phosphate decarboxylase, putative |
| BI01676 | 1528421 | 1531801 | − | carbamoyl-phosphate synthase, large subunit |
| BI01677 | 1531806 | 1533176 | − | carbamoyl-phosphate synthase, small subunit |
| BI01678 | 1533219 | 1533788 | − | transcription antitermination factor NusB |
| BI01679 | 1533846 | 1534154 | − | Elongation factor P (EF-P) |
| BI01680 | 1534514 | 1535248 | + | Unknown, putative |
| BI01681 | 1535248 | 1536033 | + | conserved hypothetical protein TIGR00245 |
| BI01682 | 1536066 | 1536770 | − | Unknown |
| BI01683 | 1536878 | 1539436 | − | hypothetical EAL domain |
| BI01684 | 1539444 | 1540751 | − | Probable hydrolase transmembrane protein |
| BI01685 | 1541332 | 1543257 | + | glycosyltransferase |
| BI01686 | 1543387 | 1543551 | − | hypothetical protein |
| BI01687 | 1543710 | 1544600 | − | 3-hydroxyacyl-CoA dehydrogenase |
| BI01688 | 1544959 | 1546782 | − | alpha-xylosidase |
| BI01689 | 1546897 | 1547199 | − | hypothetical COG1653: ABC-type sugar transport system, periplasmic component |
| BI01690 | 1547359 | 1549491 | − | possible beta-hexosaminidase A |
| BI01691 | 1549605 | 1550417 | − | ABC transporter, permease protein, MalFG family |
| BI01692 | 1551035 | 1551862 | + | conserved hypothetical protein |
| BI01693 | 1552142 | 1553254 | − | mrp |
| BI01694 | 1553434 | 1556193 | − | DNA ligase, NAD-dependent |
| BI01695 | 1556261 | 1559881 | − | conserved hypothetical protein |
| BI01696 | 1560102 | 1562237 | + | membrane protein, putative |
| BI01697 | 1562555 | 1564141 | + | hypothetical protein Blon021196 |
| BI01698 | 1564204 | 1564977 | − | ABC transporter, ATP-binding protein, putative |
| BI01699 | 1565037 | 1566299 | − | aminotransferase, class I, putative |
| BI01700 | 1566573 | 1567337 | − | ROK family protein |
| BI01701 | 1567583 | 1568365 | + | Nitroreductase family protein |
| BI01702 | 1568413 | 1569423 | − | probable glycosyltransferase |
| BI01703 | 1569675 | 1570325 | + | conserved hypothetical protein |
| BI01704 | 1570459 | 1572888 | + | ABC transporter, ATP-binding protein, putative |
| BI01705 | 1572963 | 1573265 | + | Predicted RNA-binding protein containing KH domain |
| BI01706 | 1573370 | 1573732 | − | conserved hypothetical protein |
| BI01707 | 1573842 | 1574456 | + | hypothetical TM2 domain |
| BI01708 | 1574885 | 1575301 | + | hypothetical protein Blon021592 |
| BI01709 | 1575432 | 1576415 | − | D-isomer specific 2-hydroxyacid dehydrogenase family protein |
| BI01710 | 1576714 | 1578168 | + | drug resistance transporter, EmrB/QacA family, putative |
| BI01711 | 1578399 | 1579418 | − | ribose ABC transporter, permease protein VCA0129 [imported], putative |
| BI01712 | 1579418 | 1580485 | − | ribose ABC transporter, permease protein VCA0129 [imported], putative |

TABLE 1-continued

Open reading frames of the genome of UCC 35624.

| GeneID | Start | End | Strand | Description |
| --- | --- | --- | --- | --- |
| BI01713 | 1580490 | 1582028 | − | ATP binding protein of ABC transporter |
| BI01714 | 1582172 | 1583152 | − | ribose ABC transporter, periplasmic D-ribose-binding protein |
| BI01715 | 1583472 | 1585199 | − | lipoprotein, putative |
| BI01716 | 1585199 | 1586752 | − | sensor histidine kinase MtrB |
| BI01717 | 1586893 | 1587837 | − | hypothetical Response regulator receiver domain |
| BI01718 | 1587674 | 1589005 | − | conserved ATP/GTP binding protein |
| BI01719 | 1589136 | 1591535 | − | COG0513: Superfamily II DNA and RNA helicases |
| BI01720 | 1591837 | 1592907 | − | Domain of unknown function (DUF344) family |
| BI02350t | 1592976 | 1593215 | − | conserved hypothetical protein |
| BI01721 | 1593208 | 1593801 | − | COG0737: 5'-nucleotidase/2',3'-cyclic phosphodiesterase and related esterases |
| BI01722 | 1593841 | 1595364 | − | hypothetical secreted protein with probable acid phosphatase domain |
| BI01723 | 1595471 | 1596568 | − | glutamine ABC transporter, glutamine-binding protein/permease protein, putative |
| BI01724 | 1596577 | 1597251 | − | glutamine ABC transporter, permease protein |
| BI01725 | 1597254 | 1598090 | − | amino acid ABC transporter, amino acid-binding protein, putative |
| BI01726 | 1598125 | 1598964 | − | amino acid ABC transporter, ATP-binding protein |
| BI01727 | 1599401 | 1600468 | + | conserved hypothetical protein |
| BI01728 | 1600932 | 1602728 | − | aspartyl-tRNA synthetase |
| BI01729 | 1602767 | 1604107 | − | histidyl-tRNA synthetase |
| BI01730 | 1604264 | 1605721 | + | conserved hypothetical protein |
| BI01731 | 1605933 | 1607723 | − | 5'-nucleotidase family protein, putative |
| BI01732 | 1607898 | 1608653 | − | creatinine amidohydrolase, creatininase |
| BI01733 | 1608742 | 1610115 | − | proline/betaine transporter |
| BI01734 | 1610158 | 1610328 | + | hypothetical protein |
| BI01735 | 1610308 | 1611378 | − | hypothetical protein weakly similar to putative transcriptional regulator from Streptomyces |
| BI01736 | 1611950 | 1613266 | + | N-acyl-D-amino-acid deacylase family protein, putative |
| BI01737 | 1613452 | 1616058 | − | ATP-dependent Clp protease, ATP-binding subunit ClpC |
| BI01738 | 1616208 | 1617170 | + | demannu, putative |
| BI01739 | 1617288 | 1618208 | − | hypothetical protein Blon021510 |
| BI01740 | 1618484 | 1618870 | − | cspB |
| BI01741 | 1618943 | 1620931 | − | sensor histidine kinase |
| BI01742 | 1620965 | 1621738 | − | DNA-binding response regulator |
| BI01743 | 1621689 | 1622492 | − | conserved hypothetical protein |
| BI01744 | 1622567 | 1622854 | + | conserved hypothetical protein |
| BI01745 | 1622957 | 1624579 | − | chaperone |
| BI01746 | 1624820 | 1625056 | − | cold-shock domain family protein |
| BI01747 | 1625289 | 1625870 | − | hypothetical protein Blon020592 |
| BI01748 | 1626163 | 1626771 | + | uracil-DNA glycosylase |
| BI01749 | 1626814 | 1627890 | + | ATPase, MoxR family |
| BI01750 | 1628022 | 1628837 | + | Protein of unknown function family |
| BI01751 | 1628840 | 1629388 | + | conserved hypothetical protein |
| BI01752 | 1629388 | 1630443 | + | conserved hypothetical protein |
| BI01753 | 1630443 | 1631471 | + | conserved hypothetical protein |
| BI01754 | 1631444 | 1632070 | + | platelet binding protein GspB, putative |
| BI01755 | 1632316 | 1632660 | + | conserved hypothetical protein |
| BI01756 | 1632660 | 1634261 | + | conserved hypothetical protein |
| BI01757 | 1634531 | 1634893 | + | conserved hypothetical protein |
| BI01758 | 1635034 | 1635672 | − | hypothetical membrane protein with unknown function |
| BI01759 | 1635805 | 1637238 | + | adenylosuccinate lyase VC1126 [imported] |
| BI01760 | 1637373 | 1639931 | + | narrowly conserved hypothetical membrane protein |
| BI01761 | 1640080 | 1640358 | + | DNA-binding protein HU |
| BI01762 | 1640480 | 1641937 | − | possible DNA-binding protein |
| BI01763 | 1641940 | 1642203 | − | hypothetical Protein of unknown function (DUF797) |
| BI01764 | 1642234 | 1643133 | − | possible inositol monophosphatase |
| BI01765 | 1643139 | 1644803 | − | hypothetical proteasome-associated protein |
| BI01766 | 1644828 | 1646390 | − | cell division control protein 48, AAA family |
| BI01767 | 1646454 | 1647149 | − | DedA family protein |
| BI01768 | 1647410 | 1647919 | + | phosphoserine phosphatase SerB |
| BI01769 | 1648166 | 1650271 | + | primosomal protein N |
| BI01770 | 1650333 | 1651034 | + | possible alpha beta hydrolase |
| BI01771 | 1651061 | 1652044 | + | methionyl-tRNA formyltransferase |
| BI01772 | 1652142 | 1653908 | − | dihydroxy-acid dehydratase |
| BI01773 | 1654203 | 1654484 | + | DNA-directed RNA polymerase, omega subunit |

TABLE 1-continued

Open reading frames of the genome of UCC 35624.

| GeneID | Start | End | Strand | Description |
|---|---|---|---|---|
| BI01774 | 1654765 | 1655982 | + | S-adenosylmethionine synthetase |
| BI02420t | 1656352 | 1657425 | + | hypothetical protein CV1232 |

The Open reading frames (ORF) listed in Table 1 are defined by their position in the genomic sequence of SEQ ID No. 1. For example BI00001 is defined by the nucleotide sequence of base numbers 1667321 and 1667608 (inclusive) of SEQ ID No. 1.

EXAMPLES

The following examples further describe and demonstrate embodiments within the scope of the invention. The examples are given solely for the purpose of illustration and are not to be construed as limitations of the present invention, as many variations thereof are possible without departing from the spirit and scope of the invention.

Example 1

Isolation of *Bifidobacterium Longum* Biotype Infantis UCC 35624

Appendices and sections of the large and small intestine of the human G.I.T., obtained during reconstructive surgery, were screened for probiotic bacterial strains. All samples were stored immediately after surgery at −80° C. in sterile containers. Frozen tissues were thawed, weighed and placed in cysteinated (0.05%) one quarter strength Ringers' solution. Each sample was gently shaken to remove loosely adhering microorganisms. Following transfer to a second volume of Ringers' solution, the sample was vortexed for 7 min to remove tightly adhering bacteria. In order to isolate tissue embedded bacteria, samples were also homogenised in a Braun blender. The solutions were serially diluted and spread-plated (100 µl) on to the following agar media: RCM (reinforced clostridial media) and RCM adjusted to pH 5.5 using acetic acid; TPY (trypticase, peptone and yeast extract), Chevalier, P. et al. (1990). MRS (deMann, Rogosa and Sharpe); ROG (acetate medium (SL) of Rogosa); LLA (Liver-lactose agar of Lapiere); BHI (brain heart infusion agar); LBS (*Lactobacillus* selective agar) and TSAYE (tryptone soya agar supplemented with 0.6% yeast extract). All agar media was supplied by Oxoid Chemicals with the exception of TPY agar. Plates were incubated in anaerobic jars (BBL, Oxoid) using $CO_2$ generating kits (Anaerocult A, Merck) for 2-5 days at 37° C.

Gram positive, catalase negative rod-shaped or bifurcated/pleomorphic bacteria isolates were streaked for purity on to complex non-selective media (TPY). Isolates were routinely cultivated in TPY medium unless otherwise stated at 37° C. under anaerobic conditions. *Bifidobacteria* species were stocked in 40% glycerol and stored at −20° and −80° C.

Approximately fifteen hundred catalase negative bacterial isolates from different samples were chosen and characterised in terms of their Gram reaction, cell size and morphology, growth at 15° C. and 45° C. and fermentation end-products from glucose. Greater than sixty percent of the isolates tested were Gram positive, homofermentative cocci arranged either in tetrads, chains or bunches. Eighteen percent of the isolates were Gram negative rods and heterofermentative coccobacilli.

The remaining isolates (twenty-two percent) were predominantly homofermentative coccobacilli. Thirty eight strains were characterised in more detail. All thirty eight isolates tested negative both for nitrate reduction and production of indole from tryptophan.

*Bifidobacterium longum* biotype infantis strain 35624 was chosen for full genome sequencing from this group of strains due to its proven anti-inflammatory activity in murine models of colitis (McCarthy et. al., 2004) and its immunomodulatory effects following oral consumption by Irritable Bowel Syndrome (IBS) patients (O'Mahony et al., 2005).

Example 2

Sequencing the Genome of *Bifidobacterium Longum* Infantis 35624

The *Bifidobacterium longum* biotype infantis strain 35624 genome sequence was determined using a whole shotgun approach. For this purpose two libraries were constructed: a small insert library (insert size ranging between 2 and 4 kb) employing pGEM-T easy vector (Promega) and a large insert (insert size ranging between 40 and 45 kb) cosmid library (Epicentre Technologies). Sequence sampling from these banks generated just over 26,828,618 base pairs of useable sequence data, which represented about 11.9-fold coverage of the *Bifidobacterium longum* biotype infantis strain 35624 genome (performed by MWG-Biotech, Ebersberg, Germany). Sequence reads were assembled using Phrap (Green) into 11 contigs. Gap closure and quality improvement of the initial sequence assembly was achieved by additional primer-directed sequencing using pre-identified clones from the libraries resulting in a single contig, which represented a circular chromosome of 2,264,374 by long. Based on the final consensus quality scores, we estimate an overall error rate of <1 per $4 \times 10^5$ bases

Example 3

Analysing the Genome of *Bifidobacterium Longum* Biotype Infantis 35624

Protein-encoding open reading frames (ORFs) were predicted using a combination of the methods Glimmer (Delcher et al., 1999b; Salzberg et al., 1998) and GeneBuilder (Internally developed software), as well as comparative analysis involving BLASTX (Altschul et al., 1997)

Results from the gene finder programs were manually combined, and preliminary identification of ORFs was made on the basis of BLASTP (Altschul et al., 1997) analysis against a non-redundant protein database provided by the National Centre for Biotechnology Information (Wheeler et al., 2005). Artemis (Rutherford et al., 2000), was used to inspect the identified ORFs and its associated BLASTP results. A manual inspection was performed in order to verify or, if necessary, redefine the start and stop of each predicted coding region. Annotation made use of the GC frame plot feature of Artemis, ribosome-binding site information obtained from RBSfinder (Suzek et al., 2001), alignments with similar ORFs from other organisms and G+C content analysis.

Example 4

Identifying Unique Genes in the Genome of Bifidobacterium Longum Infantis 35624

Assignment of protein function to predicted coding regions of the *Bifidobacterium longum* biotype infantis strain 35624 genome was performed using internally developed software and manual inspection. Primary functional classification of the *Bifidobacterium longum* biotype infantis strain 35624 gene products was performed according to the Riley rules (Riley, 1998a; Riley, 1993). The COG assignment was performed using XUGNITOR (Tatusov,). HMMER (Eddy,) was used to assign PFAM (Bateman et al., 2002) classification to the predicted proteins. TMHMM (Krogh et al., 2001) was used to predict transmembrane sequences, and SignalP (Bendtsen et al., 2004) was used for the prediction of signal peptides. Ribosomal RNA genes were detected on the basis of BLASTN searches and annotated manually. Transfer RNA genes were identified using tRNAscan-SE (Lowe and Eddy, 1997). Miscellaneous-coding RNAs were identified using the Rfam database (Griffiths-Jones et al., 2005) utilizing the INFERNAL software package (Eddy, 2002). Insertion sequence elements were identified using Repeatfinder (Volfovsky et al., 2001), Reputer (Kurtz & Schleiermcher, 1999) and BLAST (Altschul et al., 1990) and annotated manually. IS families were assigned using ISFinder. Carbohydrate-active enzymes were identified based on similarity to the carbohydrate-active enzyme (CAZy) database entries (Coutinho & Henrissat, 1999), and COG and PFAM classes annotated with carbohydrate enzyme activity. Transporter classification was performed according to the TC-DB scheme (Busch & Saier, 2002).

We identified a region from base numbers 44824 to 472245 (inclusive) of SEQ ID No. 1 that we designated exopolysaccharide (EPS) region 1 (SEQ ID No. 2). The EPS region 1 encodes the following genes:

TABLE 2

Open reading frames of EPS region 1 of the UCC 35624 genome

| Gene ID | Strand | Description | DNA sequence | Protein sequence |
| --- | --- | --- | --- | --- |
| BI00778 | + | glycosyl transferase CpsE | SEQ. ID No. 93 | SEQ. ID No. 133 |
| BI00779 | + | COG0840: Methyl-accepting chemotaxis protein | SEQ. ID No. 94 | SEQ. ID No. 134 |
| BI00780 | + | possible Etk-like tyrosine kinase involved in Eps biosynthesis | SEQ. ID No. 95 | SEQ. ID No. 135 |
| BI00781 | + | hypothetical glycosyl transferase, group 1 family protein | SEQ. ID No. 96 | SEQ. ID No. 136 |
| BI00782 | + | putative glycosyltransferase protein | SEQ. ID No. 97 | SEQ. ID No. 137 |
| BI00783 | + | NAD dependent epimerase/dehydratase family protein | SEQ. ID No. 98 | SEQ. ID No. 138 |
| BI00784 | + | UDP-glucose 6-dehydrogenase | SEQ. ID No. 99 | SEQ. ID No. 139 |
| BI00785 | + | hypothetical glycosyl transferase, group 1 family protein | SEQ. ID No. 100 | SEQ. ID No. 140 |
| BI00786 | + | hypothetical Eps11I | SEQ. ID No. 101 | SEQ. ID No. 141 |
| BI00787 | + | hypothetical Bacterial transferase hexapeptide (three repeats) | SEQ. ID No. 102 | SEQ. ID No. 142 |
| BI00788 | + | hypothetical Capsular polysaccharide synthesis protein | SEQ. ID No. 103 | SEQ. ID No. 143 |
| BI00789 | + | hypothetical protein | SEQ. ID No. 104 | SEQ. ID No. 144 |
| BI00790 | + | Eps9K | SEQ. ID No. 105 | SEQ. ID No. 145 |
| BI00791 | + | hypothetical Polysaccharide biosynthesis protein | SEQ. ID No. 106 | SEQ. ID No. 146 |
| BI00792 | + | hypothetical Bacterial transferase hexapeptide (three repeats) | SEQ. ID No. 107 | SEQ. ID No. 147 |
| BI00793 | − | NAD-dependent epimerase/dehydratase family protein, putative | SEQ. ID No. 108 | SEQ. ID No. 148 |
| BI00794 | − | transposase, degenerate | SEQ. ID No. 109 | SEQ. ID No. 149 |
| BI00795 | − | hypothetical COG2963: Transposase and inactivated derivatives | SEQ. ID No. 110 | SEQ. ID No. 150 |
| BI00796 | + | dTDP-glucose 4,6-dehydratase | SEQ. ID No. 111 | SEQ. ID No. 151 |
| BI00797 | + | dTDP-4-dehydrorhamnose 3,5-epimerase | SEQ. ID No. 112 | SEQ. ID No. 152 |
| BI00798 | + | glucose-1-phosphate thymidylyltransferase | SEQ. ID No. 113 | SEQ. ID No. 153 |

We also identified a region from base numbers 2071426 to 2097099 (inclusive) of SEQ ID No. 1 that we designated EPS region 2 (SEQ ID No. 3). The EPS region 2 encodes the following genes:

TABLE 3

Open reading frames of EPS region 2 of the UCC 35624 genome

| Gene ID | Strand | Description | DNA sequence | Protein sequence |
| --- | --- | --- | --- | --- |
| BI00319 | + | dTDP-glucose 4,6-dehydratase | SEQ. ID No. 114 | SEQ. ID No. 154 |
| BI00320 | + | conserved hypothetical protein | SEQ. ID No. 115 | SEQ. ID No. 155 |
| BI00321 | + | conserved hypothetical protein | SEQ. ID No. 116 | SEQ. ID No. 156 |
| BI00423t | + | conserved putative transposase | SEQ. ID No. 117 | SEQ. ID No. 157 |
| BI00322 | − | IS1533, OrfB | SEQ. ID No. 118 | SEQ. ID No. 158 |
| BI00323 | − | transposase (25) BH3998 [imported], putative | SEQ. ID No. 119 | SEQ. ID No. 159 |
| BI00324 | − | glycosyltransferase, putative | SEQ. ID No. 120 | SEQ. ID No. 160 |
| BI00325 | − | conserved sialic acid-specific 9-O-acetylesterase | SEQ. ID No. 121 | SEQ. ID No. 161 |
| BI00326 | + | hypothetical Acyltransferase family | SEQ. ID No. 122 | SEQ. ID No. 162 |
| BI00327 | − | conserved > hypothetical membrane protein with unknown function | SEQ. ID No. 123 | SEQ. ID No. 163 |
| BI00328 | − | hypothetical Glycosyl transferase family 8 | SEQ. ID No. 124 | SEQ. ID No. 164 |
| BI00329 | − | hypothetical glycosyl transferase, group 2 family protein | SEQ. ID No. 125 | SEQ. ID No. 165 |
| BI00330 | − | polysaccharide ABC transporter, ATP-binding protein | SEQ. ID No. 126 | SEQ. ID No. 166 |
| BI00331 | − | polysaccharide ABC transporter, permease protein, putative | SEQ. ID No. 127 | SEQ. ID No. 167 |
| BI00332 | + | hypothetical Glycosyl transferase family 8 | SEQ. ID No. 128 | SEQ. ID No. 168 |
| BI00333 | − | UDP-glucose 6-dehydrogenase | SEQ. ID No. 129 | SEQ. ID No. 169 |
| BI00334 | + | hypothetical NAD dependent epimerase/dehydratase family | SEQ. ID No. 130 | SEQ. ID No. 170 |
| BI00335 | − | membrane protein, putative | SEQ. ID No. 131 | SEQ. ID No. 171 |
| BI00336 | − | conserved hypothetical protein | SEQ. ID No. 132 | SEQ. ID No. 172 |

Example 5

Isolation and Screening of EPS-producing Bifidobacterial Strain from Fecal Samples Fecal Sample Preparation Fecal samples were collected by the subjects using a Kendall precision commode specimen collection system. The collected samples were stored chilled in a cold pack prior to sample processing. Only samples that are less than twenty four hours old were used in the evaluations.

A 10.0 gm sample of mixed fecal material was placed into a plastic stomaching bag containing 90 ml of saline. The suspension was stomached for 2 minutes. The suspension was filtered through a gauze pad contained within a disposable funnel. Following the filtration, 45 ml of the filtered fecal homogenate was transferred to a 50 ml disposable centrifuge tube. This fecal suspension was further used for DNA extraction or for bacterial isolation.

Screening Fecal Samples Using Three TaqMan Real-Time PCR Assays.

Fecal Sample DNA Preparation. A 2.0 ml aliquot of the fecal homogenate was pelleted using a microcentrifuge. The pellets were resuspended in 20 mg/ml lysozyme, for 2 hours at 37° C. DNA was extracted using a QIAamp DNA Stool Mini Kit (Qiagen). The DNA concentration was measured by Pico Green assay (Molecular Probes). Once the DNA concentration was measured, the DNA was stored at 4° C.

TaqMan Real-Time PCR Reactions. The test samples were diluted to a concentration of DNA of 2 ng/ul so that 5 µl contained a total of 10 ng DNA. Samples were assayed by a total of three separate assays.

The following reaction mix was made:

| | |
| --- | --- |
| Water | 15.75 µl |
| 10 µM forward primer | 1.5 µl (300 nM final concentration) |
| 10 µM reverse primer | 1.5 µl (300 nM final concentration) |
| 10 µM TaqMan probe | 1 µl (200 nM final concentration) |
| BSA (20 mg/ml) | 0.25 µl (0.1 ug/ml final concentration) |
| TaqMan Universal Master Mix | 25 µl |

A bulk mix was made for the number of samples to be assayed. A 45 µl aliquot was dispensed into each well of a 96 well microtitre plate, then 5 µl DNA was added to each well. The plate was spun briefly, and placed into the thermocycler (ABI 7900 HT). The standard TaqMan thermocycling protocol was used.

TanMan RT-PCR Program. The standard TaqMan quantitative PCR thermocycling protocol is as follows:

Step 1: 95° C. for 10 minutes (to activate the AmpliTaq Gold polymerase)

Step 2: 95° C. for 15 seconds (the denaturation step)

Step 3: 60° C. for 60 seconds (the priming/polymerization step)

Steps 2 and 3 are repeated 40 times. Fluorescent data is collected at step 3.

Primers and Probes for Three TaqMan RT-PCR assays. The fecal sample DNAs were screened using a EPS gene-specific assay and two B. infantis 35624 Unknown gene-specific assays (Unknown genes UNK1 and UNK2). The specific genes used and their TaqMan primer sets are shown in Table 4 below.

TABLE 4

UCC 35624 Primer set for TaqMan PCR

| Target Gene | Name | Sequence 5'-3' | Genome start | Genome end | TaqMan Probe label |
|---|---|---|---|---|---|
| BI01615 (UNK-1) | UNK1-F1 | CCATGAGCGGTTTCACGAA (SEQ ID No. 4) | 1451446 | 1451428 | 5' 6-FAM 3' |
| | UNK1-R1 | TTGGACGGTGCCTGTGATTA (SEQ ID No. 5) | 1451393 | 1451412 | NFQ-MG |
| | UNK1-MGB1 | CGGGCAATCAAC (SEQ ID No. 6) | 1451426 | 1451415 | |
| BI02420t (UNK-2) | UNK2-F1 | ACTTGACGTACCGTTTTGAGATTTC (SEQ ID No. 7) | 1656479 | 1656503 | 5' 6-FAM 3' |
| | UNK2-R1 | CTAAGCATGGCAAGGCTGATAGT (SEQ ID No. 8) | 1656562 | 1656540 | NFQ-MGB |
| | UNK2-MGB1 | TGCGACCAACACGC (SEQ ID No. 9) | 1656525 | 1656538 | |
| BI00783 (EPS) | EPS-F1 | GGGTCCAATAAGAAGGTTCCATATT (SEQ ID No. 10) | 456491 | 456515 | 5' 6-FAM 3' |
| | EPS-R1 | GCATGTGCCAACAGCTCATC (SEQ ID NO. 11) | 456591 | 456572 | TAMR |
| | EPS-TAMRA | CGGATGACAAGGTAGATAATCCAGTGAGCCTATAC (SEQ ID No. 12) | 456519 | 456553 | |

The fecal samples which showed high DNA concentration by the *B. infantis* 35624 EPS gene-specific assay, but negative reactions by using *B. infantis* 35624 Unknown gene-specific assays, were further used for the isolation of potential EPS-producing bacteria.

Example 6

Isolation and Characterization of BL1207 from Fecal Samples

One milliliter of bacterial suspension (see Example 5 above) was transferred to 9.0 ml of sterile phosphate-buffered saline which constituted the $10^{-1}$ dilution. One milliliter of this $10^{-1}$ dilution was transferred to 9.0 ml of sterile phosphate-buffered saline which was the $10^{-2}$ dilution. This process was continued until the $10^{-10}$ dilution was prepared. Then, 0.1 ml of each dilution was plated onto the surfaces of Reinforced Clostridial Agar (RCA) plates (BD or equivalent) and *Lactobacillus* Man-Rogosa Sharpe agar (MRSA) plates (BD or equivalent). The plates were incubated under anaerobic condition (COY anaerobic Chamber) at 33° C.±2° C. for 48-72 hours.

Following incubation, single colonies (a total of approximately 100 colonies) were picked from RCA and MRSA plates and further streaked on new plates for isolate purification. The plates with the streaked colonies were incubated under anaerobic conditions (COY anaerobic Chamber) at 33° C.±2° C. for 48 to 72 hours. After incubation, the pure colonies observed on plates were then submitted for DNA extraction.

Screening Fecal Isolates Using Three TaqMan Real-Time PCR Assays

The bacterial DNA was extracted using the Preman™ Ultra Sample Preparation Reagent and Protocol (Applied Biosystems). The DNA was further analyzed using three TaqMan RT-PCR assays (EPS gene-specific assay [EPS-1] and two *B. infantis* 35624 Unknown gene-specific assays [UNK1 and UNK2] as described above in Example 5. Only one isolate showed *B. infantis* 35624 EPS gene-specific assay positive, but *B. infantis* 35624 Unknown gene-specific assays-negative. This isolate was further identified using 16S rDNA sequencing.

Identification of Potential EPS-producing Strain by 16S rDNA Sequencing.

The 16S rRNA gene fragment was amplified and sequenced using ABI Full Gene PCR kit (Applied Biosystems, Foster City, Calif.).

(1). 16S rRNA Gene Amplification:

PCR amplification was carried out on a GeneAmp PCR System 9700 thermal cycler with the following program:

| Initial Hold: | 95° C. for 10 minutes |
|---|---|
| 30Cycles: | 95° C. for 30 seconds (Denaturing) |
| | 60° C. for 30 seconds (Annealing) |
| | 72° C. for 45 seconds (Extension) |
| Final Extension: | 72° C. for 10 minutes |

(2). 16S rRNA Gene Sequencing:

Sequencing was further performed on the thermal cycler using the following program:

| 25 Cycles: | 96° C. for 10 seconds (Denaturing) |
|---|---|
| | 50° C. for 5 seconds (Annealing) |
| | 60° C. for 4 minutes (Extension) |
| Final step | Hold at 4° C. |

The sequencing PCR product was further purified using DyeEX™ 2.0 spin kit and sequenced using 3130 x1 Genetic Analyzer (Applied Biosystems, Foster City, Calif.).

(3) Sequence Data Analysis:

Comparison of the consensus sequences with GenBank sequences was done by using Basic Local Alignment Search Tool (BLAST). The GenBank search indicated that the *B infantis* 35624 EPS gene-specific positive, but *B. infantis* 35624 Unknown gene-specific negative strain is *Bifidobacterium longum*. This strain is designated BL1207.

Example 7

Isolation and Screening of EPS-Expressing *Bifidobacterial Longum* Strains

Isolation of Bacterial Strains

Bacteria were isolated from bowel tissue and/or fecal samples using the methodology described in Example 1 above. In particular, *Bifidobacterium longum* strain AH121a was isolated from feline bowel tissue and *Bifidobacterium longum* strain AH1714 was isolated from colonic biopsy tissue from healthy human subjects.

EPS Gene Cluster Screen

Bacterial strains were screened for the presence of genes from EPS cluster 1 (Table 2 above) and EPS cluster 2 (Table 3 above) using the primers listed in Tables 5 and 6 below. Briefly, the following methodology was used for the PCR EPS cluster gene screen:

10 ml Modified Rogosa broth media (+0.05% cysteine) was inoculated aseptically with a freshly grown colony of the bacterial strain and incubated anaerobically at 37° C. until turbid (about 16 to about 24 hours). The broth cultures were centrifuged and DNA was isolated from the resultant pellet using a Sigma™ extraction procedure. A nanodrop was used to ascertain the concentration of DNA in the sample and samples were diluted using DEPC water to a final concentration of 50 ng/ul DNA per sample. The template DNA samples were used in individual PCR reactions with the primer sets listed in Tables 5 and 6 below under the following conditions:

| Step | Temp (° C.) | Time (sec) | |
|---|---|---|---|
| 1 | 95 | 240 | |
| 2 | 95 | 45 | |
| 3 | 60 | 45 | |
| 4 | 72 | 45 | repeat steps 2 to 4, 25 times |
| 5 | 4 | hold | |

The primers were specifically designed to amplify a PCR product of approximately 500 base pair for the 40 genes of EPS clusters 1 and 2. PCR products were visualised following agarose gel electrophoresis with an appropriate DNA ladder for reference sizing. The presence (YES) or absence (NO) of a 500 bp PCR product is indicated in Tables 7 and 8 below.

TABLE 5

Primers for screening bacterial strains for the presence of genes from EPS cluster 1

| Gene ID | Primer name | LRFR | Sequence | SEQ ID NO. |
|---|---|---|---|---|
| BI00778 | 1.01 | L | tat gtt gcc ggc att tat ca | SEQ ID No. 13 |
| BI00778 | 1.01 | R | tgc gcg ttc atg tca ata at | SEQ ID No. 14 |
| BI00779 | 1.02 | L | ggc gta gca agt tca agg ag | SEQ ID No. 15 |
| BI00779 | 1.02 | R | aat aac cgc tgc agg aac ac | SEQ ID No. 16 |
| BI00780 | 1.03 | L | gtg cag gac ggt aat gga gt | SEQ ID No. 17 |
| BI00780 | 1.03 | R | gct tcg ggt ctg gat cat ta | SEQ ID No. 18 |
| BI00781 | 1.04 | L | tgc tga caa gtg gag tct gg | SEQ ID No. 19 |
| BI00781 | 1.04 | R | cca cgt cta cga gca act ca | SEQ ID No. 20 |
| BI00782 | 1.05 | L | gaa agc gaa gag tgg tct gg | SEQ ID No. 21 |
| BI00782 | 1.05 | R | ccg gct gat ttg atg aga tt | SEQ ID No. 22 |
| BI00783 | 1.06 | L | tgc cgc tgt act ggt cac | SEQ ID No. 23 |
| BI00783 | 1.06 | R | gca tgt gcc aac agc tca | SEQ ID No. 24 |
| BI00784 | 1.07 | L | cca aca cgt atc tgg cac tg | SEQ ID No. 25 |
| BI00784 | 1.07 | R | tcg gag cca aag aag gta ga | SEQ ID No. 26 |
| BI00785 | 1.08 | L | ata ccg cgt atg ctt tgg ac | SEQ ID No. 27 |
| BI00785 | 1.08 | R | aaa cgg taa cca ctc gct tg | SEQ ID No. 28 |
| BI00786 | 1.09 | L | atg gga tcg atg cat gaa at | SEQ ID No. 29 |
| BI00786 | 1.09 | R | ttc tcg gca ata aac cgt tc | SEQ ID No. 30 |
| BI00787 | 1.10 | L | cca gcg gtt att tcg ttg tt | SEQ ID No. 31 |
| BI00787 | 1.10 | R | ggt ggc atg atc ctt atg ct | SEQ ID No. 32 |
| BI00788 | 1.11 | L | gct atc ttc acc gca ttg gt | SEQ ID No. 33 |
| BI00788 | 1.11 | R | cca gtc agg gaa ggt cac at | SEQ ID No. 34 |

TABLE 5-continued

Primers for screening bacterial strains for the presence of genes from EPS cluster 1

| Gene ID | Primer name | LRFR | Sequence | SEQ ID NO. |
|---|---|---|---|---|
| BI00789 | 1.12 | L | tga aat aca cgc aac ccg ta | SEQ ID No. 35 |
| BI00789 | 1.12 | R | aatgcgtcaaaaccgatacc | SEQ ID No. 36 |
| BI00790 | 1.13 | L | gga aag caa tga gga agc tg | SEQ ID No. 37 |
| BI00790 | 1.13 | R | gat ttg atg caa agc aag ca | SEQ ID No. 38 |
| BI00791 | 1.14 | L | gtg agt acc gtt tcc gca at | SEQ ID No. 39 |
| BI00791 | 1.14 | R | ttc ctt ggt tcc cgt gat ag | SEQ ID No. 40 |
| BI00792 | 1.15 | L | gct ggg att ttg gaa gtg aa | SEQ ID No. 41 |
| BI00792 | 1.15 | R | tgt tac ccc cgg cat aat aa | SEQ ID No. 42 |
| BI00793 | 1.16 | L | acc ggt aac gtt cag att gc | SEQ ID No. 43 |
| BI00793 | 1.16 | R | gca ata ccg cct tga cct ta | SEQ ID No. 44 |
| BI00794 | 1.17 | L | ttg tac cac cac acg tac cg | SEQ ID No. 45 |
| BI00794 | 1.17 | R | cgc gag ttc aat ggc tat g | SEQ ID No. 46 |
| BI00795 | 1.18 | L | aca tcg acc tcc atc tcc ag | SEQ ID No. 47 |
| BI00795 | 1.18 | R | ata cgt aac agc ggc tcc ac | SEQ ID No. 48 |
| BI00796 | 1.19 | L | aag tac gat gtg cgc tac ca | SEQ ID No. 49 |
| BI00796 | 1.19 | R | cat cac ggt cag gat gtc ac | SEQ ID No. 50 |
| BI00797 | 1.20 | L | cga ata cac gga cat caa cg | SEQ ID No. 51 |
| BI00797 | 1.20 | R | gag aat cga gca gct gga ac | SEQ ID No. 52 |
| BI00798 | 1.21 | L | tgg gag agg agt tca tcg ac | SEQ ID No. 53 |
| BI00798 | 1.21 | R | gta tcc agc cat gcg taa cc | SEQ ID No. 54 |

TABLE 6

Primers for screening bacterial strains for the presence of genes from EPS cluster 2

| Gene ID | Primer name | LRFR | Sequence | SEQ ID NO. |
|---|---|---|---|---|
| BI00319 | 2.01 | L | acg gac tca aaa cca cca tc | SEQ ID No. 55 |
| BI00319 | 2.01 | R | acc ctg ctt ccg gta ctt tt | SEQ ID No. 56 |
| BI00320 | 2.02 | L | gcc tac gca aga cct tat gc | SEQ ID No. 57 |
| BI00320 | 2.02 | R | cgt tat acg cgt gct tga ga | SEQ ID No. 58 |
| BI00321 | 2.03 | L | tgg aac gca ata ttc aac ga | SEQ ID No. 59 |
| BI00321 | 2.03 | R | cca agt atg gct cca cga at | SEQ ID No. 60 |
| BI00423t | 2.04 | L | acg cct gtc tat ggt tgg aa | SEQ ID No. 61 |
| BI00423t | 2.04 | R | cgg tag gac tcg ttc tcg tc | SEQ ID No. 62 |
| BI00322 | 2.05 | L | tcg agg ttc gag gtg aag at | SEQ ID No. 63 |
| BI00322 | 2.05 | R | cct gtt cga gaa gga gaa cg | SEQ ID No. 64 |

TABLE 6-continued

Primers for screening bacterial strains for the presence of genes from EPS cluster 2

| Gene ID | Primer name | LRFR | Sequence | SEQ ID NO. |
|---|---|---|---|---|
| BI00323 | 2.06 | L | atg gaa gca tgt ggt cct tc | SEQ ID No. 65 |
| BI00323 | 2.06 | R | att tcc tgg tgg tgt cgt tc | SEQ ID No. 66 |
| BI00324 | 2.07 | L | atg gcg aaa ctg ttg gac tc | SEQ ID No. 67 |
| BI00324 | 2.07 | R | gct acc gtg cct tct cat tc | SEQ ID No. 68 |
| BI00325 | 2.08 | L | gcc gaa tcg ctt ttg aaa ta | SEQ ID No. 69 |
| BI00325 | 2.08 | R | aaa tcc tca tcg ggg aaa ac | SEQ ID No. 70 |
| BI00326 | 2.09 | L | gtt tat ttt cgc cgt gcc ta | SEQ ID No. 71 |
| BI00326 | 2.09 | R | aat tcc aat ggc ttt tgc tg | SEQ ID No. 72 |
| BI00327 | 2.10 | L | atg tgc gaa tcc gac ata ca | SEQ ID No. 73 |
| BI00327 | 2.10 | R | tgc tta tct cgt ccc cat tc | SEQ ID No. 74 |
| BI00328 | 2.11 | L | gca aaa tgc ttg gct tct tc | SEQ ID No. 75 |
| BI00328 | 2.11 | R | ctg gat tcc gat gat gct tt | SEQ ID No. 76 |
| BI00329 | 2.12 | L | ctg cac gta tcg gga ttt tt | SEQ ID No. 77 |
| BI00329 | 2.12 | R | ctc ggc aga gga cag gat ag | SEQ ID No. 78 |
| BI00330 | 2.13 | L | gat cat cga cac gca atg ac | SEQ ID No. 79 |
| BI00330 | 2.13 | R | taa ggc cat cct cat caa gg | SEQ ID No. 80 |
| BI00331 | 2.14 | L | tct ggg gaa agc agg tta tg | SEQ ID No. 81 |
| BI00331 | 2.14 | R | ctg tgc ggt acc tgt ttg tg | SEQ ID No. 82 |
| BI00332 | 2.15 | L | aat tac gtc ccg atg ctc ac | SEQ ID No. 83 |
| BI00332 | 2.15 | R | caa tac acc ggc ttg gaa gt | SEQ ID No. 84 |
| BI00333 | 2.16 | L | tgt aga cct tgt cgc tca cg | SEQ ID No. 85 |
| BI00333 | 2.16 | R | gca tcg gtg acg gct ata at | SEQ ID No. 86 |
| BI00334 | 2.17 | L | gtg ctc gac aag ctg acg ta | SEQ ID No. 87 |
| BI00334 | 2.17 | R | gtg ttc cgc ata cca atc g | SEQ ID No. 88 |
| BI00335 | 2.18 | L | ggc gag tgc acc aaa taa at | SEQ ID No. 89 |
| BI00335 | 2.18 | R | cga ttc cgt cta ttg gtt cg | SEQ ID No. 90 |
| BI00336 | 2.19 | L | ata agt ccg gtg gca atc ag | SEQ ID No. 91 |
| BI00336 | 2.19 | R | caa tgg atg ata cgg tgc tg | SEQ ID No. 92 |

TABLE 7

Results of EPS cluster 1 gene screen

| Gene ID | Primer set | B. longum 35624 | B. longum 1207 | B. longum AH121A | B. longum 1714 |
|---|---|---|---|---|---|
| BI00778 | 1.01 | YES | YES | NO | YES |
| BI00779 | 1.02 | YES | YES | NO | YES |
| BI00780 | 1.03 | YES | YES | NO | YES |
| BI00781 | 1.04 | YES | YES | YES | YES |
| BI00782 | 1.05 | YES | YES | YES | YES |
| BI00783 | 1.06 | YES | YES | YES | YES |
| BI00784 | 1.07 | YES | YES | YES | YES |
| BI00785 | 1.08 | YES | YES | YES | YES |
| BI00786 | 1.09 | YES | YES | YES | YES |
| BI00787 | 1.10 | YES | YES | YES | YES |
| BI00788 | 1.11 | YES | YES | YES | NO |
| BI00789 | 1.12 | YES | YES | YES | YES |
| BI00790 | 1.13 | YES | YES | YES | YES |
| BI00791 | 1.14 | YES | YES | YES | YES |

TABLE 7-continued

Results of EPS cluster 1 gene screen

| Gene ID | Primer set | B. longum 35624 | B. longum 1207 | B. longum AH121A | B. longum 1714 |
|---|---|---|---|---|---|
| BI00792 | 1.15 | YES | YES | YES | YES |
| BI00793 | 1.16 | YES | YES | NO | YES |
| BI00794 | 1.17 | YES | YES | NO | YES |
| BI00795 | 1.18 | YES | YES | NO | YES |
| BI00796 | 1.19 | YES | YES | YES | YES |
| BI00797 | 1.20 | YES | NO | NO | NO |
| BI00798 | 1.21 | YES | YES | YES | YES |

In which YES indicates the presence and NO indiates the absence of a 500 bp PCR product.

TABLE 8

Results of EPS cluster 1 gene screen

| Gene ID | Primer set | B. longum 35624 | B. longum 1207 | B. longum AH121A | B. longum 1714 |
|---|---|---|---|---|---|
| BI00319 | 2.01 | YES | NO | NO | NO |
| BI00320 | 2.02 | YES | NO | NO | NO |
| BI00321 | 2.03 | YES | NO | NO | NO |
| BI00423t | 2.04 | YES | NO | NO | NO |
| BI00322 | 2.05 | YES | NO | NO | NO |
| BI00323 | 2.06 | YES | NO | NO | NO |
| BI00324 | 2.07 | YES | NO | NO | NO |
| BI00325 | 2.08 | YES | NO | NO | NO |
| BI00326 | 2.09 | YES | NO | NO | NO |
| BI00327 | 2.10 | YES | NO | NO | NO |
| BI00328 | 2.11 | YES | NO | NO | NO |
| BI00329 | 2.12 | YES | NO | NO | NO |
| BI00330 | 2.13 | YES | NO | NO | NO |
| BI00331 | 2.14 | YES | NO | NO | NO |
| BI00332 | 2.15 | YES | NO | NO | NO |
| BI00333 | 2.16 | YES | NO | NO | NO |
| BI00334 | 2.17 | YES | NO | NO | NO |
| BI00335 | 2.18 | YES | YES | NO | YES |
| BI00336 | 2.19 | YES | YES | YES | YES |

In which YES indicates the presence and NO indiates the absence of a 500 bp PCR product.

Congo Red Agar Screen

A Congo red agar screen was used to phenotypically screen for EPS expressing bacterial strains. Briefly, 10 ml Modified Rogosa broth media (+0.05% cysteine) was inoculated aseptically with a freshly grown colony of the bacterial strain and incubated anaerobically at 37° C. until turbid (about 16 to about 24 hours). The broth cultures were aseptically streaked onto Congo Red Agar plates and incubated anaerobically at 37° C. for 48 hours. It is believed that EPS produced as a by-product of the growth and/or metabolism of certain strains prevents the uptake of the Congo red stain resulting in a cream/white colony morphology. Stains that produce less EPS take up the Congo red stain easily, resulting in a pink/red colony morphology. Strains that do not produce an EPS stain red and look almost transparent in the red agar background.
Referring to FIGS. 6 to 12, the following colony morphologies were observed:

TABLE 9

Colony morphologies from Congo red agar screen

| Bacterial Strain | Colony morphology |
|---|---|
| B. longum 35624 (FIG. 6) | Convex, mucoid, bright white colonies |
| B. longum AH121A (FIG. 7) | Convex, mucoid, bright white colonies |
| B. logum AH1714 (FIG. 8) | Convex, mucoid, bright white colonies |
| B. longum AH0119 (FIG. 9) | Convex, mucoid, pale pink/off white colonies |
| B. breve UCC2003 (FIG. 10) | Convex, mucoid, pale pink/off white colonies |
| L. rhamnosus AH308 (FIG. 11) | Flat, semi-mucoid, pale pink/off white colonies |
| L. salivarius UCC1 (FIG. 12) | Flat, non-mucoid, clear/transparent colonies |

Example 8

*B. infantis* 35624 and BL1207 Induce Nearly Identical Cytokine Profiles in PBMCs Peripheral blood mononuclear cells (PBMCs) were isolated from fresh human peripheral blood using BD Vacutainer CPT tubes (BD catalog 362761), as per the manufacturer's instructions. PBMCs were washed and resuspended in Dulbecco's MEM (Gibco catalog 10569-010) plus 25 mM HEPES, 10% fetal bovine serum (Sigma catalog F4135), and 1% penicillin/streptomycin (Sigma catalog P0781). $2 \times 10^5$ PBMCs (in 200 µl of DMEM) were plated into each well of a 96-well culture plate.

Bacteria were grown in Difco MRS media and harvested just after entering into stationary phase. All cells were grown under anaerobic conditions at 37° C. Growth curves (OD vs # of live cells) were constructed for each growth condition, and washed cells were normalized by cell number before addition to the PBMCs.

Bacteria (20 µl in phosphate buffered saline (PBS)) were added to each well of PBMCs to give the total number of bacteria as indicated for each experiment. Three different amounts of bacteria were tested: 1.25E+07, 6.25E+06, and 3.13E+06 were added to separate wells of PBMCs. A no-bacteria control also was run. All assays were done in triplicate. After a 2-day incubation at 37° C., the plates were spun at 300×g, and the supernatants were removed and stored frozen at −80° C. until analysis.

Cytokines in the culture supernatants were assayed using a 96-well assay kit from Meso Scale Discovery (Gaithersburg, Md.; catalog K15008B-1). Human Interleukin-1 beta (Il-1b), Interleukin 10 (Il-10), Interleukin 12p70 (Il112p70), and Tumor Necrosis Factor alpha (TNFa) 25 were quantitated and reported as picograms per milliliter. Each sample was assayed in duplicate.

FIGS. 2 to 5 show the results of a representative experiment. For each cytokine shown, *B. infantis* 35624 and BL1207 induce nearly identical levels of cytokines. These levels are very different than the levels induced by the three other Bifidobacterial strains that they were compared to.

Example 9

*Bifidobacteria* with Similar EPS Genes and High EPS Production Induce a Significantly Elevated IL-10:IL-12 Ratio Compared to Strains Lacking These Genes Peripheral blood mononuclear cells (PBMCs) were isolated from healthy human peripheral blood using BD Vacutainer CPT tubes (BD catalog 362761), as per the manufacturer's instructions. PBMCs were washed and resuspended in Dulbecco's Modified Eagle Medium-Glutamax™ (Glutamax (Glutamine substitute)+pyruvate+4.5 g/l glucose (Gibco catalog 10569-010) 10% fetal bovine serum (Sigma catalog F4135), and 1% penicillin/streptomycin (Sigma catalog P0781). PBMCs were incubated ($2\times10^5$ cells per well) in flat-bottomed 96-well plates and 20 µL of a bacterial suspension (at a concentration of $1\times10^7$ CFU/mL) was added. PBMCs were co-incubated with bacteria for 48 hours at 37° C./5% $CO_2$ in an incubator. After the 2 day incubation period, the plates were centrifuged at 300×g, and the supernatants were removed and stored frozen at −80° C. until analysis. Interleukin-10 (IL-10) and Interleukin-12p70 (IL-12p70) levels in the culture supernatants were quantified using a 96-well assay kit from Meso Scale Discovery (Gaithersburg, Md.; catalog K15008B-1)

Bacteria were prepared for co-culture experiments in two formats. (a) Freshly grown bacteria were grown in Difco MRS media and harvested just after entering into stationary phase. All cells were grown under anaerobic conditions at 37° C. (b) Bacteria were grown under anaerobic conditions at 37° C. in Difco MRS media and harvested just after entering into stationary phase. Freeze dried powders were generated for each of these bacteria and stored at −80° C. in pre-aliquoted 100 mg vials Immediately prior to their use, one aliquot of each strain was removed from the freezer and allowed to reach room temperature. Each strain was washed 3 times in 10 ml ringers followed by centrifugation. A fresh vial was used on each occasion. Growth curves (OD vs number of live cells) were constructed for each growth condition, and washed cells were normalized by cell number before addition to the PBMCs. A no-bacteria control was also included in all experiments. All assays were done in triplicate.

Figure 13:
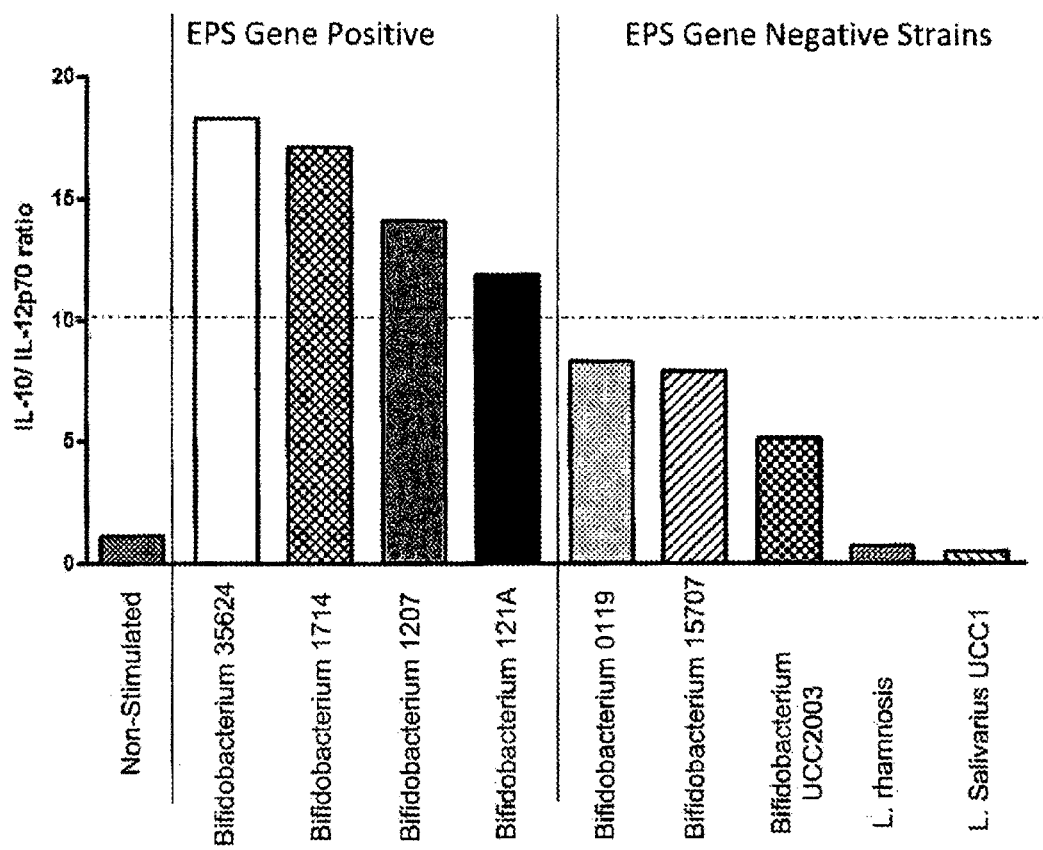
FIG. 13 is a bar chart illustrating the IL-10:IL-12p70 ratio for PBMCs stimulated with *Bifidobacterium longum* infantis strain 35624 (*Bifidobacterium* 35624), *Bifidobacterium longum* strain 1714 (*Bifidobacterium* 1714), *Bifidobacterium longum* strain 1207 (*Bifidobacterium* 1207), *Bifidobacterium longum* strain 121A (*Bifidobacterium* 121A), *Bifidobacterium longum* strain 0119 (*Bifidobacterium* 0119), *Bifidobacterium longum* strain 15707 (*Bifidobacterium* 15707), *Bifidobacterium breve* strain 8807 (*Bifidobacterium* UCC2003), *Lactobacillus rhamnosus* and *Lactobacillus salivarius* strain UCC1.

The *Bifidobacteria* which contained many of the EPS genes exhibited a similar effect on IL-10:IL-12 induction while bacterial strains which do not contain the EPS genes induced a significantly lower IL-10:IL-12 ratio (FIG. 13). Both freshly grown and freeze-dried cultures exhibited a similar effect in that the strains containing similar EPS genes induced a higher IL-10:IL-12 ratio than those strains that did not contain these genes.

The control of inflammatory diseases is exerted at a number of levels. The controlling factors include hormones, prostaglandins, reactive oxygen and nitrogen intermediates, leukotrienes and cytokines. Cytokines are low molecular weight biologically active proteins that are involved in the generation and control of immunological and inflammatory responses. A number of cell types produce these cytokines, with neutrophils, monocytes and lymphocytes being the major sources during inflammatory reactions due to their large numbers at the injured site.

Multiple mechanisms exist by which cytokines generated at inflammatory sites influence the inflammatory response. Chemotaxis stimulates homing of inflammatory cells to the injured site, whilst certain cytokines promote infiltration of cells into tissue. Cytokines released within the injured tissue result in activation of the inflammatory infiltrate. Most cytokines are pleiotropic and express multiple biologically overlapping activities. As uncontrolled inflammatory responses can result in diseases such as IBD, it is reasonable to expect that cytokine production has gone astray in individuals affected with these diseases.

Interleukin-10 (IL-10) is an anti-inflammatory cytokine which is produced by many cell types including monocytes, macrophages, dendritic cells, mast cells and lymphocytes (in particular T regulatory cells). IL-10 down-regulates the expression of pro-inflammatory Th1 cytokines, MHC class II antigens, and co-stimulatory molecules on antigen presenting cells. It also enhances B cell survival, proliferation, and antibody production. This cytokine can block NF-κB activity, and is involved in the regulation of the JAK-STAT signaling pathway. Murine knock-out studies have demonstrated the essential role for IL-10 in immunoregulation as IL-10KO mice develop severe colitis. In addition, bacteria which are potent inducers of IL-10 have been shown to promote T regulatory cell differentiation in vivo thus contributing to immunological homeostasis (O'Mahony et al., AJP 2006; O'Mahony et al., PLoS Pathogens 2008).

Interleukin-12 (IL-12) is a pro-inflammatory cytokine associated with polarisation of Th1 effector T cell responses and stimulates the production of other pro-inflammatory Th1 cytokines, such as interferon-gamma (IFN-γ) and tumor necrosis factor-alpha (TNF-α), from T and natural killer (NK) cells. High levels of IL-12 expression is associated with autoimmunity. Administration of IL-12 to people suffering from autoimmune diseases was shown to worsen disease symptoms. In contrast, IL-12 knock-out mice or treatment of mice with IL-12 neutralising antibodies ameliorated the disease.

Cytokine cascades and networks control the inflammatory response, rather than the action of a particular cytokine on a particular cell type. The relative levels of expression, or balance, of two cytokines (such as IL-10 and IL-12) is more informative than the expression of a single cytokine. In these studies, we stimulated human PBMCs with a range of different bacterial strains. All strains induced IL-10 and all strains induced IL-12. However, examination of the ratio between IL-10 and IL-12 induction revealed that some bacterial strains induced a higher ratio (i.e. more IL-10 with less IL-12) compared to other strains. This is a meaningful observation as it is the balance between each of these opposing signals that ultimately determines the immunological outcome. It is anticipated that a high IL-10:IL-12 ratio would promote an anti-inflammatory response associated with appropriate immunoregulatory activity while a low IL-10:IL-12 ratio would contribute to Th1 polarisation of the immune response. Thus, the PBMC IL-10:IL-12 ratio is a important selection criterion for identification of bacterial strains with immunoregulatory properties.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

REFERENCES

Altschul, S. F., Madden, T. L., Schaffer, A. A., Zhang, J., Zhang, Z., Miller, W., and Lipman, D. J. (1997). Gapped BLAST and PSI-BLAST: a new generation of protein database search programs. Nucleic Acids Res 25, 3389-3402.
Altschul S. F., Gish W., Miller W., Myers E. W. and Lipman D. J. (1990) Basic local alignment search tool. J Mol Biol. 215: 403-410.
Bateman, A., Birney, E., Cerruti, L., Durbin, R., Etwiller, L., Eddy, S. R., Griffiths-Jones, S., Howe, K. L., Marshall, M., and Sonnhammer, E. L. (2002). The Pfam protein families database. Nucleic Acids Res 30, 276-280.
Bendtsen J. D., Nielsen H., von Heijne G. and Brunak S. (2004) Improved prediction of signal peptides: SignalP 3.0. J Mol Biol. 340: 783-795.
Bouhnik Y Survival And Effects Of Bacteria Ingested In Fermented Milk In Man Lait 73 (2): 241-247 1993
Busch W, Saier M H The Transporter Classification (TC) system, 2002 Critical Reviews In Biochemistry And Molecular Biology 37 (5): 287-337 2002
Chevalier, P. et al. (1990) *J. Appl. Bacteriol* 68, 619-624)
Coutinho & Henrissat, 1999
Delcher A L, Harmon D, Kasif S, White O, Salzberg S L Improved microbial gene identification with GLIMMER Nucleic Acids Research 27 (23): 4636-4641 Dec. 1, 1999
Eddy, S. R. The HMMER software tools.
Eddy S R A memory-efficient dynamic programming algorithm for optimal alignment of a sequence to an RNA secondary structure BMC BIOINFORMATICS 3: Art. Nov. 18, 2002
Green, P. The Phred/Phrap/Consed system home page
Griffiths-Jones S, Moxon S, Marshall M, Khanna A, Eddy S R, Bateman A Rfam: annotating non-coding RNAs in complete genomes Nucleic Acids Research 33: D121-D124 Sp. Iss. SI Jan. 1, 2005
Krogh A, Larsson B, von Heijne G, Sonnhammer E L L., Predicting transmembrane protein topology with a hidden Markov model: Application to complete genomes Journal Of Molecular Biology 305 (3): 567-580 Jan. 19, 2001
Kurtz S, Schleiermacher C REPuter: fast computation of maximal repeats in complete genomes Bioinformatics 15 (5): 426-427 May 1999
Lowe T M, Eddy S R tRNAscan-SE: A program for improved detection of transfer RNA genes in genomic sequence Nucleic Acids Research 25 (5): 955-964 Mar. 1, 1997
Liu M, van Enckevort F H, Siezen R J, Genome update: lactic acid bacteria genome sequencing is booming Microbiology 2005, vol 151 pp 3811-3814
McCarthy et al., 2004
O'Mahony L, McCarthy J, Kelly P, Hurley G, Luo F, Chen K, O'Sullivan G C, Kiely B, Collins J K, Shanahan F, Quigley E M.: *Lactobacillus* and *bifidobacterium* in irritable bowel syndrome: symptom responses and relationship to cytokine profiles.
Gastroenterology. March 2005; 128(3):541-51.
O'Mahony et al., A J P 2006
O'Mahony et al., PLoS Pathogens 2008
Riley, 1993
Riley, 1998a
Rutherford, K., Parkhill, J, Crook, J., Horsnell, T., Rice, P., Rajandream, M. A., and Barrell, B. (2000). Artemis: sequence visualization and annotation. Bioinformatics 16, 944-945.
Salzberg S, Delcher A L, Fasman K H, Henderson J. A decision tree system for finding genes in DNA Journal Of Computational Biology 5 (4): 667-680 WIN 1998
Suzek, B. E., Ermolaeva, M. D., Schreiber, M., and Salzberg, S. L. (2001). A probabilistic method for identifying start codons in bacterial genomes. Bioinformatics 17, 1123-1130.
Tatusov, R. L., The XUGNITOR software ftp://ftp.ncbi.nih gov/pub/COG/old/util/xugnitor.c.
Volfovsky et al., 2001
Wheeler et al., 2005

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09771624B2). An electronic copy of the "Sequence Listing" will also be available from the USPTO upon request and payment of the fee set forth in 37 CFR 1.19(b)(3).

The invention claimed is:

1. A pharmaceutical ingestable carrier comprising more than $10^6$ cfu per gram of the ingestable carrier of an isolated strain of *Bifidobacterium longum* BL1207 deposited at ATCC with accession number PTA-9608, wherein the pharmaceutical ingestable carrier is a tablet, and wherein the strain induces a ratio of interleukin-10 to interleukin-12 of at least 10 in a peripheral blood mononuclear cell co-incubation assay.

2. A pharmaceutical ingestable carrier comprising more than $10^6$ cfu per gram of the ingestable carrier of an isolated strain of *Bifidobacterium longum* AH121A deposited at NCIMB with accession number NCIMB 41675, wherein the pharmaceutical ingestable carrier is a tablet, and wherein the strain induces a ratio of interleukin-10 to interleukin-12 of at least 10 in a peripheral blood mononuclear cell co-incubation assay.

3. A pharmaceutical ingestable carrier comprising more than $10^6$ cfu per gram of the ingestable carrier of an isolated strain of *Bifidobacterium longum* AH1714 deposited at NCIMB with accession number NCIMB 41676, wherein the pharmaceutical ingestable carrier is a tablet, and wherein the strain induces a ratio of interleukin-10 to interleukin-12 of at least 10 in a peripheral blood mononuclear cell co-incubation assay.

4. A method of improving gastrointestinal health in a subject, the method comprising administering a composition comprising a therapeutically effective amount of the pharmaceutical ingestable carrier of claim 1.

5. A method of improving gastrointestinal health in a subject, the method comprising administering a composition comprising a therapeutically effective amount of the pharmaceutical ingestable carrier of claim 2.

6. A method of improving gastrointestinal health in a subject, the method comprising administering a composition comprising a therapeutically effective amount of the pharmaceutical ingestable carrier of claim 3.

7. A method for providing a probiotic to a subject, the method comprising administering a composition comprising a therapeutically effective amount of the pharmaceutical ingestable carrier of claim 1.

8. A method for providing a probiotic to a subject, the method comprising administering a composition comprising a therapeutically effective amount of the pharmaceutical ingestable carrier of claim 2.

9. A method for providing a probiotic to a subject, the method comprising administering a composition comprising a therapeutically effective amount of the pharmaceutical ingestable carrier of claim 3.

* * * * *

UNITED STATES PATENT AND TRADEMARK OFFICE
CERTIFICATE OF CORRECTION

PATENT NO. : 9,771,624 B2
APPLICATION NO. : 12/616752
DATED : September 26, 2017
INVENTOR(S) : Douwe Van Sinderen et al.

It is certified that error appears in the above-identified patent and that said Letters Patent is hereby corrected as shown below:

On the Title Page

Below Abstract delete "9 Claims and 8 Drawing Sheets" insert --3 Claims and 8 Drawing Sheets--

In the Claims

Please delete the following Claims:
"1. A pharmaceutical ingestable carrier comprising more than $10.\sup.6$ cfu per gram of the ingestable carrier of an isolated strain of Bifidobacterium longum BL1207 deposited at ATCC with accession number PTA-9608, wherein the pharmaceutical ingestable carrier is a tablet, and wherein the strain induces a ratio of interleukin-10 to interleukin-12 of at least 10 in a peripheral blood mononuclear cell co-incubation assay.

2. A pharmaceutical ingestable carrier comprising more than $10.\sup.6$ cfu per gram of the ingestable carrier of an isolated strain of Bifidobacterium longum AH121A deposited at NCIMB with accession number NCIMB 41675, wherein the pharmaceutical ingestable carrier is a tablet, and wherein the strain induces a ratio of interleukin-10 to interleukin-12 of at least 10 in a peripheral blood mononuclear cell co-incubation assay.

3. A pharmaceutical ingestable carrier comprising more than $10.\sup.6$ cfu per gram of the ingestable carrier of an isolated strain of Bifidobacterium longum AH1714 deposited at NCIMB with accession number NCIMB 41676, wherein the pharmaceutical ingestable carrier is a tablet, and wherein the strain induces a ratio of interleukin-10 to interleukin-12 of at least 10 in a peripheral blood mononuclear cell co-incubation assay.

4. A method of improving gastrointestinal health in a subject, the method comprising administering a composition comprising a therapeutically effective amount of the pharmaceutical ingestable carrier of claim 1.

Signed and Sealed this
Twenty-sixth Day of June, 2018

Andrei Iancu
*Director of the United States Patent and Trademark Office*

5. A method of improving gastrointestinal health in a subject, the method comprising administering a composition comprising a therapeutically effective amount of the pharmaceutical ingestable carrier of claim 2

6. A method of improving gastrointestinal health in a subject, the method comprising administering a composition comprising a therapeutically effective amount of the pharmaceutical ingestable carrier of claim 3

7. A method for providing a probiotic to a subject, the method comprising administering a composition comprising a therapeutically effective amount of the pharmaceutical ingestable carrier of claim 1.

8. A method for providing a probiotic to a subject, the method comprising administering a composition comprising a therapeutically effective amount of the pharmaceutical ingestable carrier of claim 2.

9. A method for providing a probiotic to a subject, the method comprising administering a composition comprising a therapeutically effective amount of the pharmaceutical ingestable carrier of claim 3."

Please insert the following Claims:
--1. A pharmaceutical ingestable carrier comprising more than $10^6$ cfu per gram of the ingestible carrier of an isolated strain of Bifidobacterium longum BL1207 deposited at ATCC with accession number PTA-9608, wherein the pharmaceutical ingestable carrier is a tablet, and wherein the strain induces a ratio of interleukin-10 to interleukin-12 of at least 10 in a peripheral blood mononuclear cell co-incubation assay.

2. A method for providing a probiotic to a subject, the method comprising administering a composition comprising a therapeutically effective amount of the pharmaceutical ingestable carrier of claim 1.

3. A method of improving gastrointestinal health in a subject, the method comprising administering a composition comprising a therapeutically effective amount of the pharmaceutical ingestable carrier of claim 1.--